United States Patent
Sokoll et al.

(10) Patent No.: US 6,623,764 B1
(45) Date of Patent: *Sep. 23, 2003

(54) BIODEGRADABLE TARGETABLE MICROPARTICLE DELIVERY SYSTEM

(75) Inventors: Kenneth K. Sokoll, Alton (CA); Pele Chong, Richmond Hill (CA); Michel H. Klein, Willowdale (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/331,118

(22) PCT Filed: Dec. 19, 1997

(86) PCT No.: PCT/CA97/00980

§ 371 (c)(1),
(2), (4) Date: Aug. 31, 1999

(87) PCT Pub. No.: WO98/28357

PCT Pub. Date: Jul. 2, 1998

Related U.S. Application Data

(63) Continuation-in-part of application No. 08/770,850, filed on Dec. 20, 1996, now Pat. No. 6,082,820.

(51) Int. Cl.⁷ .......................... A61K 9/16; A61K 47/34; C08G 63/08
(52) U.S. Cl. .................... 424/501; 424/78.37; 528/318; 528/329.1
(58) Field of Search ................ 424/426, 443, 424/78.37, 501; 514/772.3; 525/54.11; 528/283, 288, 315, 318, 329.1

(56) References Cited

U.S. PATENT DOCUMENTS

| | | |
|---|---|---|
| 2,676,945 A | 4/1954 | Higgins |
| 3,839,297 A | 10/1974 | Wasserman et al. |
| RE30,170 E | 12/1979 | Goodman et al. |
| 4,855,283 A | 8/1989 | Lockhoff |
| 5,399,665 A | 3/1995 | Barrera et al. |
| 5,593,778 A | 1/1997 | Kondo et al. |
| 5,625,030 A | 4/1997 | Williams et al. |

FOREIGN PATENT DOCUMENTS

| | | |
|---|---|---|
| EP | 600161 | 6/1994 |
| WO | WO 94/09760 | 5/1994 |

OTHER PUBLICATIONS

Levine, M.M. et al—*Lancet*, 340, 1992, 689.
Eldridge, J.H. et al;—*J. Control. Release*, 11, 1990, 205.
Eldridge, J.H. et al—*Mol. Immunol.*, 28, 1991, 287.
O'Hagan, D.T. et al—*Vaccine*, 7, 1989, 213.
Mitsunobu, O.; *Synthesis*, 1981.
Zhou, Q., and Kohn, J., *J. Macromolecules*, 23, 1990, 3300.
Brode, G.L., et al—*J. Macromol. Sci–Chem.*, A6, 1972, 1109.
Kohn, F.E. et al—*J., Eur. Polym. J.*,19, 1983, 1081.
Kohn, F.E. et al—*Journal of Applied Polymer Science*, 29, 1984, 4265.
Kricheldorf, H.R.; and Dunsing, R., *Polymer Bulletin*, 14, 1985, 491.
Kricheldorf, H.R. et al;—*Macromol. Chem. Suppl.*, 12, 1985, 25.
Leenslag, J.W.; et al—*Makromol. Chem.*, 188, 1987, 1809.
Kricheldorf, H.R. et al—*Eur. Polymer J.*, 25, 1989, 585.
Hayashi, T. et al—*Biopolymers*, 29, 1990, 549.
Hayashi, T.; et al—*J. Appl. Polym. Sci.*, 43, 1991, 2223.
Hayashi, T. et al—*Polym. J.*, 5, 1993, 481.
Kohn, J.; and Langer, R., *J. Am. Chem. Soc.*, 109, 1987, 817.
Yonezawa, N.; Toda, F.; Hasegawa, M., *Makromol. Chem. Rapid Commun.*, 6, 1985, 607.
Helder, J.; and Feijen, J., *Makromol. Chem. Rapid Commun.*, 7, 1986, 193.
Veld, P.J. A.; Dijkstra, P.J.; Lochem, J.H. van; and Feigen, J.,*Makromol. Chem.*, 191, 1990, 1813.
Langer, R.; Barrera, D.A.; Zylstra, E.; and Lansbury, P.T., *J. Am. Chem. Soc.*, 115, 1993, 11010.
Barrera, D.A.; Zylstra, E.; and Lansbury, P.T., *Macromolecules.*, 28, 1995, 425.
Veld, P.J.A. et al—*J. Polymer Sci.*, 32(6), 1994, 1063.
Reed, A.M. and Gilding, D.K.; *Polymer*, 22, 1981, 494.

Greene, T.W. et al—*Protective Groups in Organic Synthesis II*, 335–338, John Wiley and Sons, Inc., New York, 1991.
Wiesmuller, *Vaccine*, 8, 1989, 29.
Huang, L. and Gao. X., Biochemical and Biophysical Research Communications, 179, 1991, 280.
Wood, J. M. et al.; Development of Biological Standard, 1977, 39, 193–200.
Palmer, D. F., et al—Advanced Laboratory Techniques for Influenza Diagnosis, Immunology Series No. 6, U.S. Dept. Health, Education and Welfare. Washington 02/08/00C.; 1975, 51–52.
Ruedl, C.; Rieser, C.; Kofler, N.; Wick, G. and Wolf, H.; Vaccine, 1996, 14, 792–798.
Lu, W. and Park, T. G.; Journal of Pharmaceutical Technology, 1995, 49, 13–19.
Gopferich, A.; Biomaterials; 17, 1996, 103.

*Primary Examiner*—Edward J. Webman
(74) *Attorney, Agent, or Firm*—Sim & McBurney

(57) ABSTRACT

Copolymers designed for use as particulate carriers containing functionalizable amino acid subunits for coupling with targeting ligands are described. The copolymers are polyesters composed of α-hydroxy acid subunits such as D,L-lactide and pseudo-α-amino acid subunits which may be derived from serine or terpolymers of D,L-lactide and glycolide and pseudo-α-amino acid subunits which may be derived from serine. Stable vaccine preparations useful as delayed release formulations containing antigen or antigens and adjuvants encapsulated within or physically mixed with polymeric mircoparticles are described. The particulate carriers are useful for delivering agents to the immune system of a subject by mucosal or parenteral routes to produce immune responses, including antibody and protective responses.

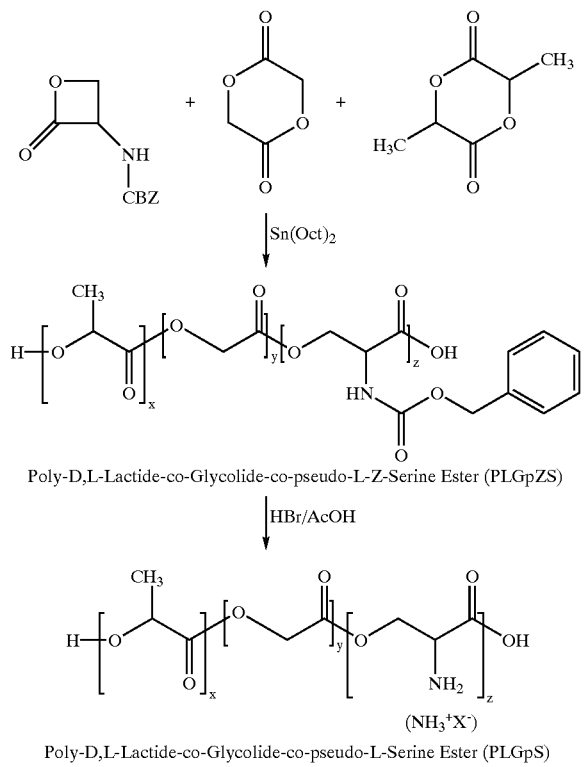

16 Claims, 37 Drawing Sheets

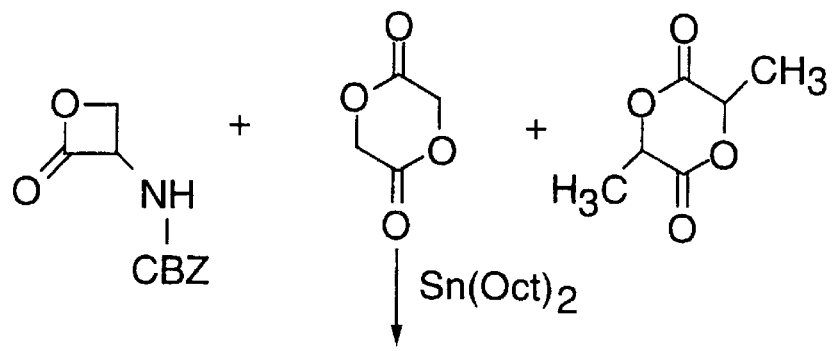
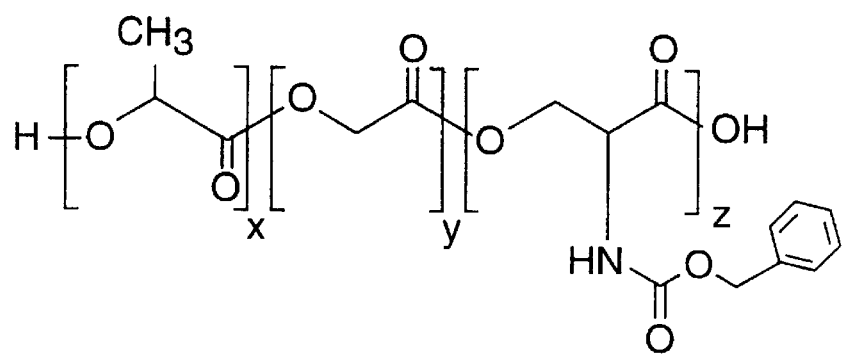
Poly-D,L-Lactide-co-Glycolide-co-pseudo-L-Z-Serine Ester (PLGpZS)
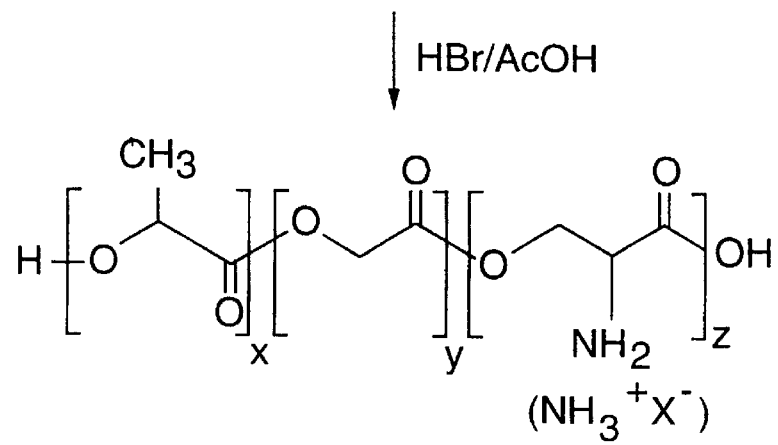
Poly-D,L-Lactide-co-Glycolide-co-pseudo-L-Serine Ester (PLGpS)
FIG.1

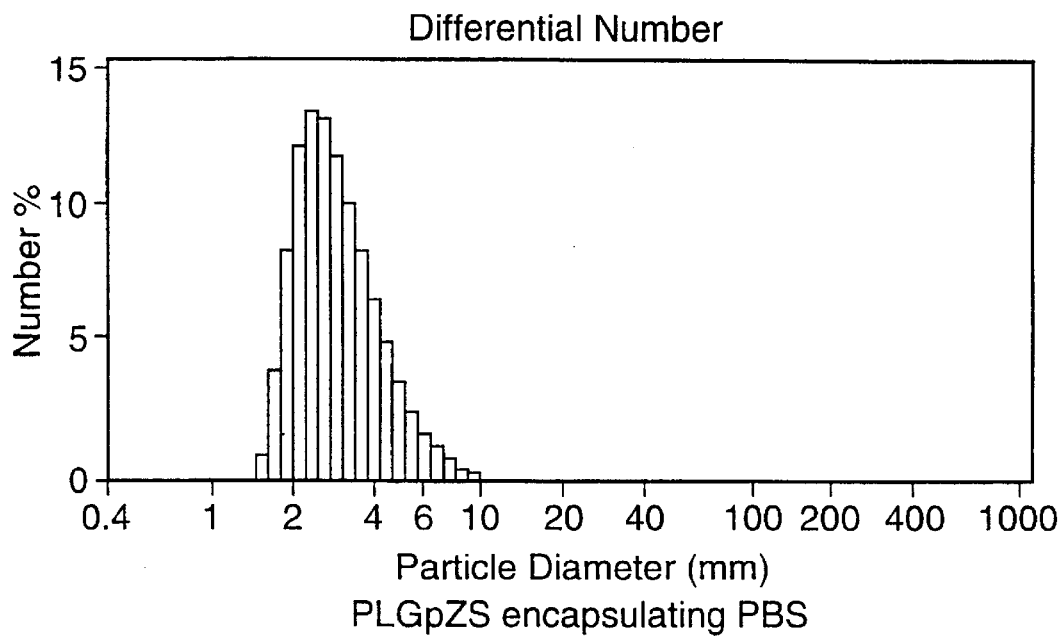
FIG.4A PLGpZS encapsulating PBS
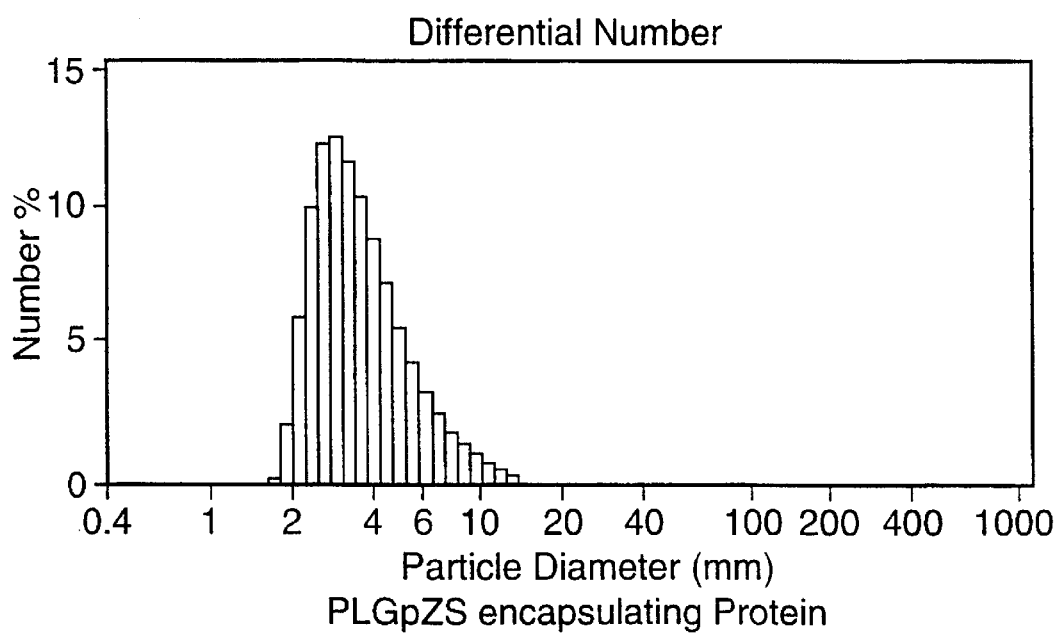
FIG.4B PLGpZS encapsulating Protein PLGpZS encapsulating PBS PLGpS encapsulating PBS PLGpZS encapsulating Antigen PLGpS encapsulating Antigen

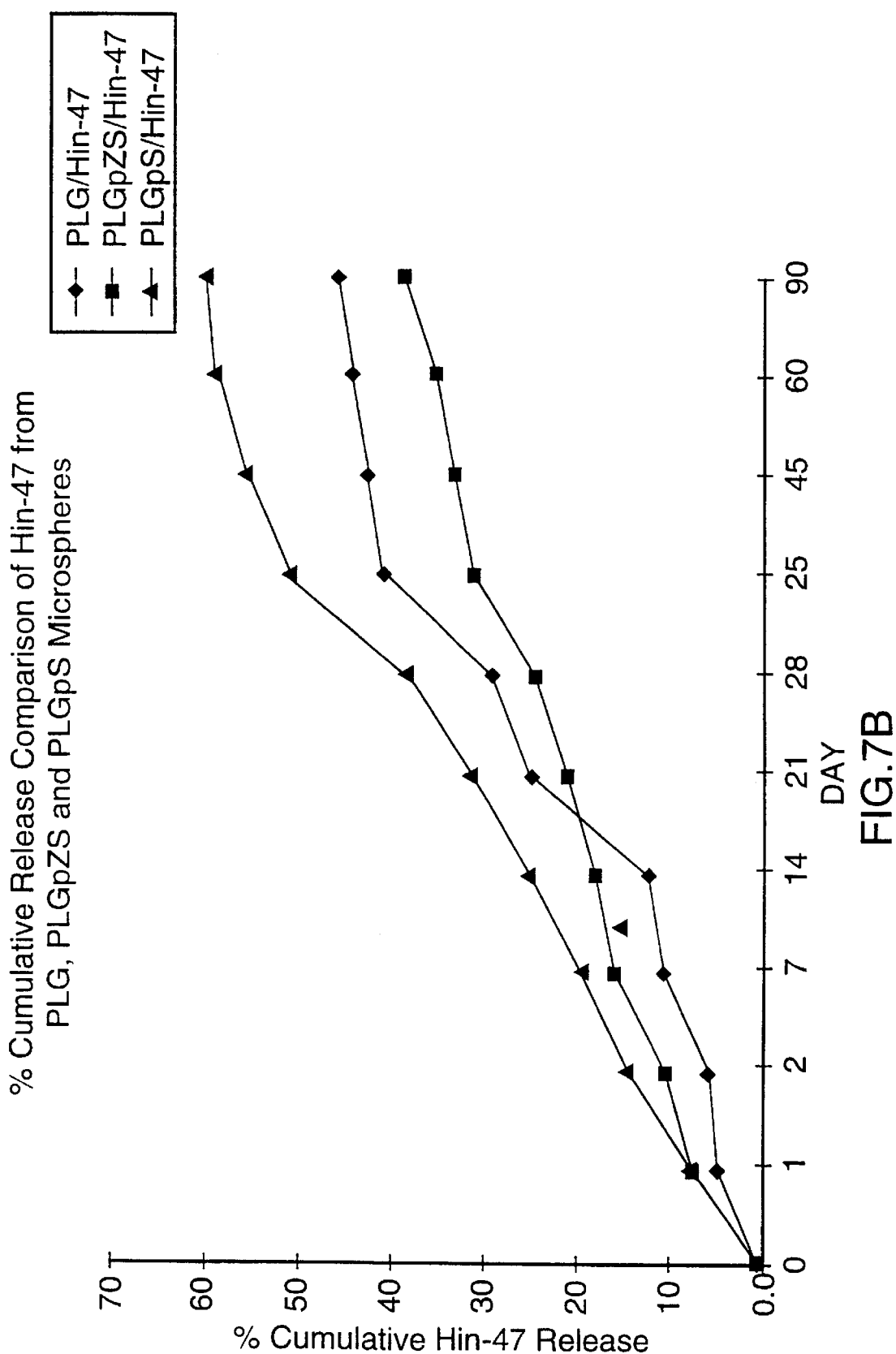

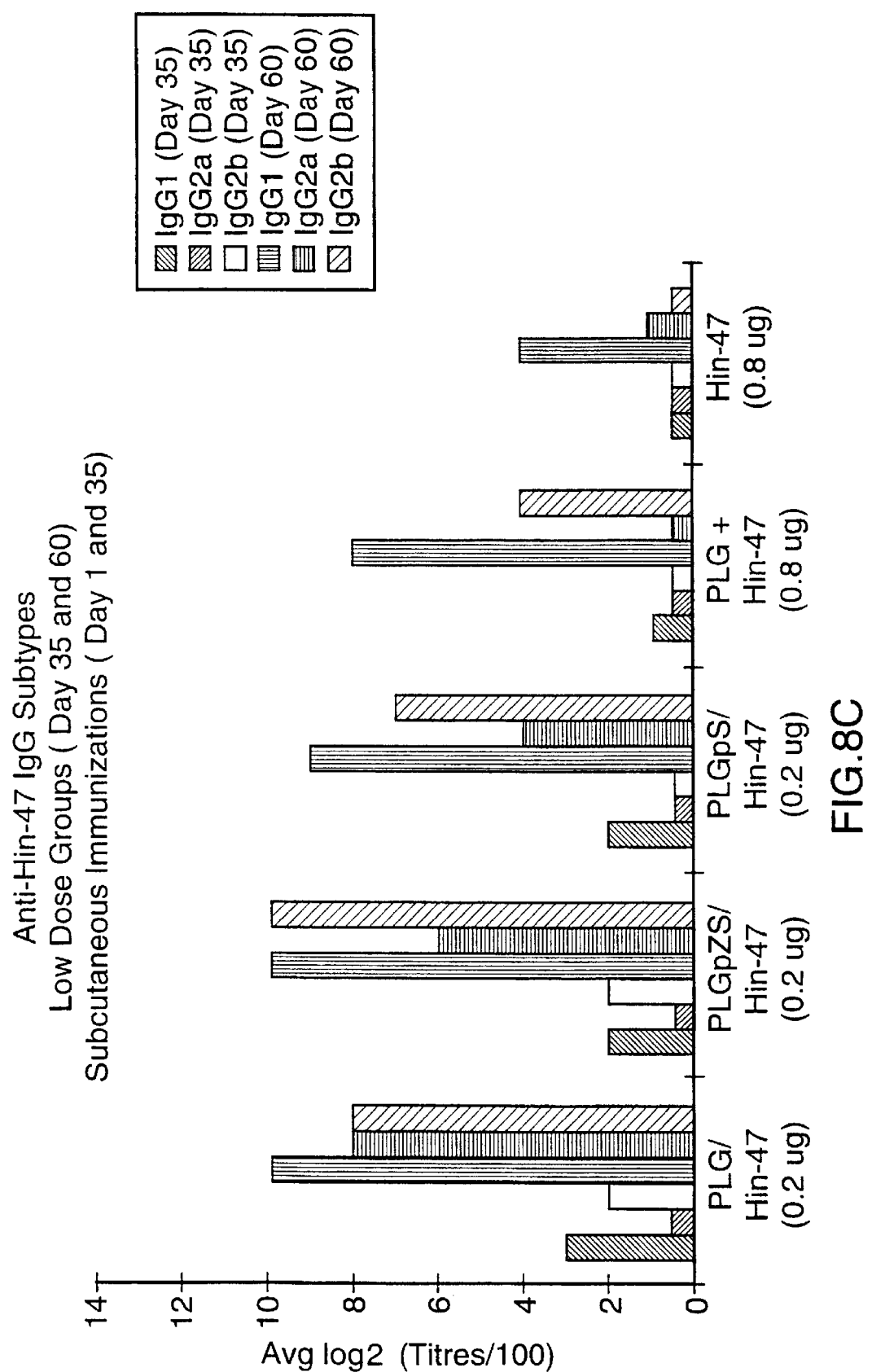

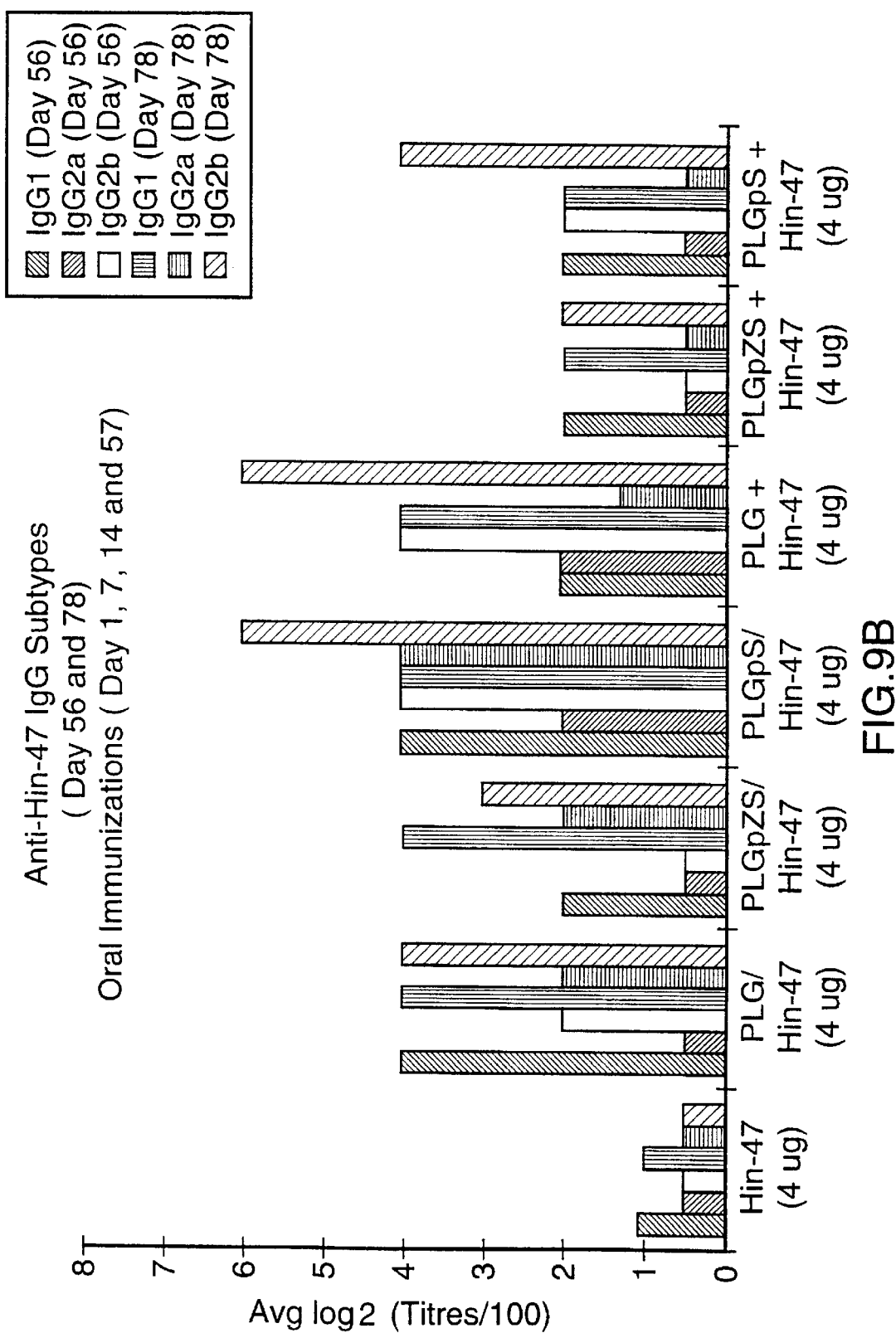

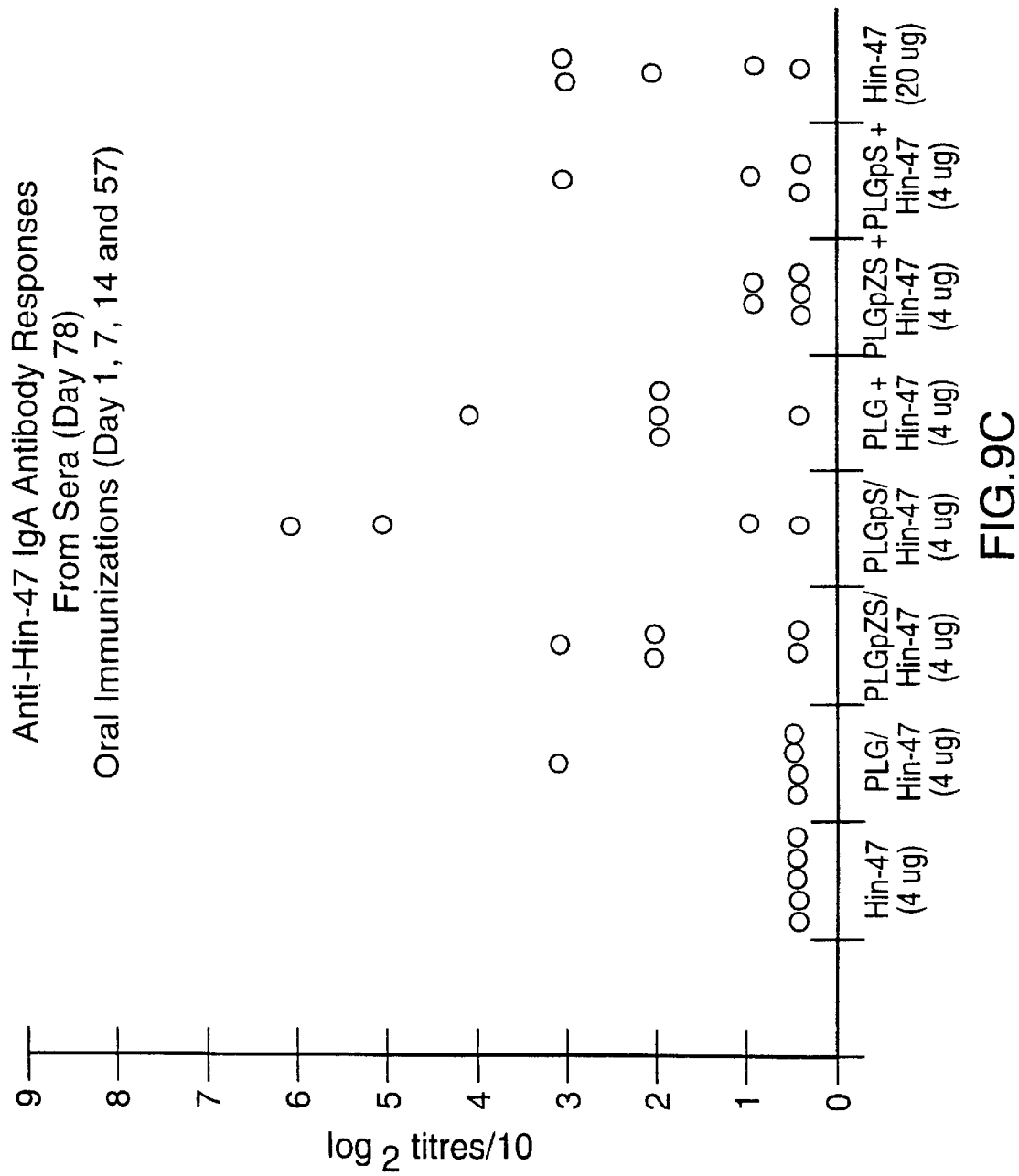

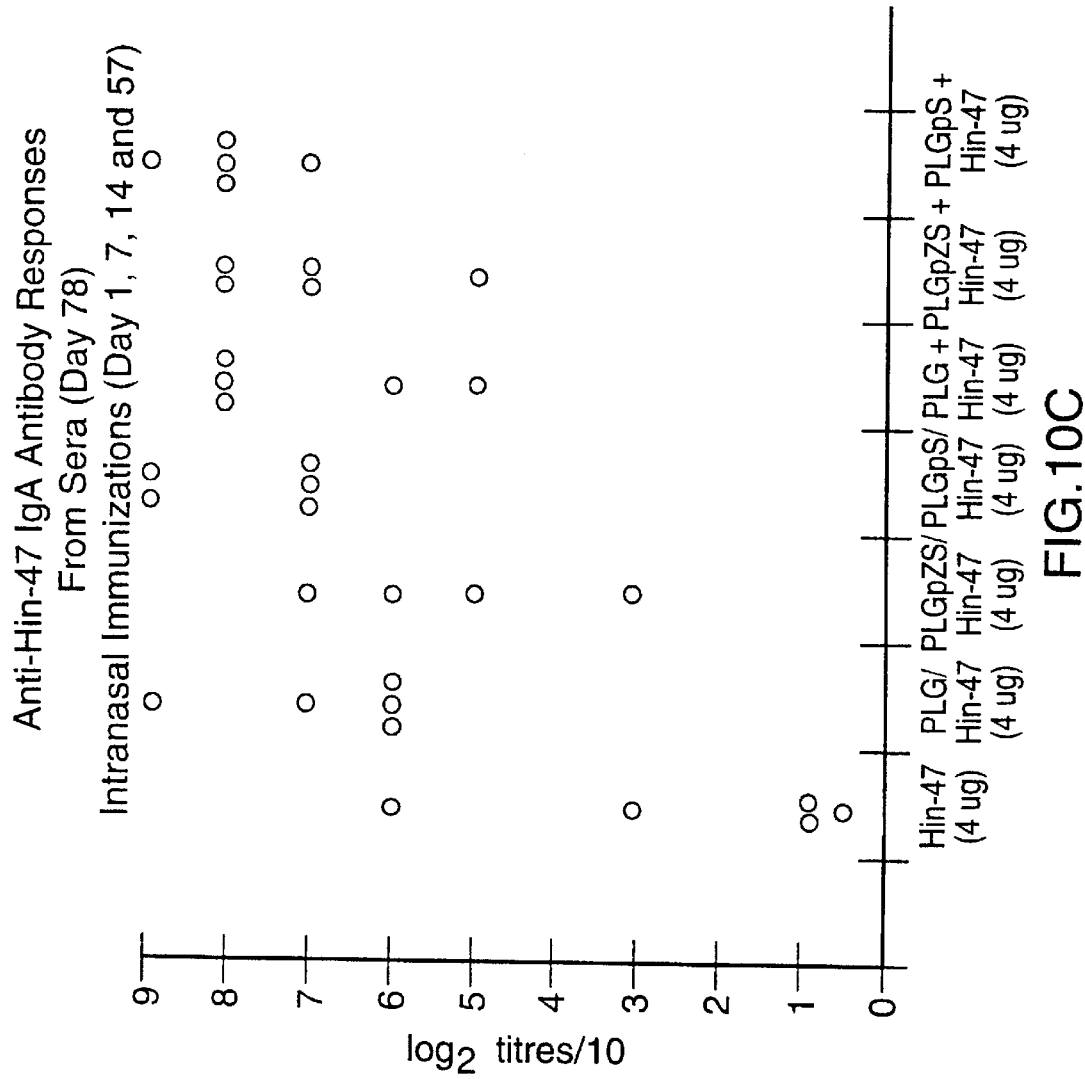

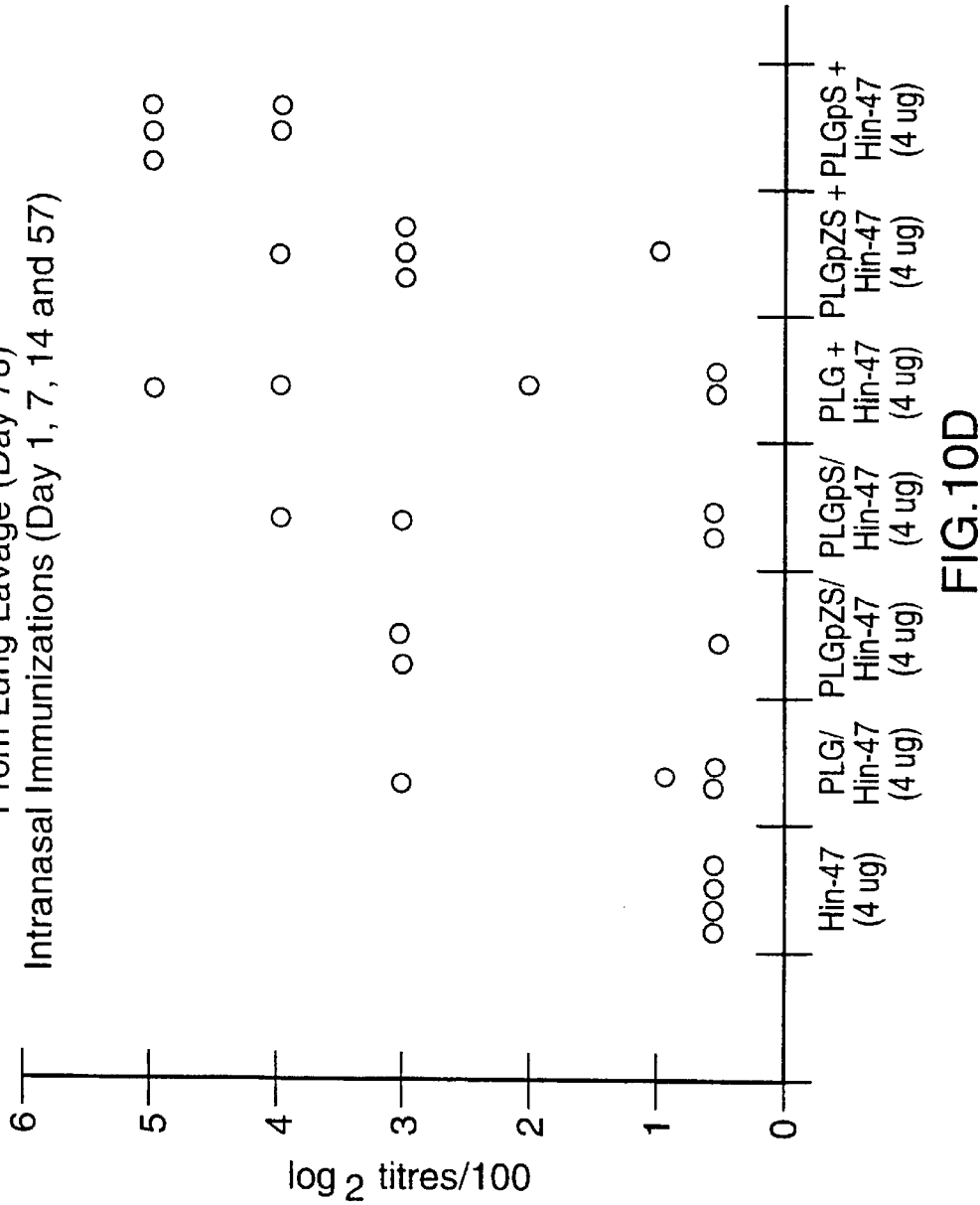

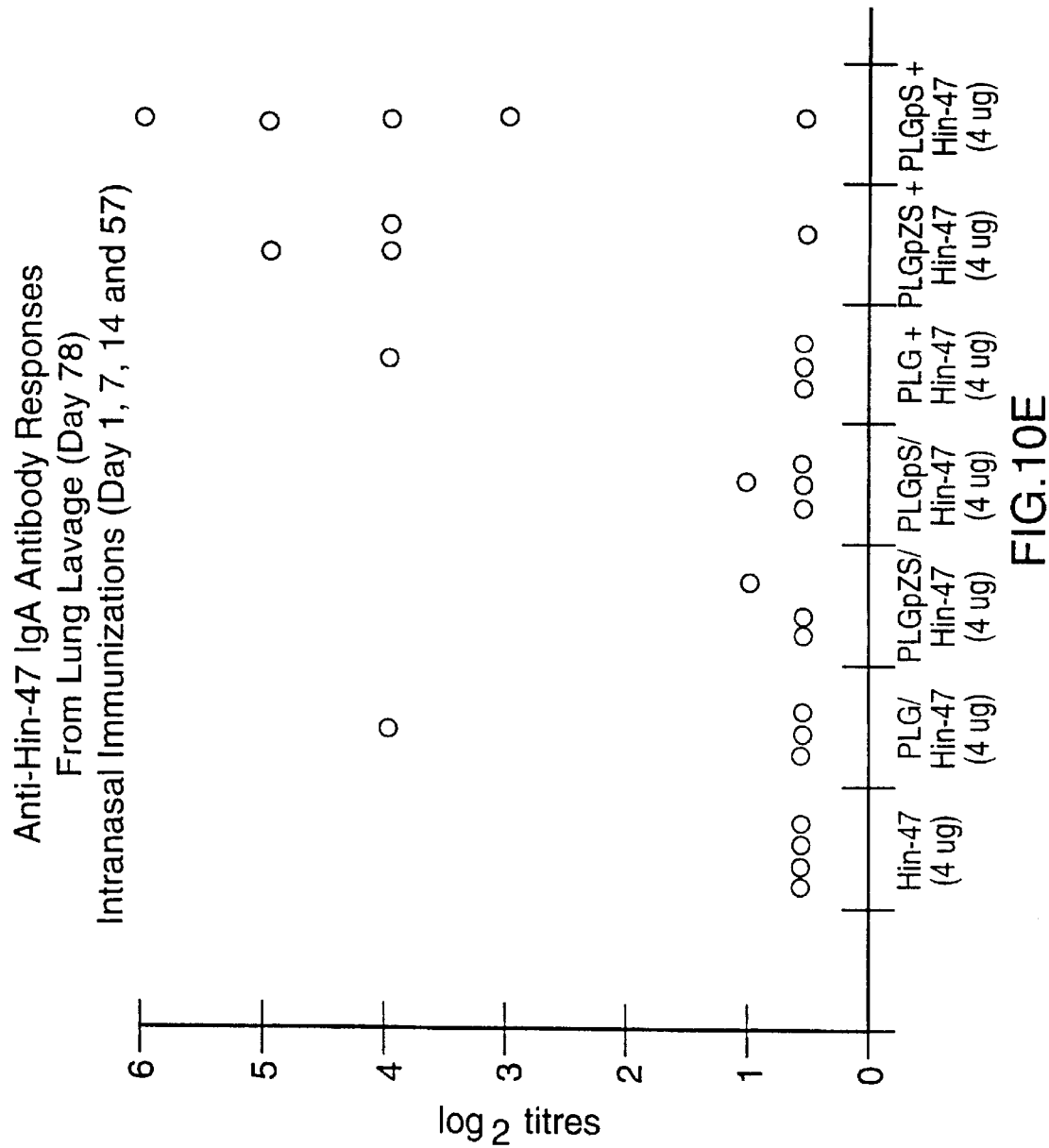

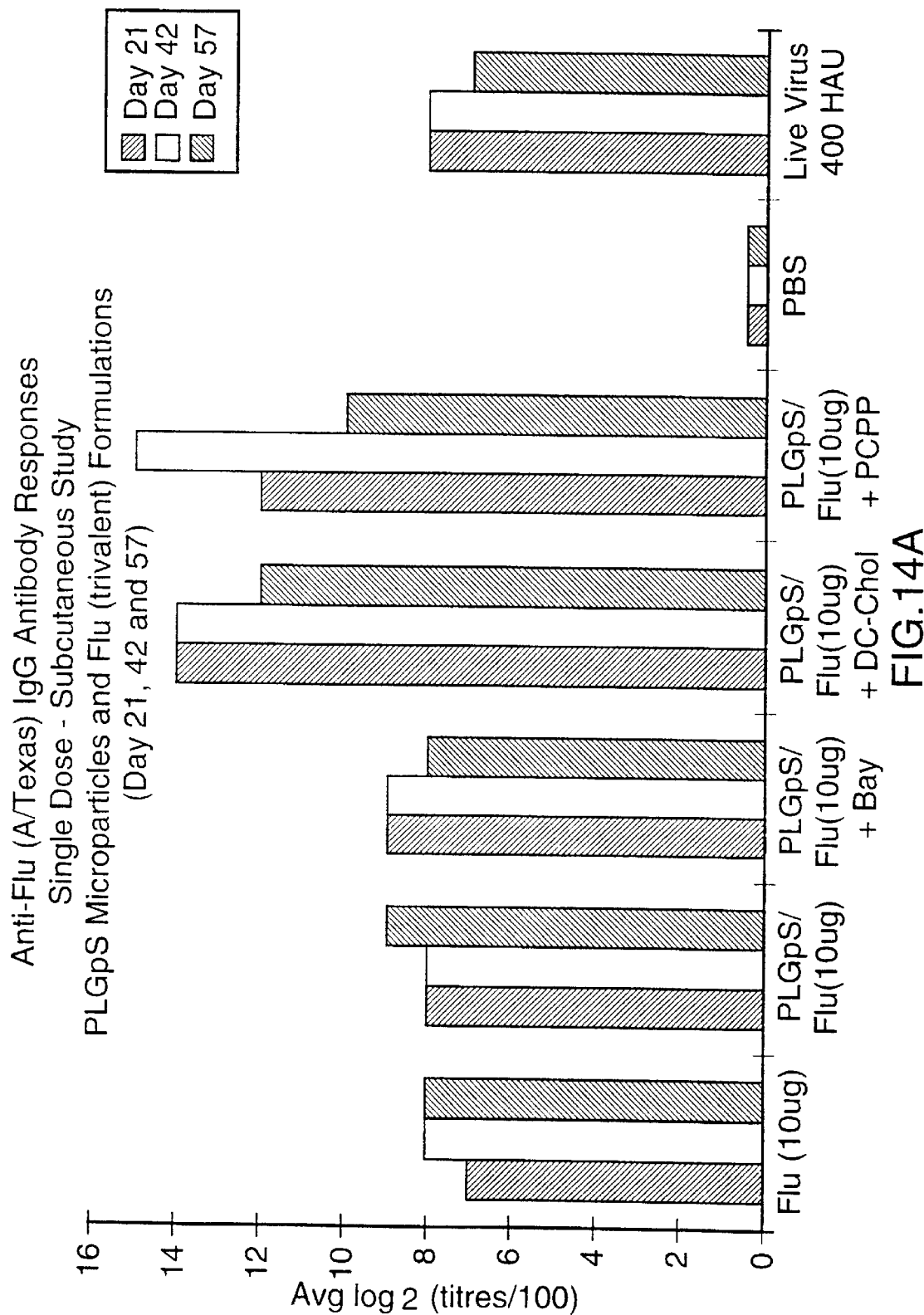

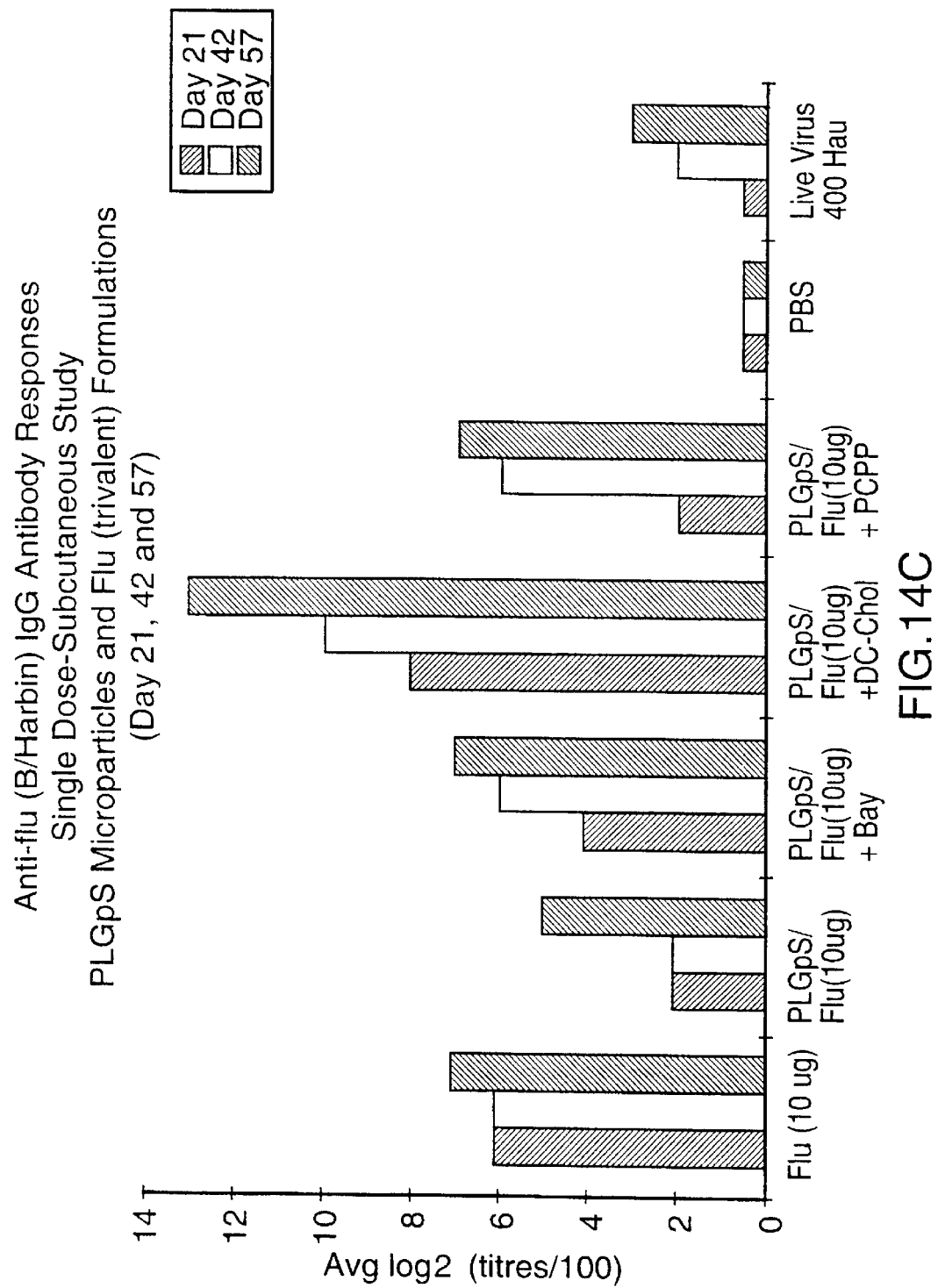

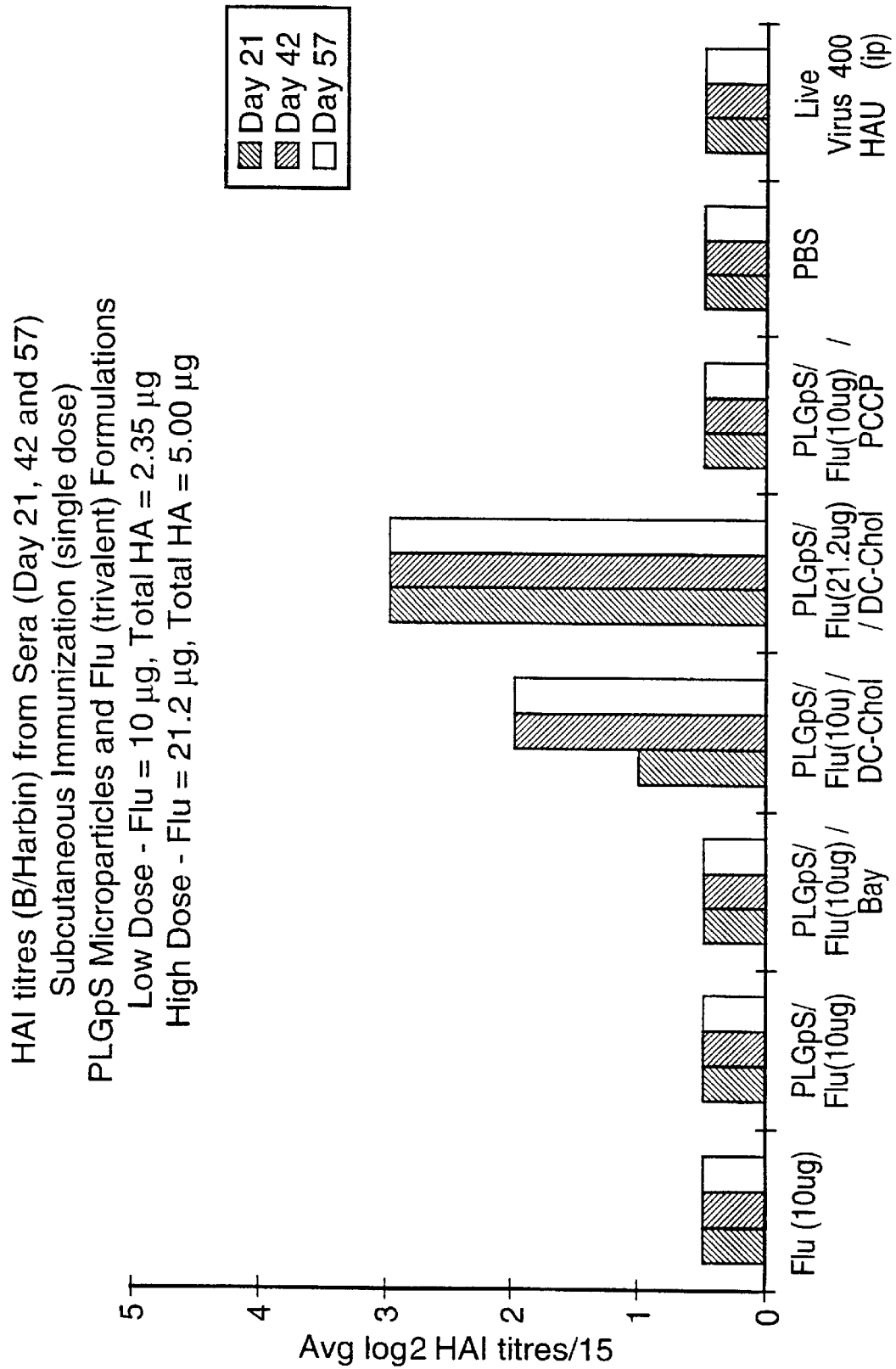

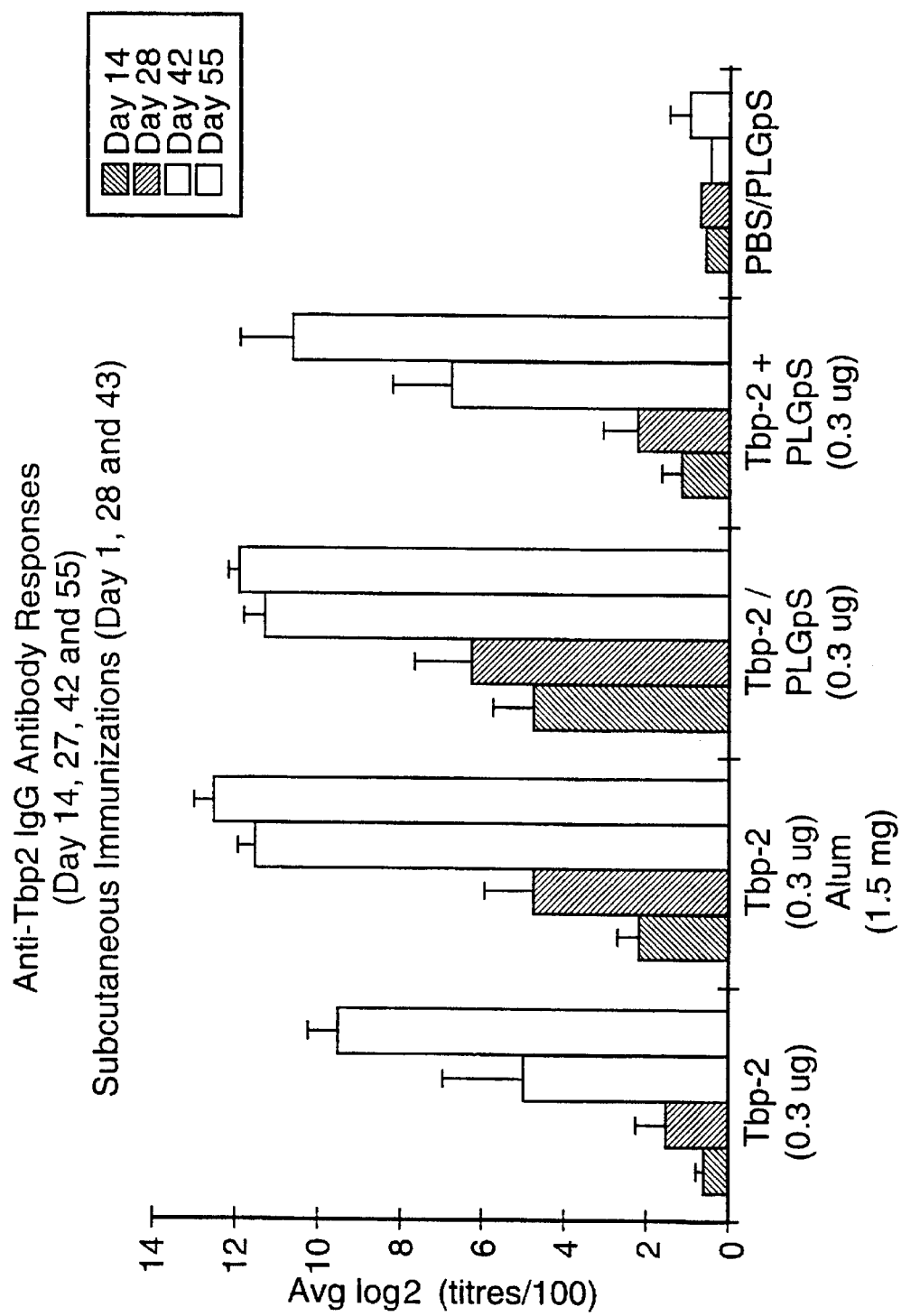

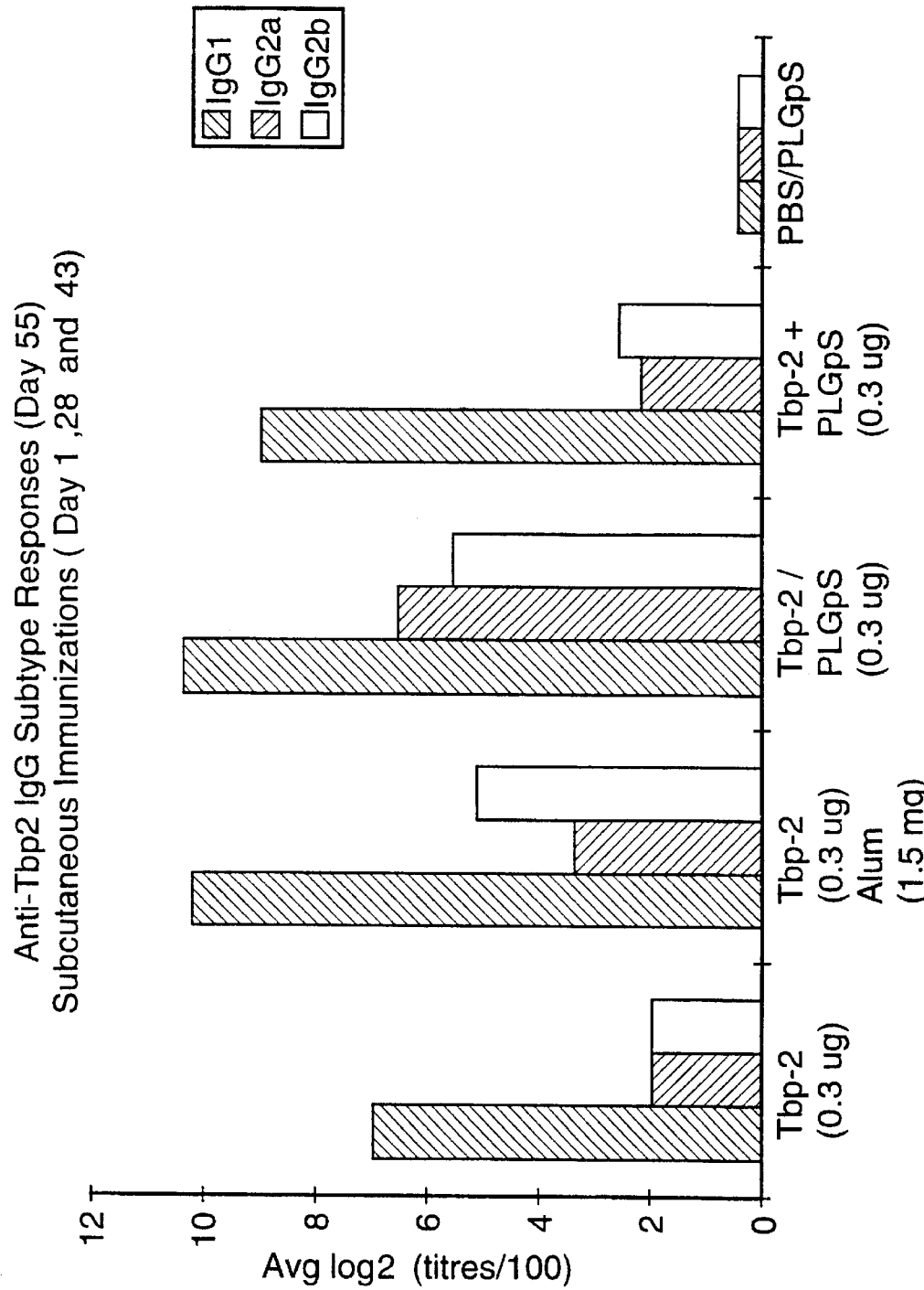

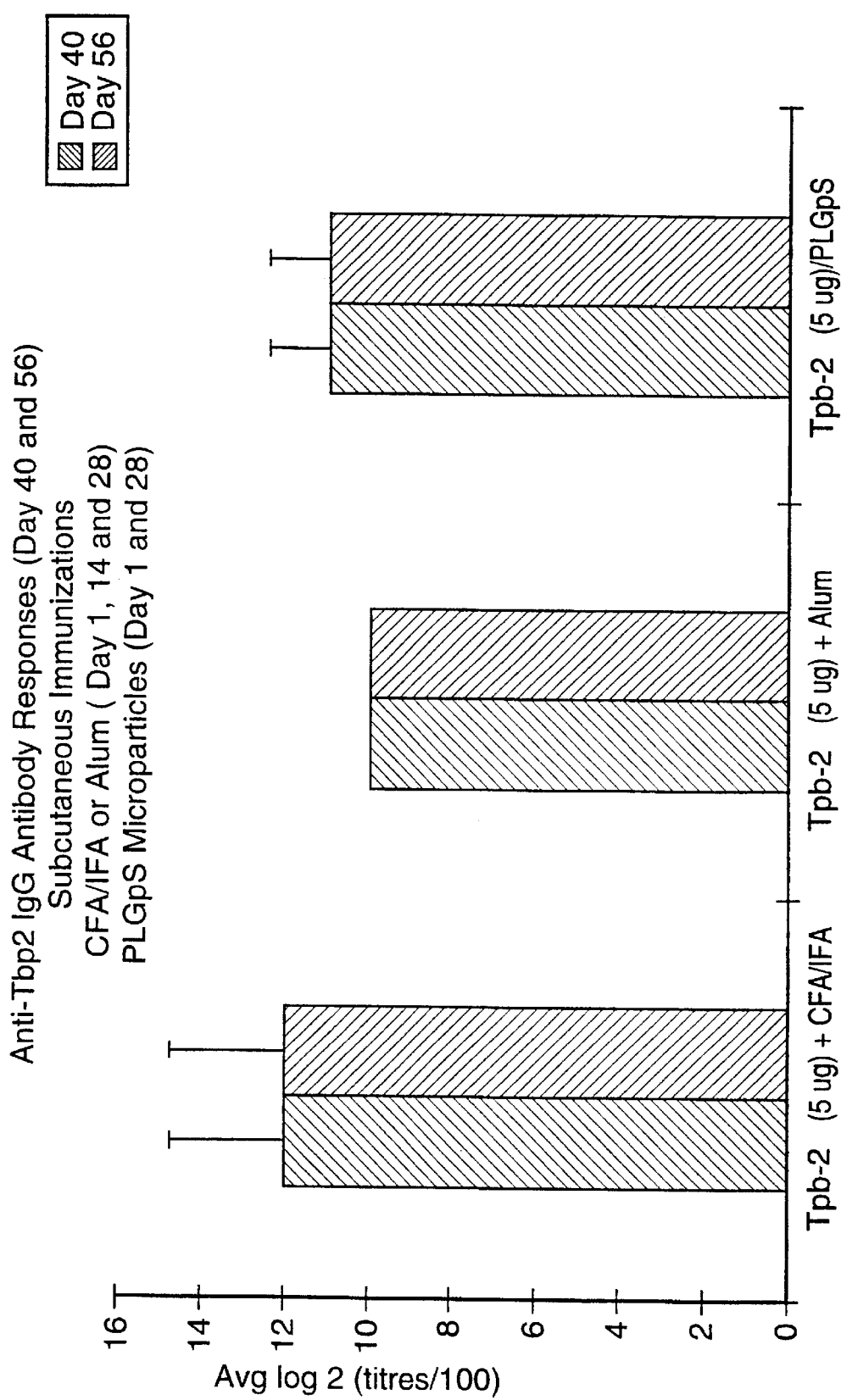

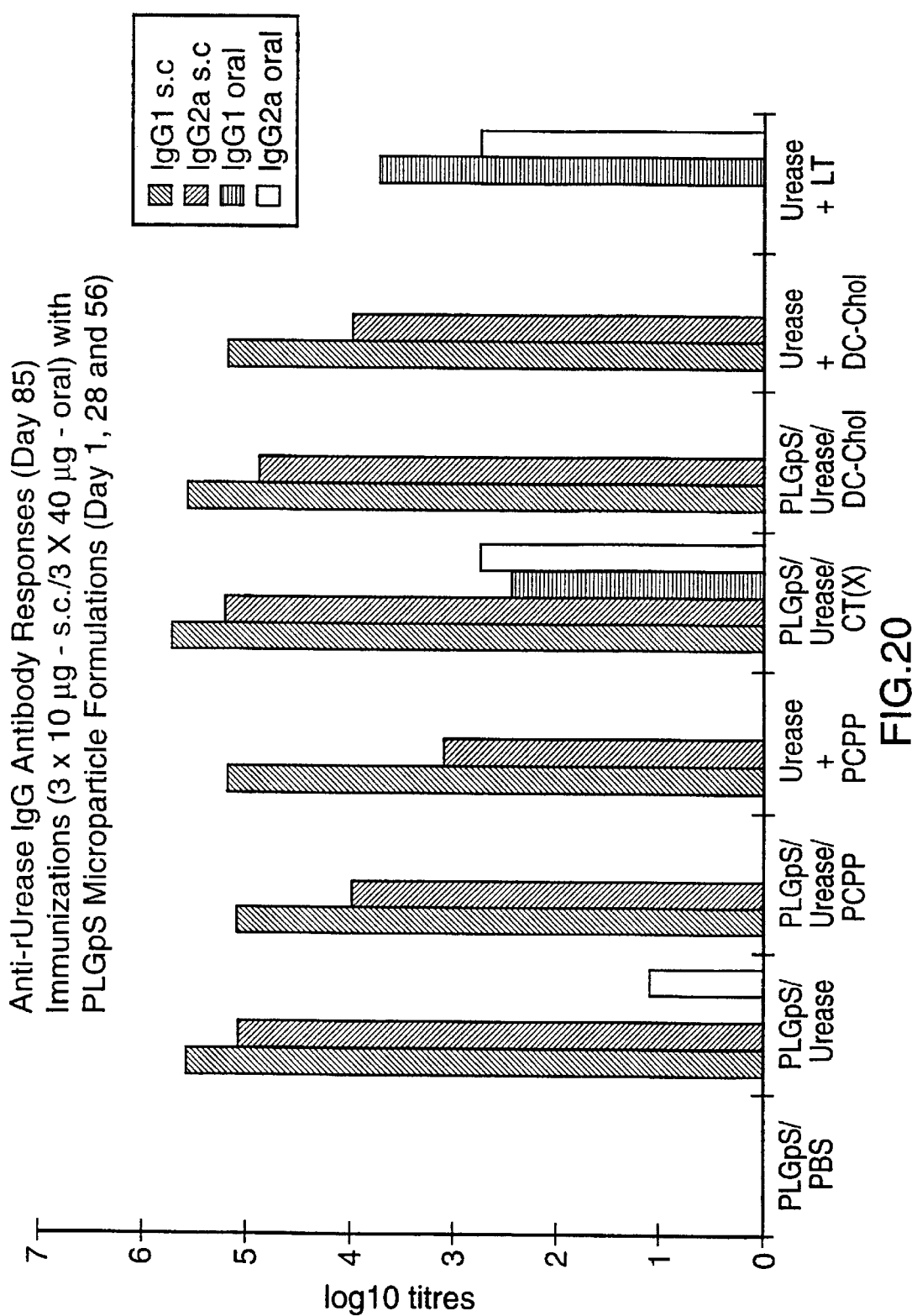

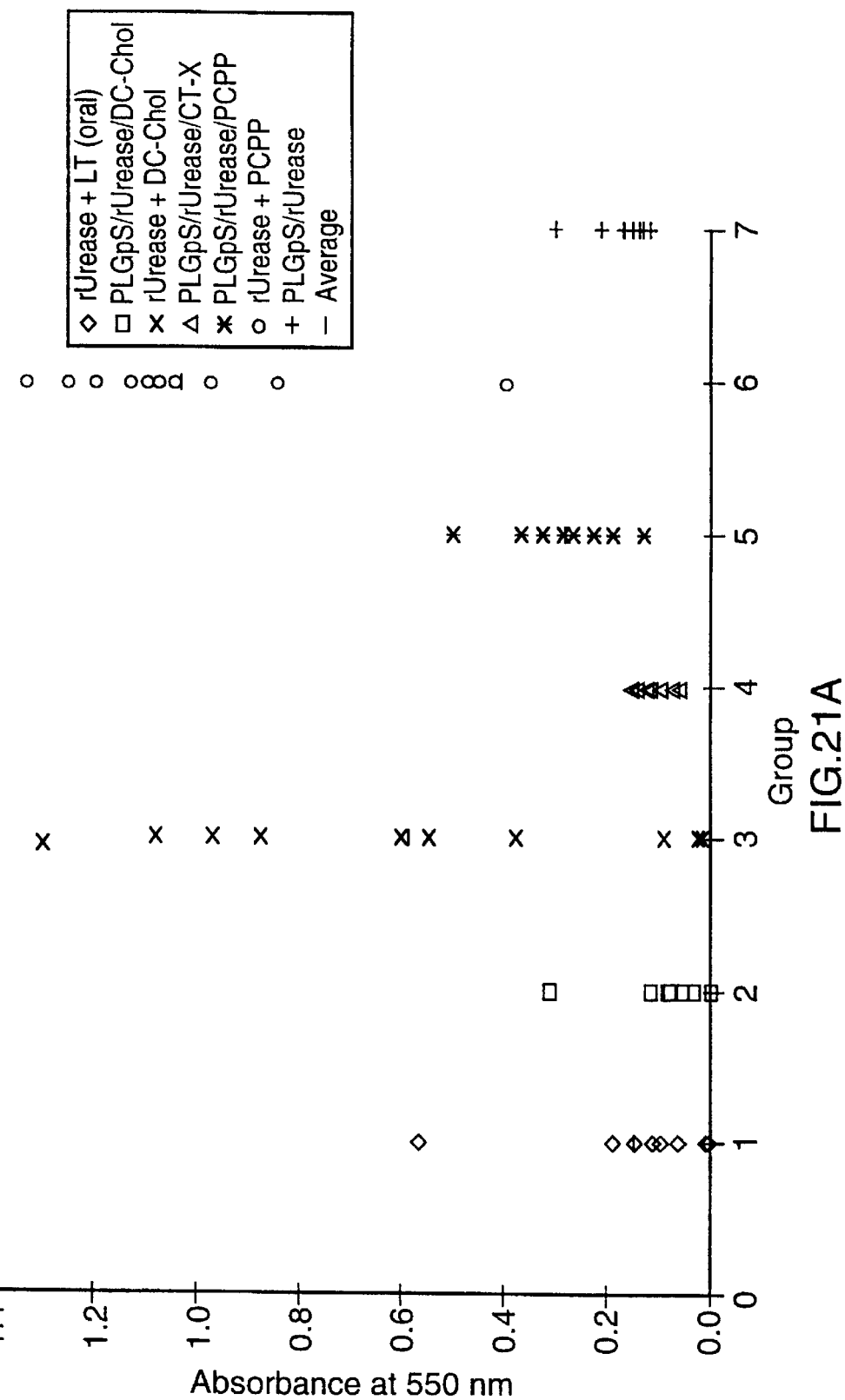

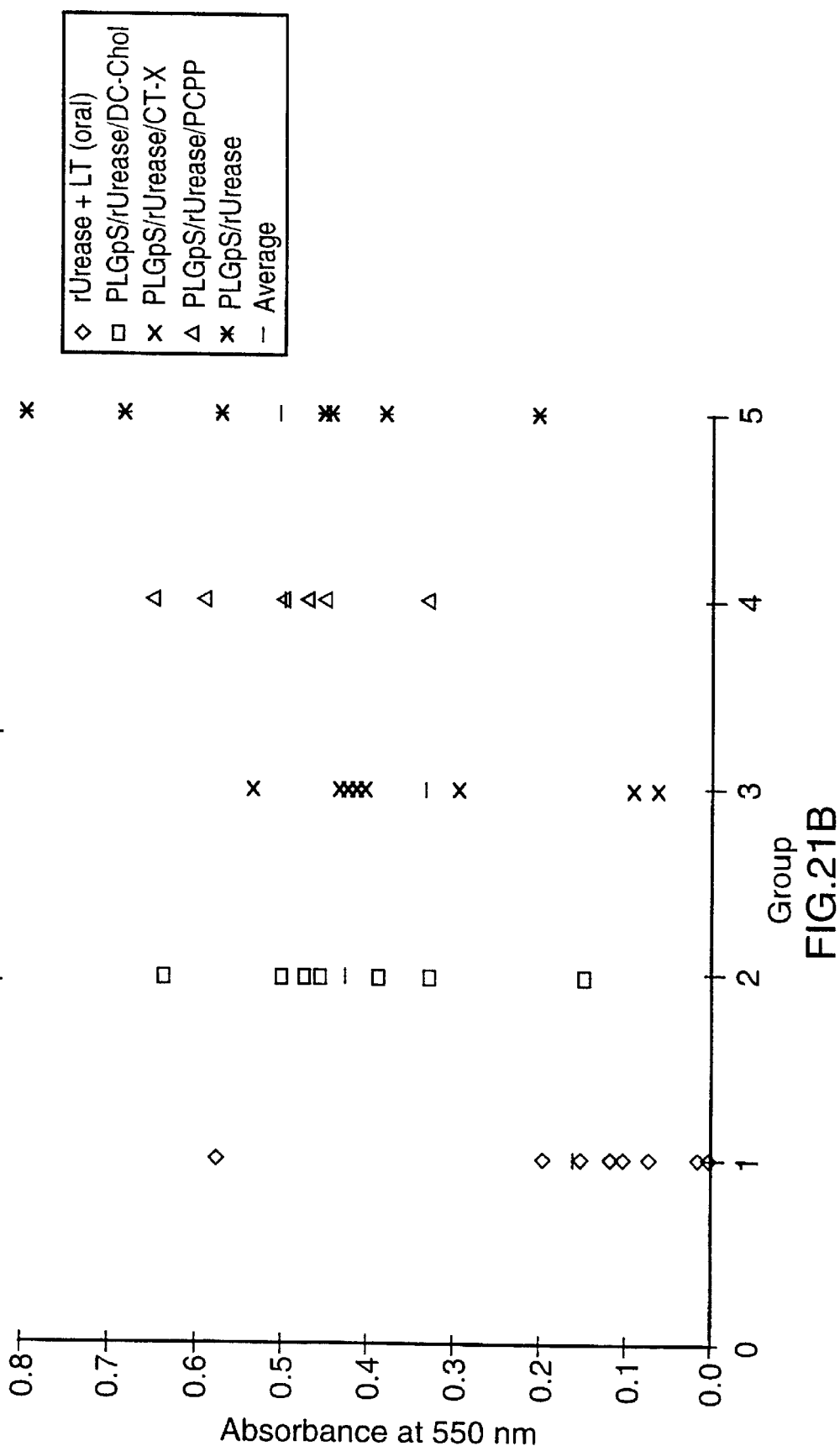

BIODEGRADABLE TARGETABLE MICROPARTICLE DELIVERY SYSTEM

REFERENCE TO RELATED APPLICATIONS

This application is a national phase application under 35 U.S.C. 371 of PCT/CA97/00980 filed Dec. 19, 1997, which is a continuation-in-part of U.S. patent application Ser. No. 08/770,850 filed Dec. 20, 1996 (now U.S. Pat. No. 6,082,820).

FIELD OF THE INVENTION

The present invention relates to biodegradable microparticles for delivery of a biologically active material and is particularly concerned with such microparticles that are targetable to particular cell types.

BACKGROUND OF THE INVENTION

Vaccines have been used for many years to protect humans and animals against a wide variety of infectious diseases. Such conventional vaccines consist of attenuated pathogens (for example, polio virus), killed pathogens (for example, Bordetella pertussis) or immunogenic components of the pathogen (for example, diphtheria toxoid and hepatitis B surface antigen).

Some antigens are highly immunogenic and are capable alone of eliciting protective immune responses. Other antigens, however, fail to induce a protective immune response or induce only a weak immune response. The immune response of a weakly immunogenic antigen can be significantly enhanced if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Adjuvants have been identified that enhance the immune response to antigens delivered parenterally.

Adjuvants are commonly employed with antigen in vaccine formulations whereby the induction of systemic immunity through parenteral immunization (intramuscular or subcutaneous) is obtained. This approach is suitable for infectious agents gaining access to the body via damaged skin (i.e. Tetanus), however, there are problems encountered due to side-effects and associated toxicity of many adjuvants administered in this fashion. Only those vaccines formulated from aluminum salts (aluminum phosphate or aluminum hydroxide) find routine use in human and veterinary vaccination. However, even these adjuvants are not suitable for use with all antigens and can also cause irritation at the site of injection. There is a clear need to develop adjuvants which safely enhance the immunogenicity of antigens at the site of injection.

There are other problems specific to the nature of the antigen being used. For example, most conventional non-living vaccines require multiple doses for effective immunization. Live attenuated vaccines and many nonliving liquid vaccines suffer from the need for controlled storage conditions and are susceptible to inactivation (e.g. thermal sensitivity). There are also problems associated with combining vaccines in single dosage forms, due to adjuvant incompatibilities, pH, buffer type and the presence of salts.

Mucosal immunity is induced primarily by induction of secretory immunoglobulin (sIgA) in intestinal, bronchial or nasal washings and other external secretions. For example, parenteral cholera vaccines have been shown to offer limited protection whereas the more recently developed oral form is highly effective (ref. 1—throughout this specification, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Studies with human volunteers have shown that oral administration of influenza vaccine is effective at inducing secretory anti-influenza antibodies in nasal secretions and substances have been identified which might be useful as adjuvants for such ingested vaccines. However, most of these adjuvants are relatively poor in terms of improving immune responses to ingested antigens. Currently, most of these adjuvants have been determined to be safe and efficacious in enhancing immune responses in humans and animals to antigens that are administered via the orogastrointestinal, nasopharyngeal-respiratory and genital tracts or in the ocular orbits. However, administration of antigens via these routes is generally ineffective in eliciting an immune response. Although the above example illustrates the potential of these immunization modes, the development of vaccine formulations for use by these routes has been slow for various reasons. The inability to immunize at the mucosal surface is generally believed to be due to include:

(i) antigen degradation via the acid and/or proteolytic enzymes present during the transit to the mucosal surfaces;

(ii) antigen degradation by secretions presented at the mucosal epithelium;

(iii) limited adsorption across the mucosal epithelium;

(iv) the dilution of the antigen to a concentration that is below that required to induce immune responses; and (v) ineffective adjuvants and/or delivery systems.

The problems associated with the use of adjuvants in parenteral vaccine formulations and the lack of suitable systems for vaccine delivery to mucosal sites understates the need for new techniques that are effective when administered by various routes and are inherently free from associated toxicity concerns or side-effects.

It is also desired to provide vaccine delivery in a single dosage form for both human and animal immunizations as this has the advantage of reducing time and cost, and in human medicine, increases patient compliance which is of extreme importance in developing countries where access is restricted. This is especially true for infants within these countries.

In order to increase immune responses to administered antigens, a carrier may be used to protect the antigen from degradation and also modulate the uptake of these materials in vivo. Sensitive antigens may be entrapped to protect them against destruction, reduction in immunogenicity or dilution. Methods for formulating a carrier include dispersing an antigen within a polymeric matrix (monolithic matrix) or by the coating of a polymeric material around an antigen to give an outer protective wall (core-shell). The manipulation of the formulation protocol can allow for control over the average size of these materials. This has been shown to be important for the uptake of particulates via oral delivery at specialized M-cells of the Peyers patches within the intestinal tract.

U.S. Pat. No. 5,151,264 describes a particulate carrier of a phospholipid/glycolipid/polysaccharide nature that has been termed Bio Vecteurs Supra Moleculairs (BVSM). The particulate carriers are intended to transport a variety of molecules having biological activity in one of the layers thereof. However, U.S. Pat. No. 5,151,264 does not describe particulate carriers containing antigens for immunization and particularly does not describe particulate carriers for immunization via the orogastrointestinal, nasapharyngeal-respiratory and urogenital tracts and in the ocular orbits or other mucosal sites.

Eldridge et al.(refs 2 and 3) observed the delayed release of antigen in vivo from biodegradable microspheres manufactured from polylactide-co-glycolide copolymer also known as PLG or PLGA. Numerous other polymers have been used to encapsulate antigens for formulation into microparticles and some of these include polyglycolide, polylactide, polycaprolactone, polyanhydrides, polyorthoesters and poly($\alpha$-hydroxybutyric acid).

U.S. Pat. No. 5,075,109 describes encapsulation of the antigens trinitrophenylated keyhole limpet hemocyanin and staphylococcal enterotoxin B in 50:50 poly (DL-lactide-co-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly ($\alpha$-hydroxybutyric acid), and poly anhydrides. The encapsulated antigen was administered to mice via gastric intubation and resulted in the appearance of significant antigen-specific IgA antibodies in saliva and gut secretions and in sera. As is stated in this patent, in contrast, the oral administration of the same amount of unencapsulated antigen was ineffective at inducing specific antibodies of any isotype in any of the fluids tested. Poly(DL-lactide-co-glycolide) microcapsules were also used to administer antigen by parenteral injection.

Published PCT application WO 91/06282 describes a delivery vehicle comprising a plurality of bioadhesive microspheres and antigenic vaccine ingredients. The microspheres being of starch, gelatin, dextran, collagen or albumin. This delivery vehicle is particularly intended for the uptake of vaccine across the nasal mucosa. The delivery vehicle may additionally contain an absorption enhancer. The antigens are typically encapsulated within protective polymeric materials.

U.S. Pat. No. 5,571,531 describes particulate carriers comprising a solid matrix of a polysaccharide and a proteinaceous material. A functionalized silicone polymer is bonded to the matrix for the delivery of materials having biological activity.

Although time-delayed release of antigen was shown in the above work, difficulties were encountered when microparticles are manufactured by the described methods. The exposure of biological materials to the organic solvents and physical forces used can lead to denaturation. It may be also be difficult to scale-up the procedures. Furthermore, hydrophilic antigens may be inefficiently encapsulated.

It would be desirable to provide improved carriers without such limitations. It would be particularly desirable to provide polymeric materials which can be formulated into microparticles and microspheres and which contain targeting moieties to target the antigen to preselected ligands. This would have tremendous potential for cells of the immune system.

SUMMARY OF THE INVENTION

The present invention is directed towards the production of a novel and useful polymer that has properties suitable for manufacturing by various processes into microparticles and microspheres. In this invention, modifications of existing processing procedures results in significant improvement in encapsulation efficiencies.

This invention is further directed to the production of useful vaccine delivery systems for antigen(s) or antigen and co-adjuvant cocktails by various immunization routes which include parenteral, oral and intranasal.

In accordance with a first aspect of the invention, there is provided a novel biodegradable, biocompatible polymer, including, those having a molecular weight of about 5,000 to about 40,000 daltons, having a backbone of the general formula:

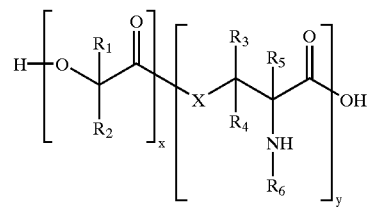

wherein;

$R_1$, $R_2$, $R_3$, $R_4$ and $R_5$ are selected independently and are selected from H, linear or branched alkyl groups;

$R_6$ is selected from H, an amine protecting group, a spacer molecule or a biologically active species;

X is selected from an O or S group; and x and y are integers, including values such that at least about 95% of the polymer is comprised of $\alpha$-hydroxy acid residues.

The novel polymers are derived by copolymerization of monomers comprising at least one $\alpha$-hydroxy acid or derivative thereof, including cyclic diesters and at least one pseudo-$\alpha$-amino acid. The $\alpha$-hydroxy acids are generally of the formula $R_1R_2COHCO_2H$, where the $R_1$ and $R_2$ groups are H, linear or branched alkyl groups. The $\alpha$-hydroxy acids may comprise a mixture of $\alpha$-hydroxy acids, at least one of the mixture of $\alpha$-hydroxy acids having $R_1$ and $R_2$ groups which are hydrogen and another $\alpha$-hydroxy acid having an $R_1$ group which is $CH_3$ and $R_2$ which is H. The pseudo-$\alpha$-amino acids are generally of the formula $R_5CHNHR_6CO_2H$, where the $R_5$ group is a hydroxyl methyl or methyl thiol group and $R_6$ is an amine protecting group.

The amine protecting groups may be carbobenzyloxy, benzyl, paramethoxybenzyl, benzyloxymethoxy, tert-butyloxycarbonyl or [9-fluorenylmethyloxy]carbonyl.

The $\alpha$-hydroxy acids are generally selected from L-lactic acid, D,L-lactic acid, glycolic acid, hydroxy valeric acid and hydroxybutyric acid. The at least one pseudo-$\alpha$-amino acid may be serine.

In a preferred aspect of the invention, the polymers are poly-D,L-lactide-co-glycolide-co-pseudo-Z-serine ester (PLGpZS) and poly-P,L-lactide-co-glycolide-co-pseudo-serine ester (PLGpS).

The polymers may contain biologically active moieties, such as cell bioadhesion groups, macrophage stimulators, polyethylene glycol, poly amino acids and/or protected amino acid residues, covalently bound to the polymer directly or through side groups.

In the preferred embodiment, the bioactive substituents are linked to the polymer via the amino groups on the amino acid moieties directly or via a suitable spacer molecule. The spacer molecule can be selected from $\alpha$-hydroxy acids represented by the formula $R_7R_8COHCO2H$, where $R_7$ or $R_8$ groups are independently selected from H, linear or branched alkyl units and α-amino acids represented by the formula $R_9CHNHR_{10}CO_2H$, where the $R_9$ group is a hydroxyl methyl or methyl thiol group and $R_{10}$ is an amine protecting group.

In accordance with a further aspect of the invention, the invention provides a method of making a biodegradable, biocompatible polyester, which comprises co-polymerizing at least one α-hydroxy acid and at least one pseudo-α-amino acid.

In accordance with another aspect of the present invention, there is provided a process for making a biodegradable, biocompatible polymer of the general formula provided herein which comprises forming a mixture of monomers comprising at least one α-hydroxy acid and at least one pseudo-α-amino acid with an organic solvent solution of an esterification catalyst under inert atmospheric conditions, copolymerizing the monomers and isolating the resultant polymer. The catalyst used is preferably stannous 2-ethylhexanoate.

The polymer formed by the process can be further deprotected by solid phase catalytic reduction or alternatively by acid catalysis using hydrogen bromide in acetic acid solution.

The process can also further comprise forming the polymer into a film or microparticles.

In accordance with another aspect of this invention, there is provided a particulate carrier for the delivery of biologically active materials to a host, the carrier comprising a polymer, including those having a molecular weight of about 5,000 to about 40,000 daltons, having the general formula:

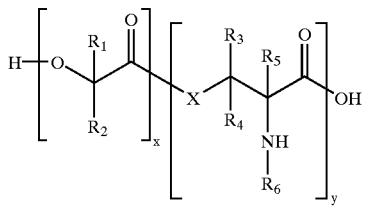

wherein;

$R_1$, $R_2$, $R_3$, $R_4$ and $R_5$ are selected independently and are selected from H, linear or branched alkyl groups;

$R_6$ is selected from H, an amine protecting group, a spacer molecule or a biologically active species;

X is selected from an O or S group; and x and y are integers, including values such that at least about 95% of the polymer is comprised of α-hydroxy acid residues.

The particulate carrier generally has a particle size of about 1 to 50 μM.

In a further aspect of the present invention is a process for making a particulate carrier for the delivery of at least one biologically active material to a host, the process comprising:

(a) mixing an organic solvent phase comprising an α-hydroxy acid polymer or copolymer with an aqueous composition comprising dispersed or dissolved biologically active material to form a first water-in-oil emulsion;

(b) dispersing the first water-in-oil emulsion into an aqueous detergent phase to form a second water-in-oil-in-water double emulsion;

(C) removing water from the second double emulsion to form microspheres; and (d) collecting the microspheres and having the biological material entrapped therein.

The particulate carrier of the present invention can be used as a composition having a biologically active material mixed therewith or entrapped within. The biological materials used may be selected from those which elicit an immune response. Such materials may comprise *Haemophilus influenzae* proteins, such as a non-proteolytic Hin-47 analog, D15, P1, P2, and P6. The biologically-active material may comprise at least one influenza virus, which may be a multivalent or monovalent influenza virus vaccine, or influenza virus protein, such as an influenza virus monovalent protein vaccine. In addition, the biologically-active material may comprise at least one *Moraxella catarrhalis* protein, such as the Tbp2 protein of *M. catarrhalis*. A further biologically-active material which may be employed may be at least one *Helicobacter pylori* protein, such as Urease. Other biological material may include proteins, protein mimetics, bacteria, bacterial lysates, viruses (e.g. respiratory syncytial virus), virus-infected cell lysates, DNA plasmids, antisense RNA, peptides (e.g. CLTB-36 and M2), antigens, antibodies, pharmacological agents, antibiotics, carbohydrates, lipids, lipidated amino acids (e.g. tripalmitoyl cysteine), glycolipids, haptens and combinations and mixtures thereof.

The first water-in-oil emulsion may additionally comprise at least one organic solvent soluble adjuvant, which may be lipophilic. Such organic solvent adjuvant may be selected from the group consisting of BAY R1-005, tripalmitoyl cysteine and DC-chol. The presence of a lipophilic moiety serves to increase the encapsulation efficiency and to protect the antigen during formulation and release and enables the particles to present antigen to the immune system more efficiently than traditional formulation and hence provides a more efficacious vaccine.

The first water-in-oil emulsion also may additionally comprise at least one water soluble adjuvant, which may be a polymeric water soluble adjuvant, such as PCPP or a mucosal adjuvant, such as CT-X or subunit thereof or LT. The presence of the water soluble adjuvant serves to increase the encapsulation efficiency of the process and protects the antigen during formulation and release and prevents the antigen to the immune system more efficiently than traditional microparticle formulation, thereby providing a more efficancious vaccine.

The present invention also provides an immunogenic composition comprising the particulate carrier provided herein and a physiologically acceptable carrier therefor. The composition can be administered mucosally or parenterally. The immune response is an antibody response which is a local or serum antibody response. In accordance with this aspect of the invention, there is provided a controlled or delayed release vaccine preparation in stable particulate form and a method of making such a vaccine preparation. The particles are microspherical and contain a matrix of biodegradable polymer and antigen(s) and/or antigen plus co-adjuvant containing regions.

Advantages of the invention include:

(a) fully biodegradable and biocompatible microparticle formulation;

(b) facilitated antigen presentation to the cells of the immune system resulting in improved antigen immunogenicity;

(c) improved formulating conditions which increase the bioavailability of the antigen.

Additional embodiments of the present invention include the use of the particulate carrier in diagnostic assays and for therapeutic strategies.

BRIEF DESCRIPTION OF THE DRAWINGS

The present invention will be further understood from the following description with reference to the drawings, in which:

FIG. 1 is a schematic showing the ring opening polymerization (ROP) of lactic acid dimer with glycolic acid dimer and N-(carbobenzyloxy)-L-serine lactone with subsequent deprotection in accordance with a preferred aspect of the present invention.

FIG. 7B compares the % cumulative release of non-proteolytic Hin-47 analog from PLG, PLGpZS and PLGpS microparticles over a three month period obtained from ~14 mg samples (typical core loadings range from 2.5 to 5.7 μg protein/mg of microparticles) that were incubated in PBS (pH=7.4) at maintained and 37° C.

FIG. 8C shows the serum IgG response subtype profile for pooled bleeds obtained on days +35 and +60 from the study conducted as described in FIG. 8A and 8B.

FIG. 9B shows the serum IgG response subtype profile for pooled bleeds obtained on days +56 and +78 from the study conducted as illustrated in FIG. 9A.

FIG. 9C shows the serum IgA response for the bleed obtained on day +78 from the study conducted as illustrated in FIG. 9A.

FIG. 10C shows the serum IgA response for the bleed obtained on day +78 from the study conducted as described in FIG. 10A.

FIG. 10D shows the lung lavage IgG response obtained on day +78 from the study conducted as described in FIG. 10A.

FIG. 10E shows the lung lavage sIgA response obtained on day +78 from the study conducted as described in FIG. 10A.

FIGS. 14a to c show the anti-Flu (trivalent) IgG serum antibody responses (for each influenza virus strain contained in trivalent vaccine; A/Texas (FIGS. 14a), A/Johannesburg (FIG. 14b) and B/Harbin FIG. 14C)) following various immunization protocols. Groups of 8 mice were immunized subcutaneously (S.C.) on day 1 with 250 μL of PBS, pH 7.4, containing 2.35 μg of total HA (about ⅓ specific HA from each strain) incorporated into PLGpS microparticles or PLGpS microparticles formulated in the presence of BAY R1-005, DC-Chol or PCPP. Sera obtained on days +21, +42 and +57 and were evaluated for the presence of anti-Flu (trivalent) IgG antibodies (A/Texas, A/Johannesburg and B/Harbin) using an enzyme-linked immunosorbent assay (ELISA).

FIGS. 15a to c show the strain specific hemagglutination inhibition antibody assay (i.e. A/Texas (FIG. 15a), A/Johannesburg (FIG. 15b) and B/Harbin (FIG. 15c)) responses (days +21, +42 and +57) following a single dose subcutaneous administration. Groups of 8 mice were immunized subcutaneously (S.C.) on day 1 with 250 μL of PBS, pH 7.4, containing either 2.35 μg of total HA incorporated into PLGpS microparticles or 2.35 μg of total HA into PLGpS microparticles coencapsulating BAY R1-005, DC-Chol or PCPP. Sera obtained on days +21, +42 or +57 were evaluated for the inhibition of hemagglutination of erythrocytes.

FIG. 17a shows the serum IgG antibody responses in mice immunized subcutaneously (S.C.) following various immunization protocols by the transferrin binding protein from *Moraxella catarrhallis* (Tbp-2) Groups of 5 mice were immunized on days 1, 28 and 43 with 250 μL of PBS pH 7.4, containing 0.3 μg of tbp-2 incorporated into PLGpS microparticles, physically mixed PLGpS microparticles or formulated with Alum. Sera obtained on days +14, +27, +42 and +55 were evaluated for the presence of anti-tbp-2 IgG antibodies using an enzyme-linked immunosorbent assay (ELISA).

FIG. 17b shows the serum IgG antibody subtype response profile for pooled bleeds obtained on day 55 from the study conducted as described in FIG. 17a.

FIG. 19 shows the serum IgG antibody responses in guinea pigs immunized parenterally following various immunization protocols by the transferrin binding protein from *Moraxella catarrhallis* (Tbp-2). Groups of 2 guinea pigs were immunized intramuscularly with 5 μg of Tbp-2 formulated with 400 μL of CFA on day 1 followed subcutaneously with 5 μg of Tbp-2 formulated in 500 μL of IFA on days 14 and 28, 5 μg of Tbp-2 formulated with 500 μL of Alum on days 1, 14 and 28 or 5.0 μg of Tbp-2 incorporated into PLGpS microparticles on days 1 and 28. Sera obtained on days +40 and +56 were evaluated for the presence of anti-tbp-2 IgG antibodies using an enzyme-linked immunosorbent assay (ELISA).

FIG. 20 shows the serum IgG antibody subtype responses in mice immunized subcutaneously (S.C.) or orally (I.G.) following various immunization protocols by the recombinant protein rUrease from *Helicobacter pylori*. Groups of 8 mice were immunized on days 1, 28 and 56 with 250 μL of PBS pH 7.4, containing 10.0 μg (S.C.) or 40.0 μg (I.G.) of rUrease incorporated into PLGpS microparticles or 10.0 μg (S.C.) or 40.0 μg (I.G.) of rUrease formulated in the presence of DC-Chol, CT-X, PCPP or LT incorporated into PLGpS microparticles. Sera was obtained on day +85 and were evaluated for the presence of anti-rUrease IgG antibodies using an enzyme-linked immunosorbent assay (ELISA).

FIGS. 21a to b show the results of a protection study for the mice described in FIG. 20 one month after challenge on day 85. rUrease activity (for the mice immunized by subcutaneous or oral routes) was measured in ¼ of a whole stomach (antrum+corpus) 24 hours after the mice were killed.

DETAILED DESCRIPTION OF THE INVENTION

Figure 2:
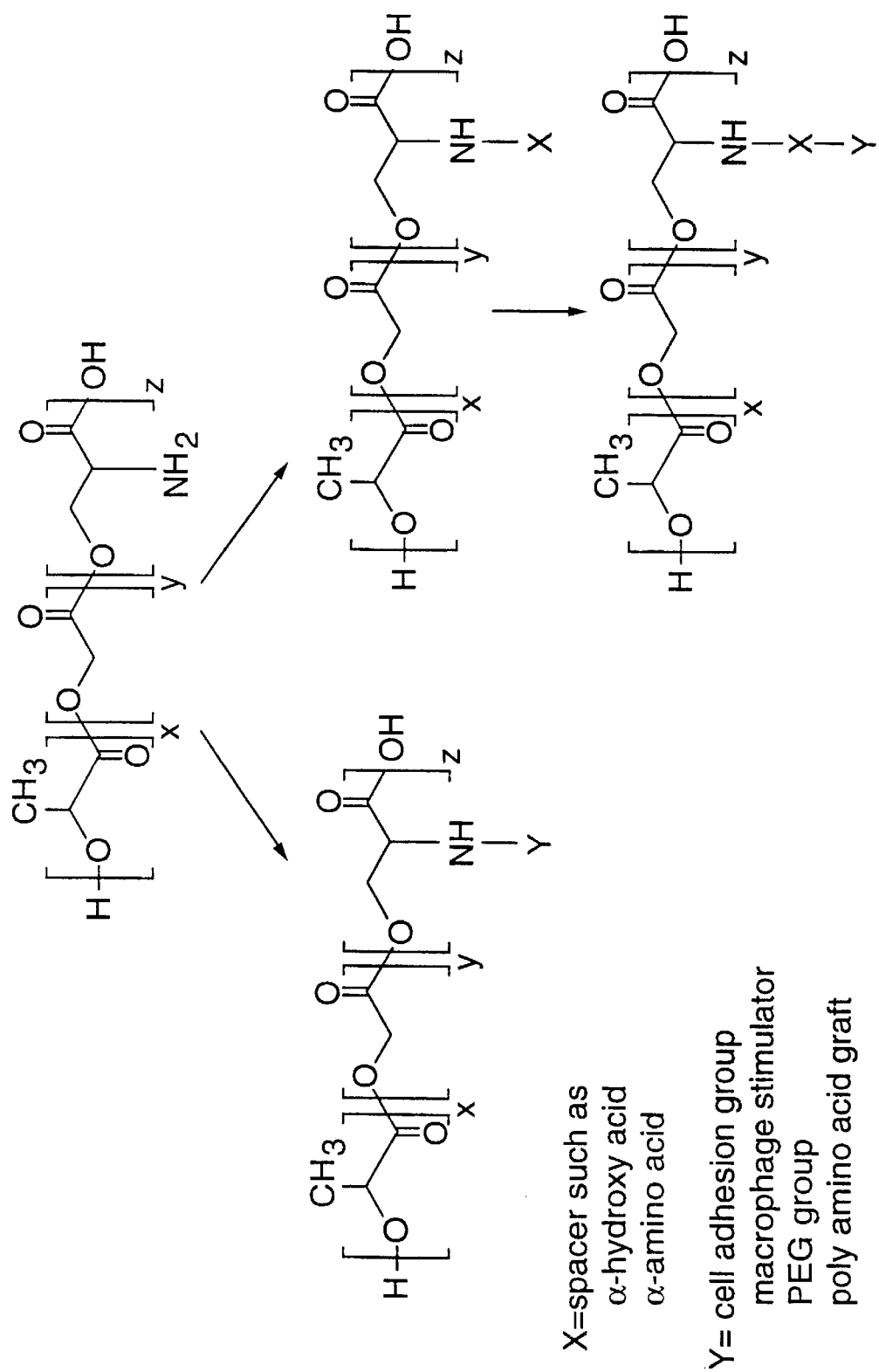
FIG. 2 is a schematic showing the attachment of biologically active moieties to polymer through the side chain of the a-amino acid sub-unit within the polymer. Representative targeting groups include poly-ethylene glycol (PEG) for water solubility and circulation, macrophage stimulators and cell bioadhesion groups. Spacer ligands derived from α-hydroxy acids or α-amino acids may be incorporated to facilitate attachment of the bioactive ligand.

The novel polymers of the present invention are biocompatible, degradable to benign metabolites which may be present in the body and may possess biologically active moieties, such as cell bioadhesion groups, macrophage stimulators, poly amino acids and polyethylene glycol coupled to the polymer via at least one spacer molecule selected from α-hydroxy acids and α-amino acids. As such, the novel polymers possess functionality.

Methods are also described for the synthesis of polymers having advantageous properties for processing into microparticles containing biologically active materials and for which chemical modification with biologically active targeting groups is possible.

In the preferred embodiments, the copolymers are produced by the polymerization of α-hydroxy acids with pseudo-α-amino acids and terpolymers produced by the polymerization of two α-hydroxy acids with pseudo-α-amino acids. The copolymer or terpolymer may then be derivatised with biologically active targeting ligands via the amino acid subunit by covalently coupling with the free amino group directly or subsequent to further derivatization with a suitable spacer ligand.

Amino Acid Monomer Synthesis

In general, an N-protected serine (or cysteine) is cyclized via a Mitsunobu reaction (ref. 5) to give a four membered lactone (or thiolactone).

This transformation gives rise to an ester (or thioester) linkage. It is important to have protection on the amine portion of the amino acid precursor that is compatible with the reaction conditions. Preferentially the carbobenzyloxy (CBZ or Z) group is used although other suitable functionalities, such as benzyl (Bn), para-methoxybenzyl (MeOBn), benzyloxymethoxy (BOM), tert-butyloxycarbonyl (t-BOC) or [9-fluorenylmethyl) oxy] carbonyl (FMOC) may be employed.

The synthesis of the N-Z-L-Serine β-Lactone monomer was based on a modified procedure from the literature (ref. 6).

Copolymerization Of α-Hydroxy Acid And Amino Acid Containing Monomers and Functionalization of Amino Acid Sidechains Two methods are applicable for copolymerization of α-hydroxy acid monomers. Polymerization via polycondensation or from the melt (bulk polymerization) are possible alternatives.

It has been long known that condensation polymerizations are problematic as relatively low molecular weight materials often result with competing side reactions commonly giving rise to unwanted byproducts (refs. 7 and 8).

However ring opening polymerization (ROP) of the cyclic dimers of α-hydroxy acids, such as glycolide and lactide, from the bulk phase was shown to proceed readily in the presence of a variety of catalysts to give polymers of high molecular weights with stannous octoate being preferred (refs. 9 to 15).

There are numerous methods for preparing poly(amino acids) (refs. 16, 17 and 18) or pseudopoly (amino acids) (refs. 6 and 19).

The noted biodegradable properties of poly-α-hydroxy acids (in particular those of 50:50 D,L-lactide and glycolide) and poly(amino acids) has resulted in increased efforts to develop methods for incorporating amino acids into the backbone of α-hydroxy acid polymers (refs. 20 to 25).

Advances have been made in producing copolyesteramides containing α-hydroxy acid sub-units, such as lactide or glycolide, and α-amino acid sub-units, such as glycine or lysine (refs. 22, 23 and 26).

The degradation rate of the biodegradable polymer and the release rates of encapsulated materials from homopolymers of glycolide, lactide or from copolymers of these materials has been shown to be strongly influenced by their molecular weight and structure, such as degree of crystallinity and relative hydrophobicity or hydrophilicity. Specifically, microspheres formulated from higher molecular weight polymers derived from α-hydroxy acids degrade over longer periods of time than lower molecular weight analogs. Similarly, highly crystalline materials erode at rates much slower than amorphous analogs. This is related to the accessibility of water to the hydrolytically unstable ester linkages (ref. 27).

It has been established that random amorphous copolymers composed of 50% D,L-lactide and 50% glycolide exhibit the most advanced degradation rates (refs. 2 and 3) with 50% by weight remaining after approximately 6 weeks, when immersed in PBS buffer (pH=7.4).

The copolyesteramides described above are semi-crystalline materials which may suffer from prolonged retention at the site of administration long after the encapsulated materials are fully released.

Since it would be advantageous to have a polymer that has degraded at or near the point when the encapsulated material has been fully released, we developed methods for randomly incorporating equal amounts of D,L-lactide and glycolide into a terpolymer which also contained pseudo-α-amino acid sub-units. A terpolymer of relatively moderate molecular weight was used to ensure the amorphous terpolymer would retain sufficient mechanical strength for processing into films and microparticles yet exhibit satisfactory polymer degradation and release rates for entrapped materials.

The N-protected-L-serine lactone contains an ester bond which may be polymerized via transesterification catalysts (ref. 6). Additionally it has been shown that six-membered ring lactones, such as lactide and glycolide, can be copolymerized with four-membered ring propiolactones by use of insertion/coordination type catalysts/initiators (ref. 13). It was expected that efficient transesterification catalysts, such as those derived from Sn reagents, would be required if relatively sufficient reactivity of all monomer units was to be achieved.

We used the copolymerization of glycolide, D,L-lactide and N-Z-L-serine lactone mediated by stannous octoate. Deprotection of the CBZ group of the copolymer or terpolymer can be achieved by various methods. Solid phase catalytic reduction or acid catalysis (ref. 27) are two possibilities (FIG. 1).

The resultant copolymer or terpolymer can be further elaborated with targeting moieties such as cell adhesion epitopes, poly ethylene glycol (PEG) ligands for circulation, macrophage stimulators and poly amino acid grafts as depicted in FIG. 2. A spacer unit may be incorporated, for example, an α-hydroxy acid or a pseudo-α-amino acid unit, and may be readily derivatised with the appropriate targeting units. The polymer so formed has a molecular weight of from about 5,000 to about 40,000 daltons.

Microparticle Formation

The term "microparticle" as used herein refers to any particulate carrier greater than 1 micron in size which is used for the delivery of biologically active materials. The term "microsphere" as used herein refers to a microparticle containing one or more active ingredients (e.g. antigens, adjuvants, plasmid DNA).

Figure 3:
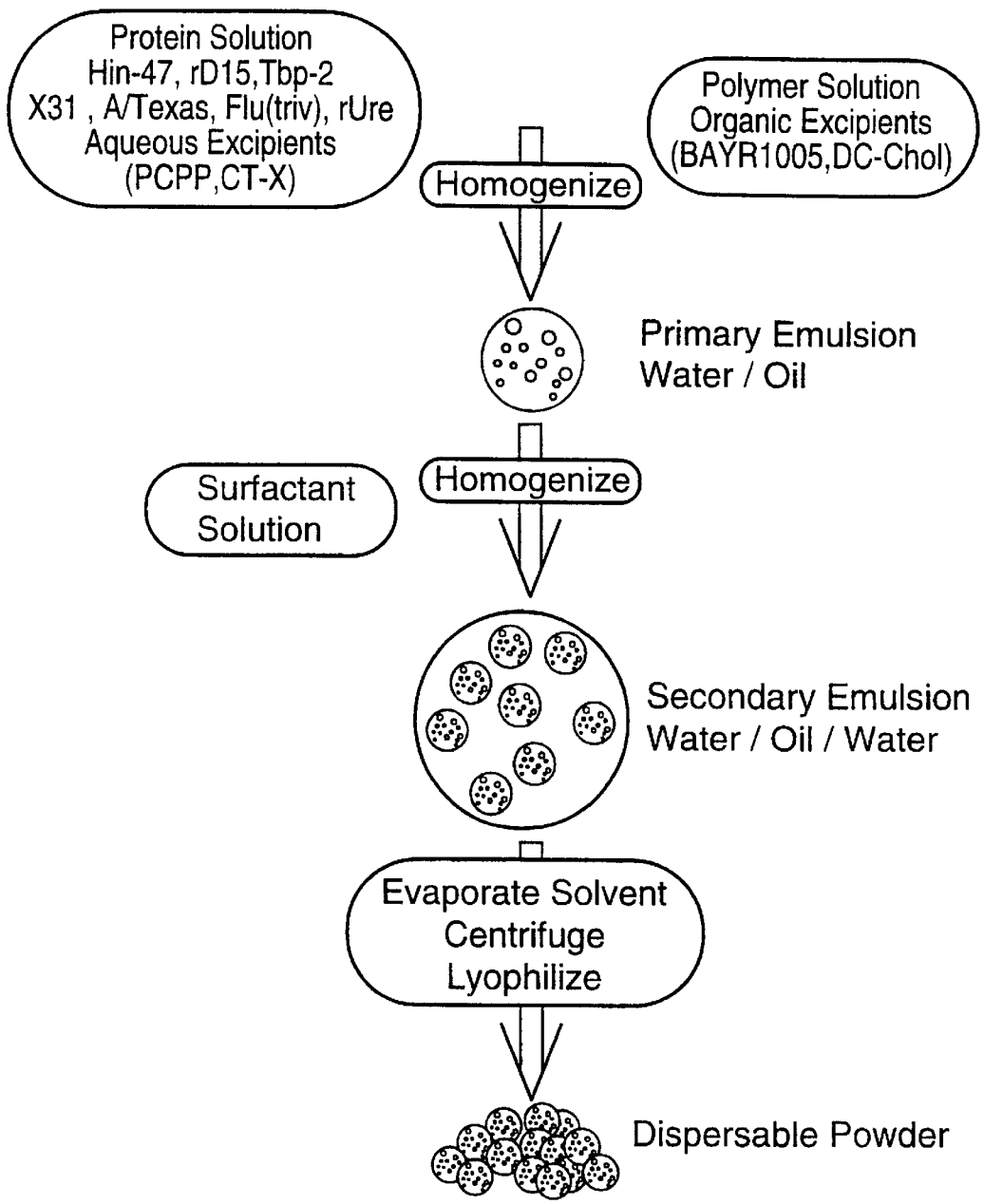
FIG. 3 is a schematic detailing the process used to produce microparticles in accordance with one embodiment of the invention. In this figure, Hin-47 is a non-proteolytic recombinant protein analog derived from *Haemophilus influenzae* (as described in U.S. Pat. No. 5,506,139), Flu X31 is influenza strain X31 or A-Texas, rD-15 is recombinant protein derived from *Haemophilus influenzae* (as described in WO 94/12641), PVA=poly vinyl alcohol. Flu (tri) is trivalent flu, Tbp2 is *Moraxella catarrhalis transferrin binding protein* 2 and rUrease is recombinant *Helicobacter pylori* urease.

A flow diagram illustrating the process of microparticle formation as described herein is shown in FIG. 3. In general, the copolymer (PLG, PLGpZS or PLGpS) is solubilized solely or with additional excipients present in a compatible solvent, such as dichloromethane, ethyl acetate, acetone or mixtures thereof. Excipients included in the formulation, such as sucrose, mannose, trehalose or gelatin, serve as cryoprotectants or lyoprotectants. Other materials possessing known adjuvancy, such as BAY R1-005 (BAY) (ref. 29) or tripalmitoyl cysteine (TPC) (ref. 30) or 3b[N-(N',N'-dimethylaminoethane)-carbamoyl] cholesterol (DC-Chol) (ref. 31) may be included during formulation.

A 1% to 2% copolymer solution of total volume 12 mL is preferably prepared. To this solution is added 800 μL of phosphate buffered saline (PBS) or 800 μL of antigen solution (concentration typically from 1 to 2 mg/mL) in PBS or other stabilizing buffers which may contain additional excipients. Other material possessing known adjuvancy, such as poly[di(carboxylatophenoxy)-phosphazene] sodium salt, (Virus Research Institute, Cambridge Mass.) (PCPP) or cholera toxin or subunits thereof may be included during formulation. This mixture is then homogenized to form a water in oil emulsion. Once formed, this mixture is dispersed into 100 mL of a 0.5% to 10.0% aqueous solution containing non-ionic emulsion stabilizers, such as poly vinyl alcohol (PVA), methyl cellulose or Triton X-100. This mixture is immediately homogenized to form a water in oil in water double emulsion. The average size and polydispersity of the resultant droplets can be conveniently measured through use of the Coulter LS-100 light scattering detector. Typical size distributions when PBS or Antigen/PBS mixtures are encapsulated range from 1 to 20 microns (with the majority less than 10 microns in size). The solvent is then slowly removed via evaporation with gentle warming to harden the incipient microspheres. Once the solvent is removed the mixture is centrifuged to collect the microspheres and repeatedly washed with deionized water to ensure complete removal of residual emulsion stabilizers. The microspheres are then frozen in a dry ice/acetone bath and lyophilized overnight to yield a white freely flowing powder of microspheres (typically 1.0 to 12 microns in size as determined by light scattering measurements and directly verified via scanning electron micrography).

The particle generally comprise a polymeric matrix having a particle size of about 1 to about 50 $\mu$M which comprises a polymer having the biologically-active material entrapped therein, with or without an adjuvant co-entrapped therein. The quantity of biologically-active material and adjuvant which may be incorporated into the polymeric matrix may vary widely and may comprise up to about 50 wt % of the total particle mass.

It is clearly apparent to one skilled in the art, that the various embodiments of the present invention have many applications in the fields of medicine and in particular vaccination, diagnosis and treatment of infections with pathogens including bacteria and viruses. A further non-limiting discussion of such uses is presented below.

Vaccine Preparation

In an embodiment, immunogenic compositions, suitable to be used as, for example, vaccines, may be prepared from microparticles as disclosed herein. The immunogenic composition containing a biologically active immunogenic material can elicit an immune response by the host to which it has been administered including the production of antibodies by the host.

The immunogenic composition may be prepared as injectables, as liquid solutions or emulsions. The microparticles may be mixed with physiologically acceptable excipients which are compatible with the microparticles. These may include, water, saline, dextrose, glycerol, ethanol and combinations thereof. The vaccine may further contain additional substances such as wetting or emulsifying agents, pH buffering agents, or adjuvants to further enhance the effectiveness of the vaccines. Vaccines may be administered parenterally, by injection subcutaneously or intramuscularly.

Alternatively, the immunogenic compositions comprising microparticles formed according to the present invention may be delivered in a manner to elicit an immune response at mucosal surfaces. Thus, the immunogenic composition may be administered to mucosal surfaces by nasal, oral (intragastric), buccal or rectal routes. Oral formulations may include normally employed incipients, such as pharmaceutical grades of saccharin, cellulose and magnesium carbonate.

These compositions may take the form of solutions, suspensions, tablets, pills, capsules, sustained release formulations or powders. In order to protect the microparticles and the encapsulated material contained within the core of the microparticle or which is physically mixed with the microparticles, from gastric acidity when administered by the oral route, an acidic neutralizing preparation (such as a sodium bicarbonate preparation) is advantageously administered before, concomitant with or directly after administration of the microparticles.

The vaccines are administered in a manner compatible with the dosage formulation, and in such amount as to be therapeutically effective, protective and immunogenic. The quantity to be administered depends on the subject to be treated, including, for example, the capacity of the subject's immune system to synthesize antibodies, and if needed, to produce a cell-mediated immune response. Precise amounts of microparticle and material having biological activity required to be administered depend on the judgement of the practitioner. However, suitable dosage ranges are readily determinable by one skilled in the art and may be of the order of micrograms to milligrams. Suitable regimes for initial administration and booster doses are also variable, but may include an initial administration followed by subsequent administrations. The dosage of the vaccine may also depend on the route of administration and thus vary from one host to another.

The polymers of the present invention as applied to vaccine formulations, are also useful for new vaccine strategies, such as with the use of DNA or antisense RNA. As microparticle carriers, the polymers of the present invention can be prepared to contain DNA coding for a gene or genes for an antigenic portion of a virus such as the core protein or the envelope protein. As the DNA is released from the carrier, the host cells take up the foreign DNA, express the gene of interest and make the corresponding viral protein inside the cell. Advantageously, the viral protein enters the cells major histocompatibility complex pathway which evokes cell-mediated immunity. Standard vaccine antigens in comparison, are taken up into cells and processed through the MHC class II system which stimulates antibody responses.

The DNA may be in the form of naked DNA which is free of all associated proteins and which does not require a complex vector system. The desired gene may be inserted into a vector, such as a plasmid, encapsulated within the microparticle herein described, and injected into the tissues of a mammal which expresses the gene product and evokes an immune response.

Antisense oligonucleotides can also be used in conjunction with the polymers of the present invention. Nucleic acid sequences may be designed to bind to a specific corresponding mRNA sequence for a known protein to inhibit the production of the protein. The microparticles described herein, can be used to deliver such antisense nucleotides (oligonucleotides or expressed nucleotides) as a therapeutic strategy for the treatment of various immunological diseases as well as hypertension, cardiovascular disease and cancer.

The slow-release characteristic of the polymer microparticles developed herein also has use in the field of pharmacology where the microparticles can be used to deliver pharmacological agents in a slow and continual manner. A wide range of drugs, such as anti-hypertensives, analgesics, steroids and antibiotics, can be used in accordance with the present invention to provide a slow release drug delivery system.

The polymer in the form of a film having a biological agent entrapped or physically admixed thereto, may also have use as a coating for surgical implants and devices. For example, the polymer as a film having antibiotic incorporated therein can be used to coat surgically implanted catheters in order to provide continual slow-release of antibiotics to combat infection.

The microparticle carrier may also be useful as a diagnostic agent. Together with the appropriate antibody, imaging agents can be incorporated with the microparticles. In this manner diseased tissues can be targeted and imaged in order to identify or monitor the clinical course of a disease.

The polymers, as microparticles, also have use in diagnostic kits when used in conjunction with appropriate antibodies.

EXAMPLES

The above disclosure generally describes the present invention. A more complete understanding can be obtained by reference to the following specific Examples. These Examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitations.

Methods of chemistry, organic chemistry, polymer chemistry, protein biochemistry and immunology used but not explicitly described in this disclosure and these Examples are amply reported in the scientific literature and are well within the ability of those skilled in the art.

Example 1

This Example illustrates the preparation of N-Z-L-Serine β-Lactone.

The preparation of this cyclic N-protected amino acid lactone was based on a modified procedure in which an N-protected-α-amino acid is reacted to yield cyclized pseudo-α-amino acid monomer (ref. 6). All glassware was pre-dried overnight in an oven set at 120° C. Prior to use it was cooled in a vacuum desiccator and purged under a stream of dry nitrogen for 10 minutes.

To a 1 L three necked round bottomed flask under nitrogen was added triphenylphosphine (TPP; Aldrich;

7.87 mL; 50 mmol; FW: 174.16). To this was added 200 mL of anhydrous acetonitrile ($CH_3CN$; Aldrich): anhydrous tetrahydrofuran (THF; Aldrich) solution (volume ratio 85:15) via syringe and stirred until the solid TPP was dissolved. To this solution diethyl azodicarboxylate (DEAD; Aldrich; 7.87 mL; 50 mmol; FW: 262.29) was added via syringe and the solution stirred at room temperature for 30 minutes. The solution was then cooled to about −45° C. to −48° C. by immersing the reaction vessel in an acetonitrile/dry ice bath. Once the internal temperature of the solution reached about −45° C., a solution of N-Carbobenzyloxy-L-Serine (N-CBZ-L-Serine; Sigma; 11.94 g; 49.8 mmol; FW: 239.2) in 200 mL of anhydrous $CH_3CN$:THF (volume ratio 85:15) was slowly added via dropping funnel over a period of 1 hour. The temperature of the solution was maintained at about −45° C. during the addition and allowed to slowly warm to room temperature once the addition was complete with continuous stirring overnight. This reaction results in the formation of an ester bond between the serine hydroxyl side chain and the carboxylic acid in the presence of the CBZ protected α-amino group. Upon completion of the reaction the solvents were removed via evaporation (35° C. to 45° C.). This yields a yellow oil/slurry (~35 g). To this slurry was added 50 mL of dichloromethane:ethyl acetate (volume ratio 85:15) solution which results in the precipitation of 1,2-dicarbethoxyhydrazine byproduct. This material was removed by filtration under vacuum followed by solvent removal via evaporation. The above procedure can be repeated to further remove residual byproducts. The waxy solid crude material was then purified via silica gel column chromatography with eluent 85:15 dichloromethane:ethyl acetate as solvent. The product serine lactone can be identified via thin layer chromatography as this material has an $R_f$ of 0.75 on silica plates eluted with 85:15 dichloromethane:ethyl acetate when stained with a 1 M $H_2SO_4$ solution and is also UV visible. The product was recrystallized from ethyl acetate:hexane (~1L), filtered and dried in vacuo.

A clean white solid is obtained in 40% yield after recrystallization with a melting point (Tm=133–134° C.) and all other physical parameters (NMR, IR, mass spectroscopy, elemental analysis) conforming to that previously demonstrated (ref. 6).

Example 2

This Example illustrates the preparation of the copolymer poly-D,L-Lactide-co-Glycolide-co-pseudo-Z-Serine Ester (PLGpZS) as shown in FIG. 1.

Glassware was pre-dried overnight. Prior to use it was cooled in a vacuum desiccator. Additionally the polymerization vessel (glass ampule) must be siliconized (SurfaSil; Pierce; 2% solution in toluene) and all transfer reactions and additions of reagents and monomers to polymerization vessel must be conducted in a glove box maintained under a dry nitrogen environment.

Prior to polymerization the D,L-lactide (2,6-dimethyl-1, 4-dioxane-2,5-dione; Aldrich; FW: 144.13) and glycolide (Boehringer Ingelheim; FW: 116.096) was recrystallized from anhydrous ethyl acetate in the glove box and dried in vacuo for about 2 days. Once fully dried the monomers can be stored in the glove box with the freshly recrystallized serine lactone (stored at 0° C.) of Example 1 brought directly into the glove box. All monomers and catalyst/initiators were weighed and transferred to glass ampules within the glove box.

The total combined mass of monomer transferred to the ampoule typically ranges from 1 g to 5 g with the molar ratio of D,L-lactide:glycolide:serine lactone ranging from 42.5:42.5:15.0 to 49.0:49.0:2.0. A molar ratio of D,L-lactide:glycolide:serine lactone of 47.5:47.5:5.0 was used in the preferred embodiment. A stock solution of catalyst (stannous 2-ethylhexanoate ($Sn(Oct)_2$; Sigma; FW 405.1, 1.25 g/mL) in anhydrous chloroform (Aldrich) was prepared in the glove box and added via microsyringe to the glass ampule (molar ratio of catalyst to monomer=1/1000). A stir bar was also placed in the ampule. A greased ground glass joint valve was placed on the ampule to preserve the inert environment during removal from the glove box. The ampule was then directly placed on a vacuum line with slow removal of chloroform by evaporation. The ampules were then placed in an oil bath at ca. 120° C. to bring all reagents into the melt followed by flame sealing and placement in a thermoregulated oven at 120° C. for 28 hours. After reaction the ampules are quenched by placing in liquid nitrogen and stored at −20° C. until further work up. The ampule was cracked and crude polymer recovered by dissolving in chloroform. The solvent was removed by evaporation and crude polymer dried in vacuo to give an amber crystalline material (yield 80% to 90%).

The polymer was purified by dissolving in chloroform, filtering off insoluble material and precipitating into hexane (Aldrich). The polymer was recovered by filtration and this procedure was repeated to ensure the complete removal of unreacted monomer. The polymer was dried in vacuo for about 2 days to give a clean white powder in 30% to 35% overall yield after second precipitation. The molecular weight of this material was dependent on reaction time with typical values of Mw=17,000–22,000, Mn=6,500–8,000. Differential scanning calorimetry (DSC) analysis indicates a single transition indicative of a random amorphous polymer. Glass transitions (Tg) range from 39° C. to 43° C. dependent on the molecular weight of the material obtained. The serine content of the polymer was determined by amino acid analysis (AAA) diagnostic for the phenylthio isocyanate serine derivative obtained by hydrolysis of the polymer, $^1$H NMR (integration of aromatic residues of the CBZ protecting group on serine relative to the glycolide and D,L-lactide sub-units) and elemental analysis (nitrogen present only in the side chain of serine). The AAA analysis typically indicated 1.7% to 2.1% serine content with the $^1$H NMR analysis indicating 2.0% to 2.5% and the elemental analysis indicating 2.4% to 3.4% serine respectively. IR analysis of the polymer was diagnostic for the presence of ester, carbamate and hydroxyl groups.

$^1$H NMR also allowed for the determination of the relative incorporation efficiencies of all monomer components under the stated reaction conditions. Typical ratios of D,L-lactide:glycolide:Z-serine found in purified polymer are reproducibly 52.0% to 54.0% D,L-lactide, 41.0% to 43.5% glycolide and 2.0% to 2.5% Z-serine respectively.

$^1$H NMR and $^{13}$C NMR signal intensities for resonances unique to glycolide or D,L-lactide are well resolved from each other and sensitive to sequence effects. From the observed patterns a random sequence distribution is supported.

Example 3

This Example illustrates the preparation of the copolymer poly-D,L-Lactide-co-Glycolide-co-pseudo-Serine Ester (PLGpS) as shown in FIG. 1.

All glassware was pre-dried overnight. Prior to use it was cooled in a vacuum desiccator and purged under a stream of dry nitrogen for 10 minutes. All reactions were conducted under inert atmosphere of dry nitrogen.

To a 2 necked 100 mL round bottomed flask equipped with a stir bar was placed 400 mg of polymer (PLGpZS) To this was added a 10 mL solution of 30% hydrogen bromide in acetic acid (Aldrich; FW: 80.92) which was sufficient for slurry formation. The slurry was stirred for 30 to 45 minutes and quenched by dropwise addition of anhydrous diethyl ether (Aldrich) followed by anhydrous methanol (Aldrich). This results in polymer precipitation which was then isolated by vacuum filtration. The crude polymer precipitate was washed with diethyl ether and reprecipitated from chloroform:hexane. The purified polymer was dried in vacuo for about 2 days to give a clean white powder in 50% to 60% overall yield. The molecular weight ranged from Mw=15, 000–18,000, Mn=5,000–6,500. The rate of deprotection of the CBZ group is faster than the competitive cleavage of the ester backbone with HBr/Acetic acid. However, under these conditions there is broadening of the molecular weight distribution and reduction in the molecular weight of the product as a consequence of using this reagent. This trend can be reduced by conducting the reaction for shorter time intervals or eliminated by removing the protecting group via hydrogenation using hydrogen in the presence of palladium on charcoal. DSC analysis indicates a single transition indicative of a random amorphous polymer. Glass transitions (Tg) range from 42° C. to 45° C. depending on the molecular weight of the material obtained. The serine content of the polymer was determined by amino acid analysis (AAA) diagnostic for the phenylthio isocyanate serine derivative obtained by hydrolysis of the polymer and elemental analysis (nitrogen present only in the side chain of serine) The AAA analysis typically indicated 1.4% to 1.7% serine content and the elemental analysis indicating 2.0% to 2.7% serine respectively. IR analysis of the polymer was diagnostic for the presence of ester, amine and hydroxyl groups.

$^1$H NMR for residual protected polymer indicated that greater than 90% of the N-carbobenzyloxy groups were successfully removed. With shorter reaction times the extent of deprotection is concomitantly reduced. Typical ratios of D,L-lactide:glycolide:Z-serine:serine found in purified polymer are reproducibly 53.0% to 55.0% D,L-lactide, 40.0% to 43.0% glycolide, 0.15% to 0.25% Z-serine and 1.7% to 2.1% serine respectively.

Example 4

This Example illustrates the production of a film from the copolymers synthesized in Examples 2 and 3.

To produce the film, 50 mg of poly-D,L-Lactide-co-Glycolide (PLG) (Mw=31,000), poly-D,L-Lactide-co-Glycolide-co-pseudo-Z-Serine Ester (PLGpZS) (Mw=20,000) or poly-D, L-Lactide-co-Glycolide-co-pseudo-Serine Ester (PLGpS) (Mw=19,000) was weighed out and placed in a 10 mL beaker. Anhydrous chloroform (1 mL) was added to dissolve the copolymer. This solution was filtered and added dropwise to a microscope slide placed in a petri dish. The petri dish was then covered with a 250 mL beaker to ensure slow evaporation over 48 hours. The resultant films were translucent and contact angle measurements performed using a goniometer gave average values of 75° for PLG, 75° for PLGpZS and 68.2° for PLGpS respectively. Thus the PLG and PLGpZS copolymers are of comparable hydrophobicity with the PLGpS copolymer proving to be slightly more hydrophilic and of higher surface energy.

Example 5

This Example illustrates the process of microparticle formation encapsulating PBS or antigen/PBS (microsphere formation).

A flow diagram illustrating the process of microparticle formation as described herein is shown in FIG. 3.

Figure 4C:
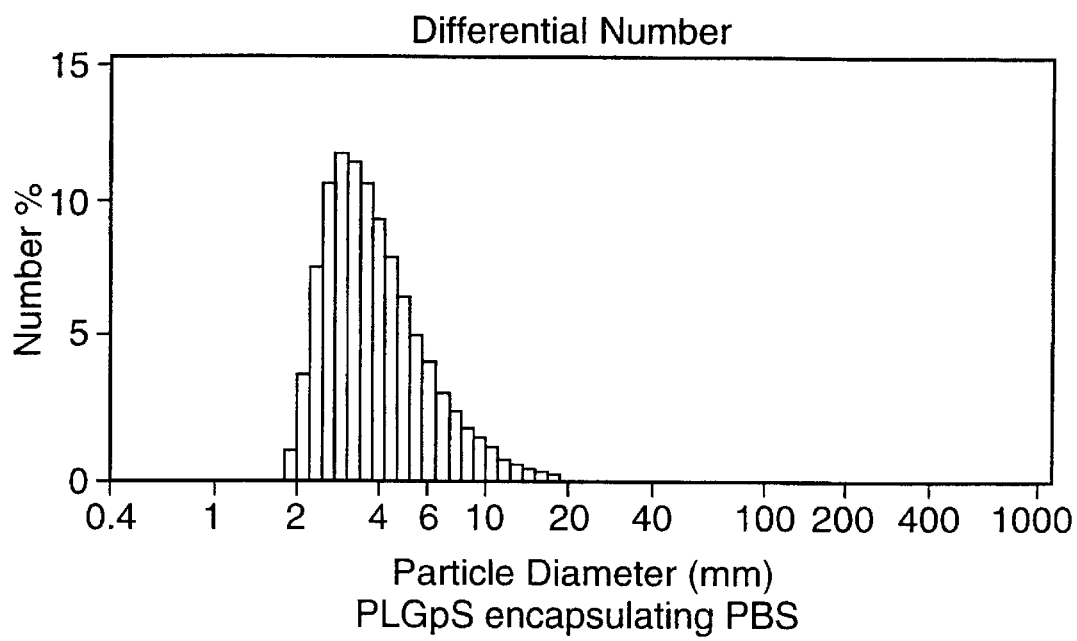
FIG. 4 shows a typical size distribution for poly-D,L-lactide-co-glycolide-co-pseudo-(Z)-serine ester (PLGpZS) and poly-D,L-lactide-co-glycolide-co-pseudo-serine ester (PLGpS) microparticles when prepared in the presence of PBS or a typical protein (non-proteolytic Hin-47 analog) as determined by laser diffraction measurements.
Figure 4D:
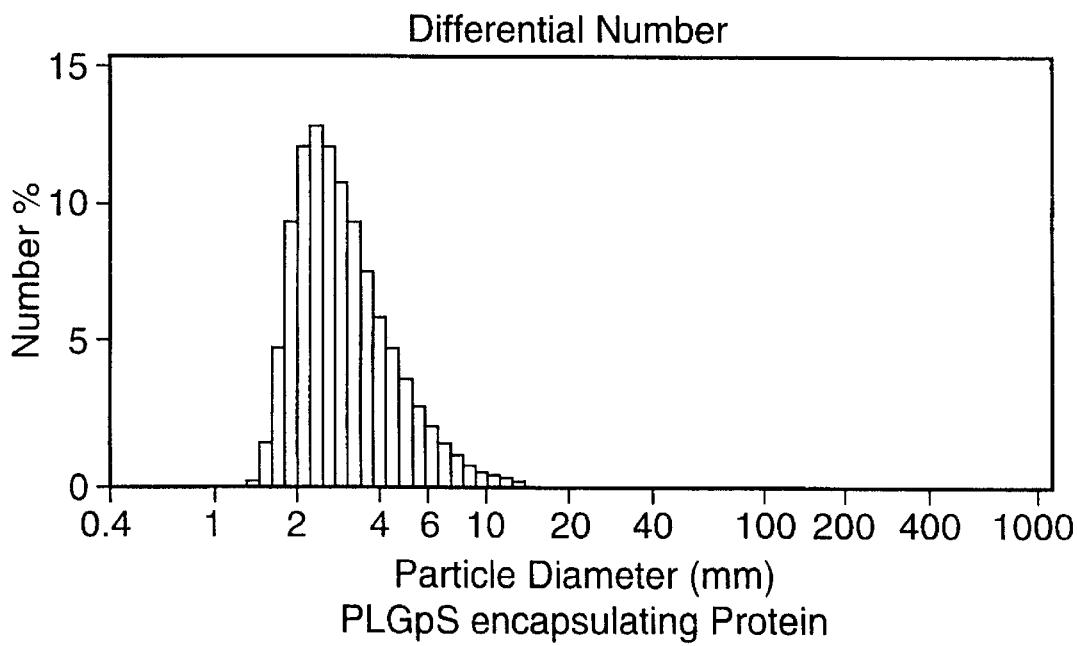
Figure 5A:
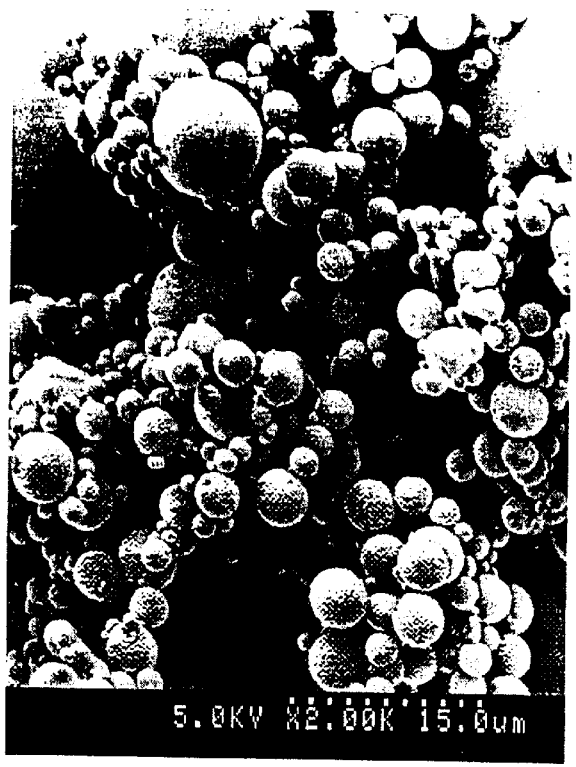
FIG. 5 shows a scanning electron micrograph of microparticles prepared from poly-D,L-lactide-co-glycolide-co-pseudo-(Z)-serine ester (PLGpZS) and poly-D,L-lactide-co-glycolide-co-pseudo-serine ester (PLGpS) in the presence of phosphate buffered saline(PBS).
Figure 5B:
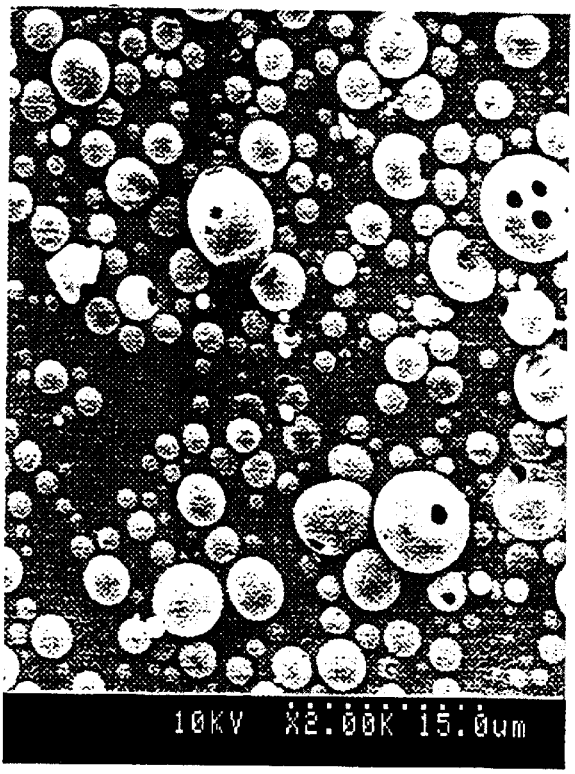
Figure 6A:
FIG. 6 shows a scanning electron micrograph of microparticles prepared from poly-D,L-lactide-co-glycolide-co-pseudo-(Z)-serine ester (PLGpZS) and poly-D,L-lactide-co-glycolide-co-pseudo-serine ester (PLGpS) in the presence of a typical antigen/PBS mixture such as Hin-47/PBS.
Figure 6B:
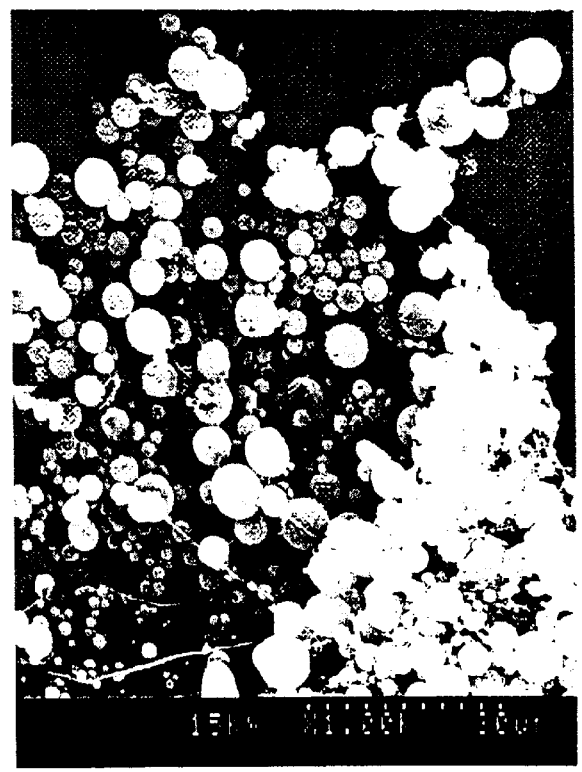

Specifically, 100 mg of copolymer was added to 12 mL of dichloromethane. To this was added 800 μL of phosphate buffered saline (PBS) solution or 800 μL of non-proteolytic Hin-47 analog (concentration typically from 1 to 2 mg/mL) in PBS. This mixture was then homogenized (20 seconds at 6,000 rpm). Once formed this mixture was dispersed into 100 mL of a 1.0% aqueous solution of poly vinyl alcohol (PVA) and immediately homogenized (40 seconds at 8,000 rpm) to form a water in oil in water double emulsion. Typical size distributions when PBS or a typical antigen (Hin-47/PBS) is used as encapsulant are depicted in FIG. 4. Polydisperse microparticles (with the majority less than 10 microns in size) were formed under these conditions. The solvent was then slowly removed via evaporation and the microspheres collected by centrifugation. The particles were washed (5×) with deionized water and then frozen in a dry ice/acetone bath and lyophilized overnight to yield a white freely flowing powder of microspheres (typically 1.5 to 10 microns in size as determined by light scattering measurements and directly verified via scanning electron micrography). A representative scanning electron micrograph for PLGpZS or PLGpS microspheres encapsulating PBS is shown in FIG. 5. A representative scanning electron micrograph for PLGpZS or PLGpS microspheres encapsulating a typical antigen (non-proteolytic Hin-47 analog) in PBS is shown in FIG. 6.

By the method stated above microparticles containing several different antigen(s) and/or antigen(s)+adjuvant have been prepared (see Tables 1 and 5).

Example 6

This Example illustrates the microparticle core loading efficiency and antigen epitope recovery from such microparticles.

Two variations of the same method were employed to determine the antigen content or "core loading" of the microparticles isolated. Amino acid analysis was performed on the hydrosylates of microparticles obtained by either acid hydrolysis (6M HCl) of the solid particles or by base/SDS hydrolysis (0.1N NaOH/1% SDS) followed by neutralization with 0.1N HCl. Alternatively, the solid microspheres can be dissolved in DMSO a compatible solvent solubilizing both polymer and protein and amino acid analysis performed directly on the lyophilized sample. The acid or base mediated hydrolysis proved to be the preferred method giving the most reproducible results (+/−5%). Where available a validated Enzyme Linked Immunosorbant Assay (ELISA) polyclonal assay was performed on the hydrosylates to determine the epitope equivalence.

Specifically, for the quantitation of non-proteolytic Hin-47 analog antigen by ELISA the non-proteolytic Hin-47 analog antigen was captured on affinity purified guinea pig anti-Hin47 coated microtitre wells (Add 50 $\mu$L of a 2 $\mu$g/mL solution of non-proteolytic Hin-47 analog antigen per well), which have been blocked with 5% skim milk in PBS. The antigen present was detected by an affinity purified rabbit anti-Hin-47 followed by horse radish peroxidase F(abs)2, donkey anti-rabbit IgG. To develop the color of this reaction 100 $\mu$L of the substrate $H_2O_2$ (9 parts) in the presence of tetramethylbenzidine (TMB) (1 part), and the reaction progress terminated by addition of 50 $\mu$L of a 2M sulphuric acid solution to each well. The intensity of the color (read at 450 nm) was directly proportional to the amount of non-proteolytic Hin-47 analog in the well. The concentration of non-proteolytic Hin-47 analog in each test sample was derived by extrapolation from a standard curve which was obtained by multiple dilutions of a reference sample. All samples were analyzed in duplicate. The amino acid analysis for core loading and Hin-47 specific polyclonal ELISA analysis of epitope recovery for microparticles encapsulating non-proteolytic Hin-47 analog or non-proteolytic Hin-47 analog plus BAY R1-005 within PLG, PLGpZS and PLGpS copolymers is shown in Table 2. The core loadings for microparticles prepared solely from Hin-47 range from 20% to 43% with from 10% to 31% of the epitope preserved during formulation. The core loadings for microparticles prepared from non-proteolytic Hin-47 analog in the presence of BAY R1-005 range from 26% to 59% (an absolute increase of 6% to 16%) with from 20% to 39% (an absolute increase of 4% to 18%) of the epitope preserved during formulation. Thus formulation in the presence of BAY R1-005 concomitantly increases the loading efficiency and serves to protect the epitope.

The amino acid analysis of core loading for microparticles encapsulating rD-15 within PLG, PLGpZS and PLGpS copolymers is shown in Table 3. Core loadings ranging from 39% to 44% were obtained. This protein was membrane derived and thus more hydrophobic than the non-proteolytic Hin-47 analog of the previous example. Increased encapsulation efficiencies relative to non-proteolytic Hin-47 analog of Example 10 were routinely observed when using this antigen.

The amino acid analysis for core loading and epitope recovery for microparticles encapsulating a cocktail of non-proteolytic Hin-47 analog and rD-15 (1:1 cocktail) within PLG, PLGpZS and PLGpS copolymers is shown in Table 3. It was expected that coencapsulation of non-proteolytic Hin-47 analog in the presence of rD-15 would result in higher overall loading efficiencies. Core loadings ranging from 35% to 62% were obtained with from 8% to 26% of the non-proteolytic Hin-47 analog epitope preserved during formulation. The overall loading efficiency of the more hydrophilic component (non-proteolytic Hin-47 analog) was increased by coencapsulation with rD-15 when formulated with PLGpZS or PLGpS copolymers. This effect was not observed when PLG was used. Irrespective of copolymer formulation similar non-proteolytic Hin-47 analog epitope recovery as compared with Example 10 was obtained.

The amino acid analysis of core loading for microparticles encapsulating Flu X-31 or Flu X-31 and BAY R1-005 within PLG, PLGpZS and PLGpS copolymers is shown in Table 4. Core loadings ranging from 26% to 40% were obtained with Flu X-31 and for Flu X-31 in the resence of BAY R1-005 core loadings ranging from 31% to 53% were obtained. Thus, an absolute increase of 5% to 13% was obtained when formulating in the presence of BAY R1-005. The only exception was the formulation of Flu X-31 with BAY R1-005 and PLGpS where an absolute decrease of 9% was observed.

A core loading of 21% for PLGpS microparticles encapsulating Flu A-Texas was obtained. For PLGpS microparticles encapsulating Flu A-Texas in the presence of BAY R1-005 a core loading of 32% was obtained.

When a different strain of Flu was employed (A-Texas) with BAY R1-005 and PLGpS copolymer the tendency to increase the encapsulation efficiency was once again observed. When formulating PLGpS with Flu A-Texas in the presence of BAY R1-005 an absolute increase of 11% was obtained. This suggests that the formulation for PLGpS and proteins in the presence of BAY R1-005 must be optimized in each case. As in Example 10, the addition of the coadjuvant BAY R1-005 has resulted in higher loading efficiencies.

The amino acid analysis of core loading for microparticles encapsulating Flu (trivalent) vaccine or Flu (trivalent) vaccine and BAY R1-005, DC-Chol or PCPP within PLGpS copolymers is shown in Table 6. Excellent core loading efficiencies ranging from 72% to 104% were obtained using the procedure of Example 5. The improvement in encapsulation efficiencies is a general result observed when the optimum concentration of protein is used to form the primary emulsion. In this case, the optimum concentration was experimentally determined to be about 0.5 mg/mL.

The amino acid analysis for core loading and rUrease specific polyclonal ELISA analysis of epitope recovery for microparticles encapsulating rUrease or rUrease plus DC-Chol, PCPP or CT-X within copolymers is shown in Table 7. Epitope recovery is defined as the difference between the total protein obtained by amino acid analysis and total protein obtained by polyclonal ELISA expressed as a percentage. The core loadings for microparticles prepared solely from rUrease is about 46% with about 72% of the epitope recovered during formulation. Similarly the core loadings for microparticles prepared from rUrease in the presence of DC-Chol is about 44% with about 69% epitope recovered. Slightly higher total protein was determined for microparticles prepared from rUrease in the presence of PCPP. A core loading of 67% and epitope recovery of about 55% was found for this combination. For the rUrease/CT-X combination, the total core loading for rUrease could not be estimated by amino acid analysis since both rUrease and CT-X contribute to this value. A polyclonal ELISA assay for CT-X was developed and microparticle hydrosylates assayed for total rUrease and CT-X separately. An epitope recovery of 53% was found for rUrease and 59% for CT-X respectively. SDS-PAGE and Western blots performed on these microparticle hydrosylates confirmed the presence of non-degraded rUrease and CT-X.

Suitable controls were performed to ensure that the polyclonal ELISA assay for rUrease was unaffected by additives, such as DC-Chol and PCPP. In the case of PCPP, the assay was often problematic and variable. No similar problem was found when assaying rUrease in the presence of DC-Chol.

Example 7

This Example illustrates the in vitro release rates and total cumulative % recovery of protein for a model antigen (non-proteolytic Hin-47 analog) encapsulated within PLG (used as a control for comparison purposes) and synthesized copolymers PLGpZS and PLGpS.

The PLG formulated into microspheres containing antigen was determined to be of molecular weight; Mw=26,000 with a 50:50 ratio of D,L-Lactide:Glycolide. This material is of similar constitution and molecular weight to that obtained for copolymers PLGpZS and PLGpS of Examples 2 and 3. In a typical experiment, 14 mg of microspheres (core loading of non-proteolytic Hin-47 analog for PLG=2.8 μg/mg, PLGpZS=5.7 μg/mg and PLGpS=2.5 μg/mg as determined by amino acid analysis of the microsphere hydrosylates) was placed in a 2 mL eppendorf tube to which was added 1.0 mL of PBS (pH=7.4). The tube was then placed in a thermoregulated oven maintained at 37° C. without agitation. At various time intervals the PBS solution was extracted and analyzed for total protein via amino acid analysis. After each extraction the PBS solution was replaced with continued sampling to a maximum of 90 days. In control experiments, the majority of the microspheres (>80% by weight) prepared from PLG or PLGpS copolymers were consumed by day 45. The degradation of microspheres formulated from PLGpZS copolymers was observed to be somewhat slower requiring 60 days to erode to essentially the same extent.

Similar antigen release trends were observed with each group of microparticles wherein small amounts of protein were released over the first few days. This diminished to near undetectable limits up to day 14 whereafter the protein release rate steadily increased to a maximum at about day 30. Subsequent to this time, the release of protein fell to levels again approaching the limit of detection. The total % cumulative recovery of protein from these samples ranged from 40% to 65% relative to the respective core loadings of each group of microspheres.

Figure 7A:
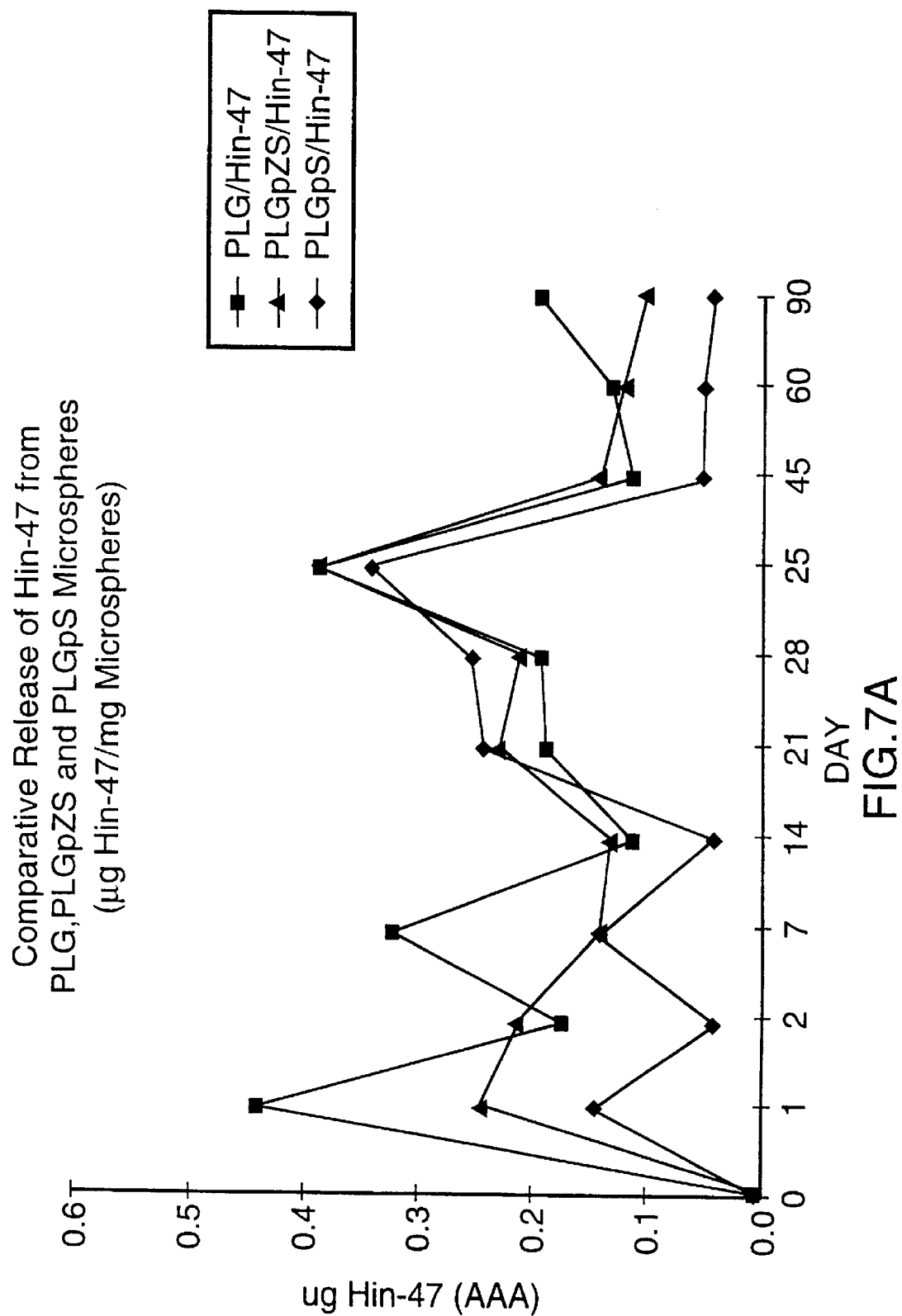
FIG. 7A shows the in vitro release profile for non-proteolytic Hin-47 analog encapsulated within PLG, PLGpZS and PLGpS microparticles over a three month period obtained from 14 mg samples (typical core loadings range from 2.5 to 5.7 μg protein/mg of microparticles) that were incubated in PBS (pH=7.4) and maintained at 37° C.

FIG. 7A illustrates the release rate at specific time points for each sample and FIG. 7B shows the % cumulative release for each sample examined. It is evident that under these conditions the best recovery of protein from microspheres follows the order PLGpS>PLG>PLGpZS although the core loading for the PLGpZS microparticles was approximately twice that of the PLG or PLGpS analogs and this may influence the release rate. In addition, this matrix has been shown to degrade at a slower rate and thus there may be residual material within the microparticles. Evidence for this can be seen in FIG. 7B whereby a marginal increase in protein recovery was observed from day 60 to day 90 for PLGpZS microparticles. Over this same time interval, protein recovered from PLG or PLGpS microparticles was essentially non-existent.

In control experiments, supernatant solutions of PBS obtained from periodic extractions of PBS loaded PLG, PLGpZS or PLGpS microparticles incubated at 37° C. were monitored for pH changes. It is known that the erosion process for PLGA matrices is accompanied by changes in the pH microenvironment within the microparticle (ref. 36). This can have a serious effect on protein stability as pH induced conformational changes can ensue as a consequence of these changes. An indication of the magnitude of these changes can be obtained by monitoring the pH of the surrounding medium. We have found that incorporation of small percentages of amino acid sub-units within the copolymer can retard this process. This may be of importance during the release phase for proteins sensitive to acidic pH. Specifically when incubating ~10 mg of microparticles in 1.2 mL of PBS buffer (pH=7.4) it required approximately 16 days for supernatant extractions of PLG (Mw=26,000 daltons) to fall below 5 pH 5.0. By analogy the pH of supernatant extractions obtained from PLGpZS (Mw=20,000 daltons, approximately 2.0% serine incorporated), or PLGpS (Mw=18,000 daltons, approximately 1.7% serine incorporated) was determined to be approximately 5.5 to 6.2 respectively. The degradation rates for PLG and PLGpS examined in this study were similar (as measured by mass loss of matrix) whereas the PLGpS matrix degraded at a reduced rate.

Thus the in vitro release study demonstrates that a single dose delayed release delivery system can be achieved through use of polymeric microparticles formulated from PLGpZS or PLGpS copolymers. In addition as pH changes with matrix erosion can have a deleterious effect on the protein stability it may be advantageous to employ matrices derived from pseudo-serine ester such as PLGpZS or PLGpS wherein there exists some buffering capacity for these changes during the protein release phase.

Example 8

This Example illustrates the immunogenicity of non-proteolytic Hin-47 analog encapsulated or physically mixed with microparticles in mice which were immunized subcutaneously.

To examine the immunogenicity of non-proteolytic Hin-47 analog entrapped in PLG, PLGpZS and PLGpS microparticles formed in accordance with the present invention, groups of five, 6 to 8 week old female BALB/c mice (Charles River Breeding Laboratories, Wilmington, Mass.) were immunized subcutaneously (S.C.) with the following amounts of antigen in 250 $\mu$L of PBS (pH 7.4) on days 1 and 35: PLG, PLGpZS and PLGpS microparticles prepared as described in Example 5 containing 0.2 μg or 0.6 μg of non-proteolytic Hin-47 analog (FIG. 8A); and PLG microparticles prepared as described in Example 5 physically mixed with 0.8 μg or 2.5 μg of non-proteolytic Hin-47 analog (FIG. 8B).

The mice showed no gross pathologies or behavioral changes after receiving microparticles that contained encapsulated non-proteolytic Hin-47 analog or microparticles that were physically mixed with non-proteolytic Hin-47 analog. Sera were obtained on days +10, +24, +35, +45 and +60 and were evaluated for the presence of anti-Hin-47 IgG antibodies by antigen specific ELISA. All samples were analyzed in duplicate. Microtiter plate wells were incubated overnight at room temperature with 100 μL of 0.2 μg/mL non-proteolytic Hin-47 analog in 0.05M carbonate-bicarbonate buffer (pH 9.0). The plates were washed with PBS+0.05% Tween 20 (operationally defined as washing buffer). Wells were incubated with 200 μL of 5% skim milk (operationally defined as blocking buffer). After washing with PBS+0.05% Tween 20, the plates were incubated for 1 h at 37° C. with 100 μL of sample serially diluted in blocking buffer. Wells were washed with PBS+0.05% Tween 20 and 100 μL of HRP-conjugated antibody (goat anti-mouse IgG (H+L) (Jackson), sheep anti-mouse IgG1 (Serotec), goat anti-mouse IgG2a (Caltag) or goat anti-mouse IgG2b (Caltag) in blocking buffer was added to each well. After 1 hour incubation at 37° C., the wells were washed five times with PBS+0.05% Tween 20 and 100 μL of freshly prepared colorizing substrate [$H_2O_2$ (9 parts) and TMB (1 part)] is added to each well. After 5 minutes incubation in the dark at room temperature the reaction is stopped by adding 50 μL of a 2M $H_2SO_4$ solution and the optical density of the fluid in each well was determined at 450 nm using a microplate reader. A normal mouse sera pool was used to establish baseline optical density values in the assay. Hyperimmune mouse Hin-47 antiserum was used as a positive control. Pre-immune sera was used as negative control.

For serum IgA analysis the above procedure was conducted with the following modification. Microtiter plate wells were incubated overnight at room temperature with 100 μL of 1.3 pg/mL non-proteolytic Hin-47 analog in 0.05M carbonate-bicarbonate buffer (pH=9.0), and 100 μL of HRP conjugated rabbit anti-mouse IgA (ZYMED, CA) at 0.06 μg/mL was added to each well.

For secretory IgA analysis, the above procedure was conducted with the following modification. 100 μL of HRP conjugated rat anti-mouse IgA (Biotin-Pharmigen) at 0.06 μg/mL was added to each well.

Figure 8A:
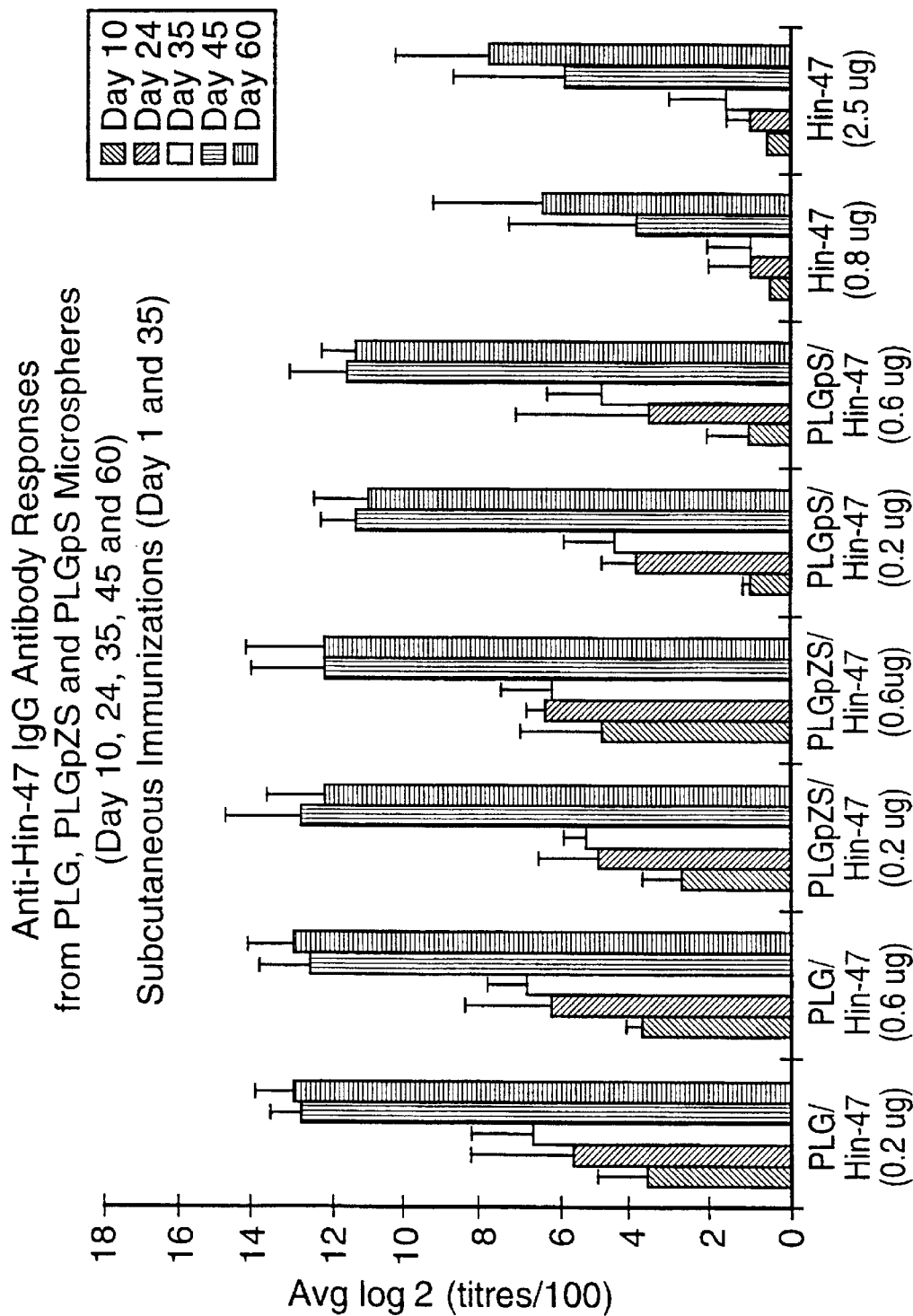
FIG. 8A shows the serum IgG responses in mice immunized subcutaneously (S.C.) following various immunization protocols by the 47 kDa membrane protein from *Haemophilus influenzae* (non-proteolytic Hin-47 analog). Groups of 5 mice were immunized on days 1 and 35 with 250 μL of PBS, pH 7.4, containing either 0.2 or 0.6 μg of non-proteolytic Hin-47 analog incorporated into PLG, PLGpZS or PLGpS microparticles. Sera obtained on days +10, +24, +35, +46 and +60 were evaluated for the presence of anti-Hin-47 IgG antibodies using an enzyme-linked immunosorbent assay (ELISA).
Figure 8B:
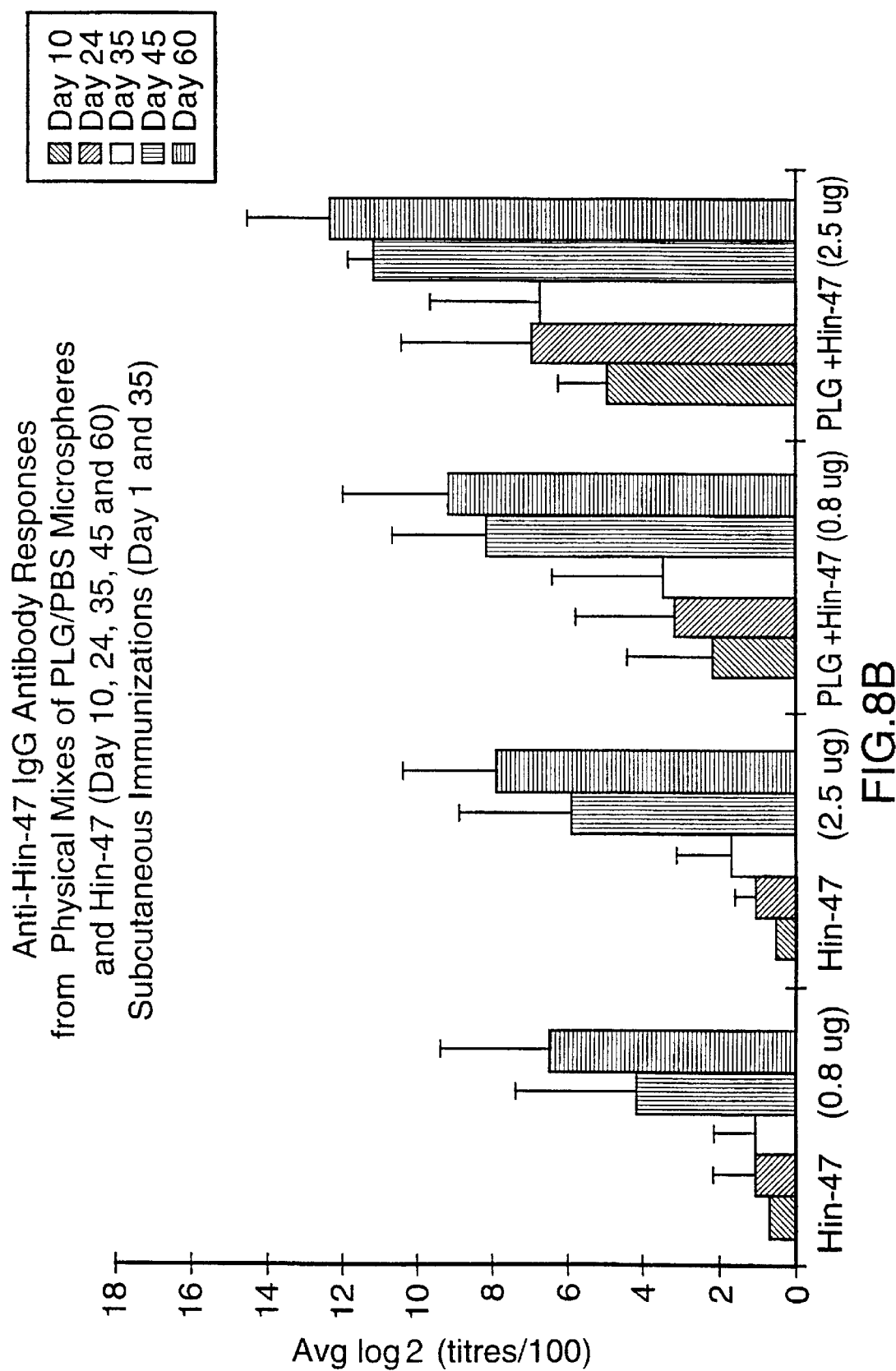
FIG. 8B shows the serum IgG responses in mice immunized subcutaneously (S.C.) following various immunization protocols by the 47 kDa membrane protein from *Haemophilus influenzae* (non-proteolytic Hin-47 analog). Groups of 5 mice were immunized on days 1 and 35 with 250 μL of PBS, pH 7.4, containing either 0.8 or 2.5 μg of non-proteolytic Hin-47 analog physically mixed with PLG microparticles. Sera obtained on days +10, +24, +35, +46 and +60 were evaluated for the presence of anti-Hin-47 IgG antibodies using an enzyme-linked immunosorbent assay (ELISA).

The serum antibody titres following immunization are shown in FIGS. 8A and 8B. The results of immunizations indicate that antigen presented to the immune system entrapped in PLG, PLGpZS or PLGpS microparticles (FIG. 8A) was substantially more immunogenic than soluble antigen at doses sub-optimal to that required with soluble antigen alone. In addition, no dose dependence was observed with encapsulated non-proteolytic Hin-47 analog of dose 0.2 μg or 0.6 μg, whereas a marginal increase in titre was found with soluble non-proteolytic Hin-47 analog of dose 0.8 μg or 2.5 μg respectively.

The results of immunizations indicate that antigen presented to the immune system when physically mixed with PLG microparticles (FIG. 8B) is marginally more immunogenic than soluble antigen at similar dose to that given with soluble antigen alone (0.8 μg or 2.5

82 g). However, administration of antigen in soluble form or admixed with microparticles elicits a response several orders of magnitude less than that seen for antigen encapsulated within the microparticles demonstrating the advantages of encapsulation over soluble or physically mixing alone.

Interestingly, the IgG subtype profile (FIG. 8C) for pooled serum obtained from the bleeds on day 35 and 60 for microparticle encapsulated non-proteolytic Hin-47 analog, microparticles physically mixed with non-proteolytic Hin-47 analog or soluble non-proteolytic Hin-47 analog shows that by day 35 IgG1 was the dominant subtype with some IgG2b detected irrespective of formulation. By day 60 it was evident that the IgG subtypes induced by non-proteolytic Hin-47 analog encapsulated within microparticles had undergone class switching such that IgG1, IgG2a and IgG2b are more equally represented. The IgG subtypes induced by non-proteolytic Hin-47 analog physically mixed with particles or in soluble form by day 60 was nominally the same as that determined for day 35 with the IgG1 subtype dominant.

Thus, it can be concluded that the qualitative nature of the immune response mediated by microparticles encapsulating antigen is substantially different than that obtained by physically mixing with microparticles or by soluble antigen alone. The presence of IgG2a subtype in the BALB/c mouse model is generally accepted to be indicative of a $TH_1$ pathway, and IgG1 indicative of a $TH_2$ pathway. It is evident that via the subcutaneous route the $TH_2$ pathway is favored for soluble antigen or for antigen physically mixed with microparticles, whereas with antigen encapsulated within microparticles a more balanced $TH_1/TH_2$ response is attainable.

Example 9

This Example illustrates the immunogenicity of non-proteolytic Hin-47 analog entrapped in PLG, PLGpZS and PLGpS microparticles formed in accordance with the present invention, in mice immunized intragastrically.

Groups of five, 6 to 8 week old female BALB/c mice (Charles River Breeding Laboratories, Wilmington, Mass.) were immunized intragastrically (I.G.) with the following amounts of antigen in 250 μL of 0.15 M $NaHCO_3$ (pH 9.0) on days 1, 7, 14 and 57: PLG, PLGpZS and PLGpS microparticles prepared as described in Example 5 containing 4.0 μg of non-proteolytic Hin-47 analog; and PLG, PLGpZS and PLGpS microparticles prepared as described in Example 5 physically mixed with 4.0 μg non-proteolytic Hin-47 analog (FIG. 9A).

The mice showed no gross pathologies or behavioral changes after receiving microparticles that contained encapsulated non-proteolytic Hin-47 analog or microparticles that were physically mixed with non-proteolytic Hin-47 analog. Sera were obtained on days +13, +35, +56 and +78 and were evaluated for the presence of anti-Hin-47 IgG and IgA antibodies by antigen specific ELISA as described in Example 8.

Sera and intestinal washes were examined for the presence of Hin-47-specific antibodies. To detect and quantify anti-Hin-47 IgG and sIgA in the intestinal lumen, mice were sacrificed by cervical dislocation, their small intestines removed and examined for the presence of antigen-specific antibodies. Individual small intestines were detached from the pyloric sphincter to the caecum and everted over capillary tubes. The everted intestines were incubated in 5 mL of ice cold enzyme inhibitor solution (0.15 M NaCl, 0.01 M $Na_2HPO_4$, 0.005 M EDTA, 0.002 M PMSF, 0.05 U/mL Aprotinin, and 0.02% v/v $NaN_3$) for 4 hours. Intestines were removed and the supernatants clarified by centrifugation (1000 xg, 20 minutes) and stored at 0° C. until assayed. Anti-Hin-47 IgG and sIgA titres in samples were determined by Hin-47-specific ELISA as described above but a goat anti-mouse IgA antiserum was used in place of the goat anti-mouse IgG antiserum.

Figure 9A:
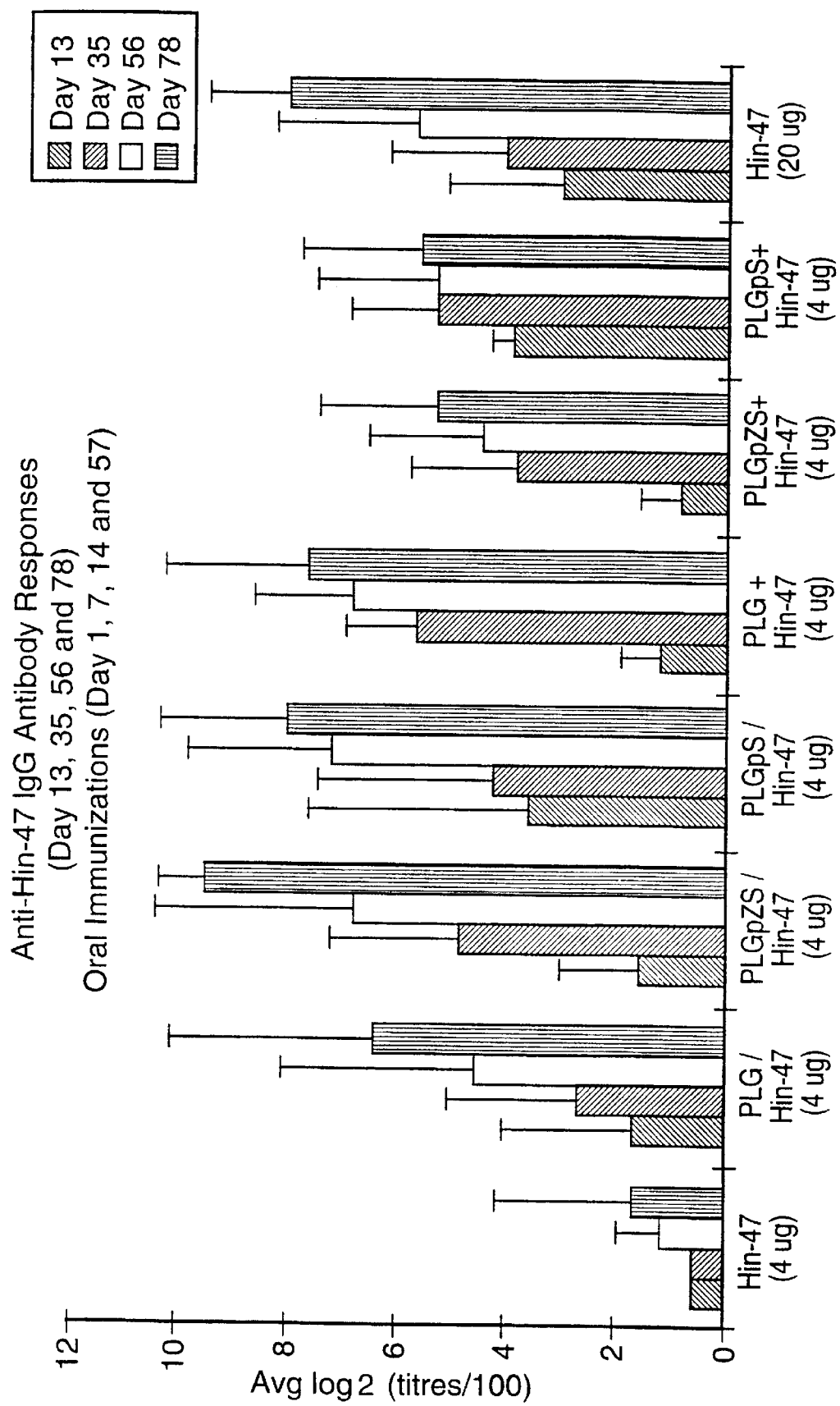
FIG. 9A shows the IgG serum antibody responses in mice immunized intragastrically (I.G.) by the 47 kDa membrane protein from *Haemophilus influenzae* (non-proteolytic Hin-47 analog). Groups of 5 mice were immunized on days 1, 7, 14 and 57 with 500 μL of PBS, pH 7.4, containing 4 pg of Hin-47 analog incorporated into PLG, PLGpZS or PLGpS microparticles or physically mixed with PLG, PLGpZS or PLGpS microparticles. Sera obtained on days +13, +35, +56 and +78 were evaluated for the presence of anti-Hin-47 IgG antibodies using an enzyme-linked immunosorbent assay (ELISA).

The serum IgG Hin-47-specific antibody titres following I.G. immunization is shown in FIG. 9A. These results indicate that an antigen (non-proteolytic Hin-47 analog) incorporated into PLG, PLGpZS or PLGpS microparticles was substantially more immunogenic than soluble antigen of similar dose (4 μg) and better than antigen that was physically mixed with microparticles when delivered by the intragastric route. It was experimentally determined that a dose of soluble antigen (20 μg) which was five times that which was administered encapsulated within microparticles (4 μg) was required to elicit an essentially equivalent response. This result is atypical for most proteins as there are many examples where in excess of 100 μg of antigen is required to elicit any significant serum IgG antibody response via the intragastric route.

The IgG subtype profile (FIG. 9B) for pooled serum obtained from the bleeds on day 56 and 78 for microparticle encapsulated non-proteolytic Hin-47 analog, microparticles physically mixed with non-proteolytic Hin-47 analog or soluble non-proteolytic Hin-47 analog shows a similar trend as that observed in Example 8. The IgG1 subtype was dominant when antigen was delivered in soluble form or when physically mixed with microparticles. Non-proteolytic Hin-47 analog encapsulated within microparticles exhibits a more balanced profile with IgG1 and IgG2a more equally represented. Thus via the intragastric route with antigen encapsulated within microparticles a more balanced $TH_1$/$TH_2$ response was attainable.

FIG. 9C shows the results for anti-Hin-47 IgA antibody responses obtained from bleeds on day 78. With soluble antigen at 4 μg per dose no detectable serum IgA was found, however at 20 μg per dose a few responders were observed. A single significant response was observed with antigen encapsulated within PLG microparticles and moderate responses observed for antigen encapsulated within PLGpZS or PLGpS microparticles. Similarly modest response was seen for antigen physically mixed with PLG, PLGpZS or PLGpS microparticles. The highest average levels of serum IgA were obtained for antigen encapsulated within PLGpS microparticles. The intestinal lavage conducted on day 78 revealed minimal levels of IgG or sIgA specific for Hin-47 analog in the mucosal secretions obtained from non-proteolytic Hin-47 analog encapsulated within PLG, PLGpZS or PLGpS microparticles. This is likely due to the very low levels of encapsulated antigen administered in this experiment (4 μg per dose) as oral doses of antigen ranging from 30 μg to 100 μg are usually required to elicit a significant mucosal response in the absence of any other mucosal adjuvants.

Example 10

This Example illustrates the immunogenicity of non-proteolytic Hin-47 analog entrapped in PLG, PLGpZS and PLGpS microparticles formed in accordance with the present invention, in mice immunized intranasally.

Groups of five, 6 to 8 week old female BALB/c mice (Charles River Breeding Laboratories, Wilmington, Mass.) were immunized intranasally (I.N.) with the following amounts of antigen in 25 μL of PBS (pH 7.4) on days 1, 7, 14 and 57: PLG, PLGpZS and PLGpS microparticles prepared as described in Example 5 containing 4.0 μg of non-proteolytic Hin-47 analog; and PLG, PLGpZS and PLGpS microparticles prepared as described in Example 5 physically mixed with 4.0 μg non-proteolytic Hin-47 analog (FIG. 10A).

The mice showed no gross pathologies or behavioral changes after receiving microparticles that contained encapsulated non-proteolytic Hin-47 analog or microparticles that were physically mixed with non-proteolytic Hin-47 analog. Sera were obtained on days +13, +35, +56 and +78 and were evaluated for the presence of anti-Hin-47 IgG and IgA antibodies by antigen specific ELISA as described in Example 8.

Sera and lung lavage washes were examined for the presence of Hin-47-specific antibodies. To detect and quantify anti-Hin-47 IgG and sIgA in the respiratory tract, mice were sacrificed by cervical dislocation, a small incision was made in the trachea and a tube inserted through the trachea into the lungs where 400 μL of an enzyme inhibitor solution (0.15 M NaCl, 0.01 M $Na_2HPO_4$, 0.005 M EDTA, 0.002 M PMSF, 0.05 U/mL Aprotinin, and 0.02% v/v $NaN_3$) was injected. This solution was then withdrawn, placed on ice and the supernatants clarified by centrifugation (1000 xg, 20 minutes) and stored at 0° C. until assayed. Anti-Hin-47 IgG and sIgA titres in samples were determined by Hin-47-specific ELISA as described in Example 8.

The serum IgG Hin-47-specific antibody titres following I.N. immunization is shown in FIG. 10A. These results indicate that an antigen (non-proteolytic Hin-47 analog) incorporated into or physically mixed with PLG, PLGpZS or PLGpS microparticles was more immunogenic than soluble antigen of similar dose (4 μg). Essentially equivalent response was obtained for antigen that was encapsulated or physically mixed with microparticles by the intranasal route.

The IgG subtype profile (FIG. 10B) for pooled serum obtained from the bleeds on day 56 and 78 for microparticle encapsulated non-proteolytic Hin-47 analog, microparticles physically mixed with non-proteolytic Hin-47 analog or soluble non-proteolytic Hin-47 analog illustrated a trend different from that shown in Example 8 or Example 9. Non-proteolytic Hin-47 analog encapsulated within microparticles exhibited a more balanced profile with IgG1, IgG2a and IgG2b essentially equally represented at either timepoint (day 56 or day 78). For antigen delivered in soluble form or when physically mixed with microparticles, a similar profile was seen by day 78 where significant levels of IgG2a can also be seen.

Thus, via the intranasal route, the $TH_1$/$TH_2$ response was essentially the same irrespective of whether antigen was encapsulated within microparticles, physically mixed with microparticles or in soluble form.

FIG. 10C shows the results for anti-Hin-47 IgA antibody responses obtained from bleeds on day 78. With soluble antigen no detectable serum IgA was found. However, significant response was seen for antigen that is encapsulated or physically mixed with microparticles. The highest levels obtained for antigen either encapsulated or physically mixed with PLGpS microparticles.

The lung lavage conducted on day 78 revealed substantial differences with respect to IgG and sIgA detected from secretions. The anti-Hin-47 IgG antibody response (FIG. 10D) from soluble antigen was negligible, however antigen encapsulated within microparticles or physically mixed with PLG microparticles elicited significant levels of IgG from half of each group examined. The most reproducible response for IgG was found with antigen physically mixed with microparticles derived from PLGpZS or PLGpS where most or all mice examined possessed significant levels of IgG.

Figure 10A:
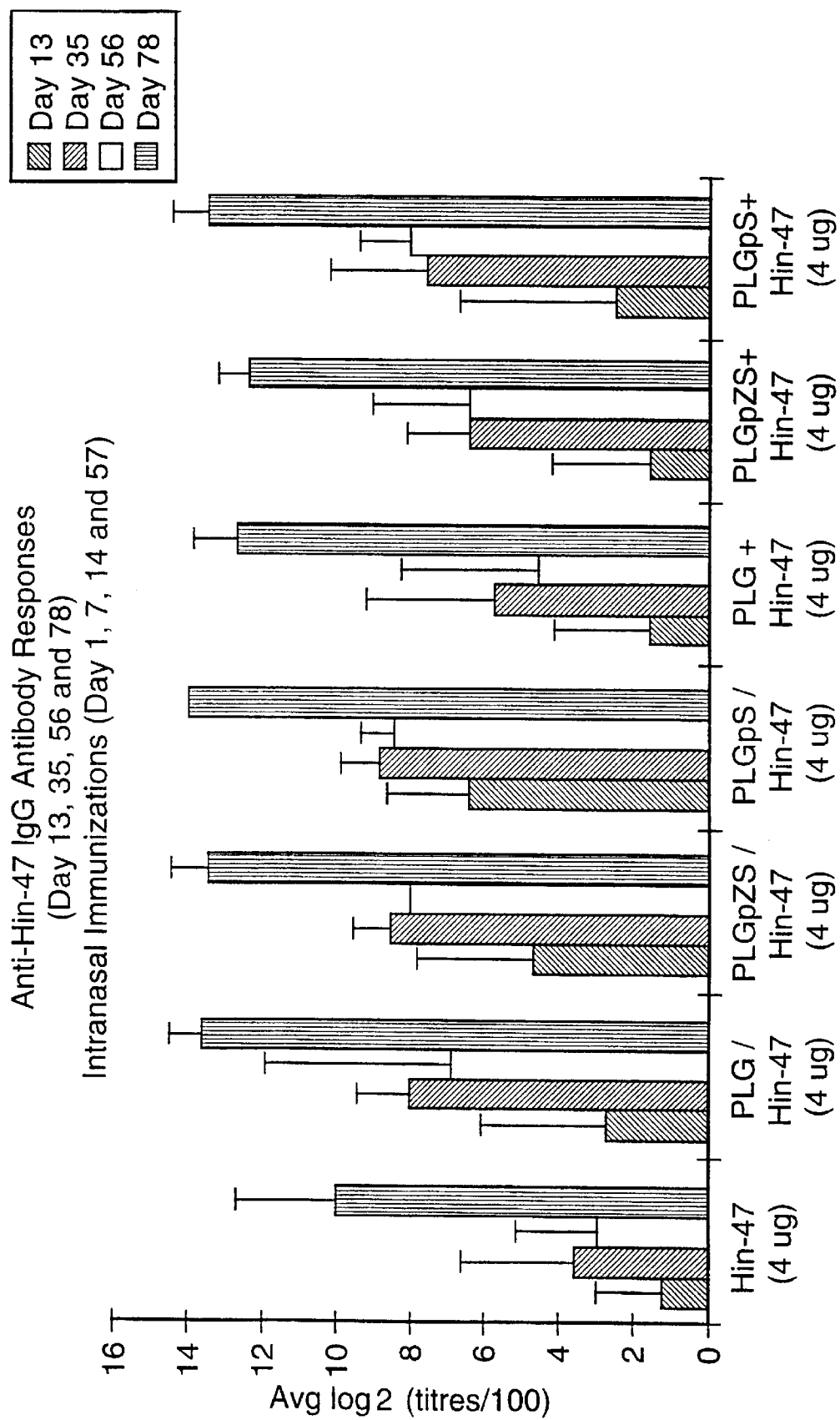
FIG. 10A shows the IgG serum antibody responses in mice immunized intranasally (I.N.) by a (1:1) cocktail of the 47 kDa membrane protein from *Haemophilus influenzae* (non-proteolytic Hin-47 analog) and the 115 kDa membrane protein from *Haemophilus influenzae* (rD-15). Groups of 5 mice were immunized on days 1, 7, 14 and 57 with 25 μL of PBS, pH 7.4, containing 4 μg of non-proteolytic Hin-47 analog incorporated into PLG, PLGpZS or PLGpS microparticles or physically mixed with PLG, PLGpZS or PLGpS microparticles. Sera obtained on days +13, +35, +56 and +78 were evaluated for the presence of anti-Hin-47 IgG antibodies using an enzyme-linked immunosorbent assay (ELISA).
Figure 10B:
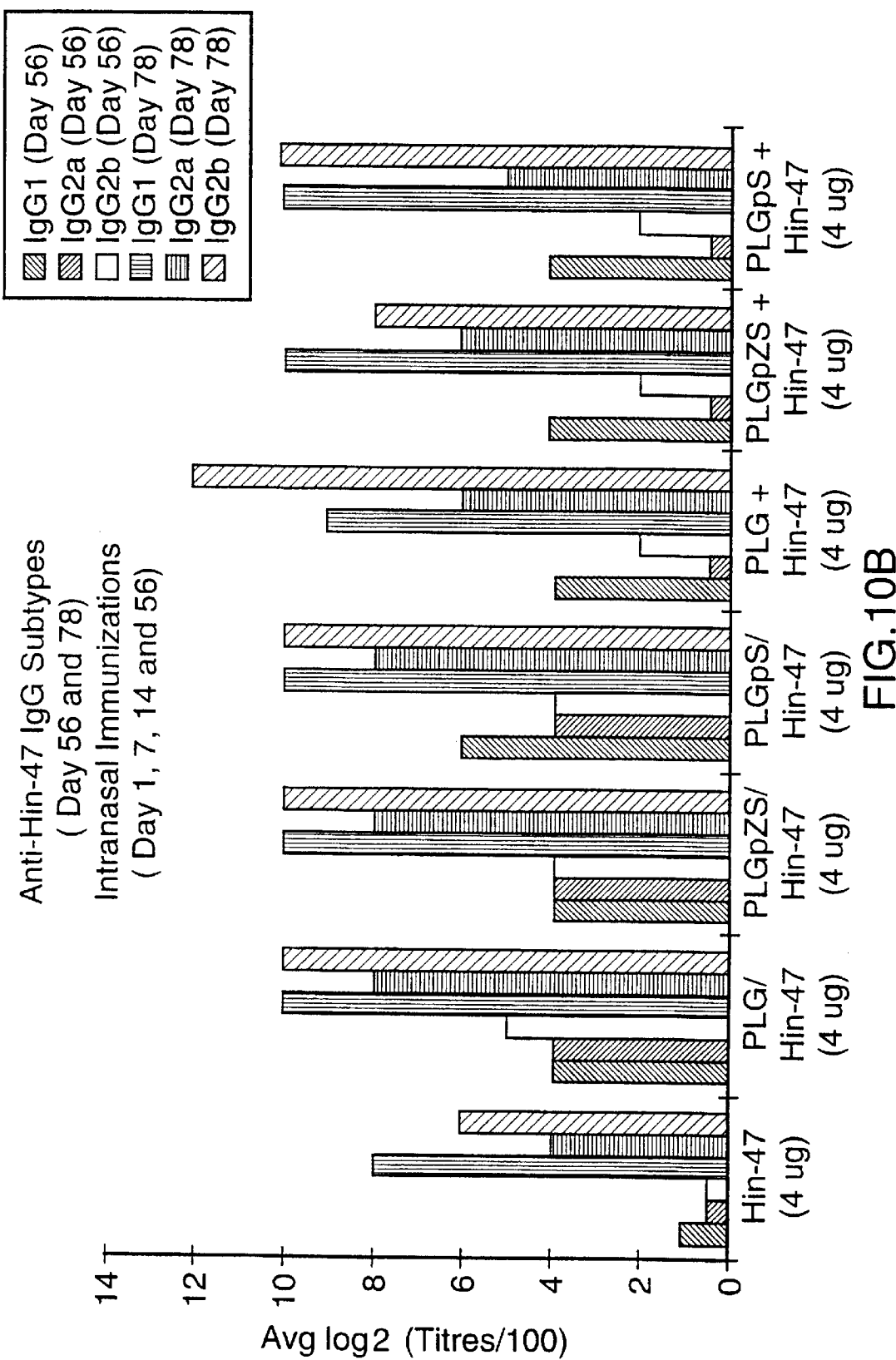
FIG. 10B shows the serum IgG response subtype profile for pooled bleeds obtained on days +56 and +78 from the study conducted as described in FIG. 10A.

The anti-Hin-47 sIgA antibody response (FIG. 10E) was similar to that obtained for IgG in FIG. 10D. Soluble antigen response was negligible with antigen encapsulated within microparticles or physically mixed with PLG microparticles showing some response. The most significant response for sIgA was found with antigen physically mixed with microparticles derived from PLGpZS or PLGpS where most mice have reasonable levels of sIgA.

The induction of local protection at mucosal surfaces is often associated with the presence IgG and sIgA in local secretions. Whereas it cannot be ruled out that the intranasal immunization has not also resulted in immunization of the upper respiratory tract, it is clear that for serum IgG antibody response encapsulated or physically mixed antigen with microparticles is effective. To induce local secretions of IgG and sIgA physically mixing antigen with microparticles and more specifically microparticles formulated from either PLGpZS or PLGpS appears to be the more suitable method under these conditions.

Example 11

This Example illustrates the immunogenicity of Flu-X-31 or Flu X-31 plus a co-adjuvant BAY R1-005 entrapped in PLG, PLGpZS and PLGpS microparticles formed in accordance with the present invention, in mice immunized subcutaneously.

Groups of six, 6 to 8 week old female BALB/c mice (Charles River Breeding Laboratories, Wilmington, Mass.) were immunized subcutaneously (S.C.) with the following amounts of antigen in 250 µL of PBS (pH 7.4) on day 1: PLG, PLGpZS and PLGpS microparticles prepared as described in Example 5 containing 5.0 µg of Flu X-31 (1.5 µg HA) or 5.0 µg of Flu X-31 (1.5 µg HA) and 50 µg BAY R1-005 when administered in soluble form or approximately 20 µg BAY R1-005 when co-encapsulated (FIG. 11).

The mice showed no gross pathologies or behavioral changes after receiving microparticles that contained encapsulated Flu X-31 or Flu X-31 with BAY R1-005. Sera were obtained on days +21 and +33 and were evaluated for the presence of anti-Flu X-31 IgG antibodies by antigen specific ELISA. All samples were analyzed in duplicate.

Microtiter plate wells were incubated overnight at room temperature with 500 µL of 4.0 µg/mL Flu X-31 in 0.05M carbonate-bicarbonate buffer (pH=9.6). The plates were washed with PBS+0.05% Tween 20 (operationally defined as washing buffer). Wells were incubated with 200 µL of 5% skim milk (operationally defined as blocking buffer). After washing with PBS+0.05% Tween 20, the plates were incubated for 1 h at 37° C. with 100 µL of sample serially diluted in blocking buffer. Wells were washed with PBS+0.05% Tween 20 and 100 µL of HRP-conjugated antibody (goat anti-mouse IgG (H+L), IgG1, IgG2a or IgG2b) in blocking buffer was added to each well. After 1 hour incubation at 37° C., the wells were washed 5X with PBS+0.05% Tween 20 and 100 µL of freshly prepared colorizing substrate [$H_2O_2$ (9 parts) and TMB (1 part)] is added to each well. After 5 minutes incubation in the dark at room temperature the reaction is stopped by adding 50 µL of a 2M $H_2SO_4$ solution and the optical density of the fluid in each well was determined at 450 nm using a microplate reader. A normal mouse sera pool was used to establish baseline optical density values in the assay. Hyperimmune mouse Flu X-31 antiserum was used as a positive control. Pre-immune sera is used as negative control.

Figure 11:
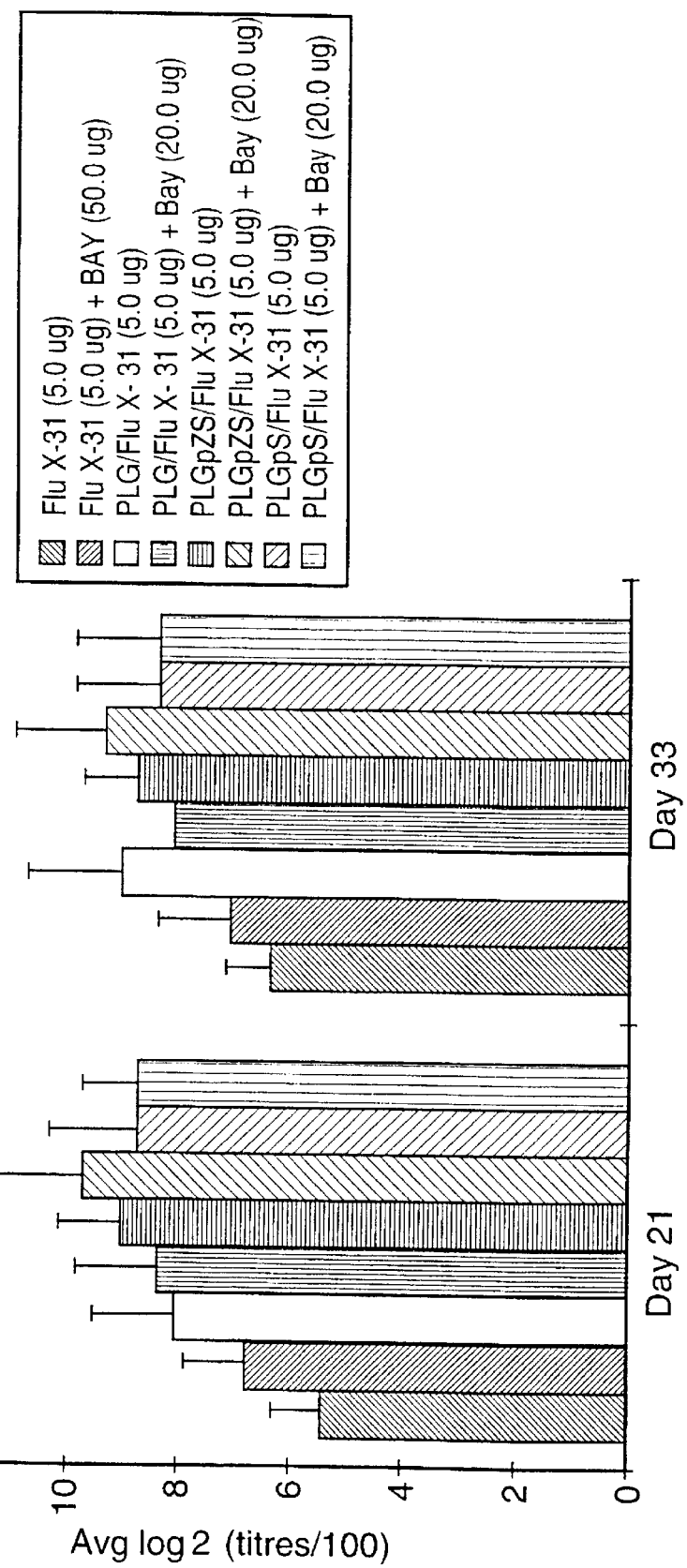
FIG. 11 shows the anti-Flu X31 (i.e. influenza virus type A strain X31) IgG serum antibody responses following various immunization protocols. Groups of 6 mice were immunized subcutaneously (S.C.) on day 1 with 250 μL of PBS, pH 7.4, containing 1.5 μg of HA incorporated into PLG, PLGpZS or PLGpS microparticles. Sera obtained on days +21 and +33 and were evaluated for the presence of anti-Flu X-31 IgG antibodies using an enzyme-linked immunosorbent assay (ELISA).

The serum antibody titres following immunizations are shown in FIG. 11. The results of a single immunization (day 1) indicated that antigen presented to the immune system entrapped in PLG, PLGpZS or PLGpS microparticles was more immunogenic than soluble antigen alone. The most relevant results were obtained with Flu X-31 or Flu X-31 plus BAY R1-005 encapsulated within PLGpZS microparticles. Although a sub-optimal dose of BAY R1-005 was encapsulated within all microparticles examined, the immunogenic response with the PLGpZS microparticles also proved to be significantly higher than that obtained with soluble Flu X-31 and BAY R1-005 alone.

The studies presented in this Example demonstrate that viral antigens from influenza virus can be made more immunogenic and elicit high levels of serum IgG antibodies, when the antigens are entrapped in microparticles formed in accordance with the present invention. In addition the significantly higher immunogenicity displayed by the microparticle systems after a single immunization demonstrates the potential of these materials for development as single dosage vaccines.

Example 12

This Example illustrates the immunogenicity of Flu-X-31 or Flu X-31 plus a co-adjuvant BAY R1-005 entrapped in PLG, PLGpZS and PLGpS microparticles formed in accordance with the present invention, in mice immunized intranasally.

Figure 12:
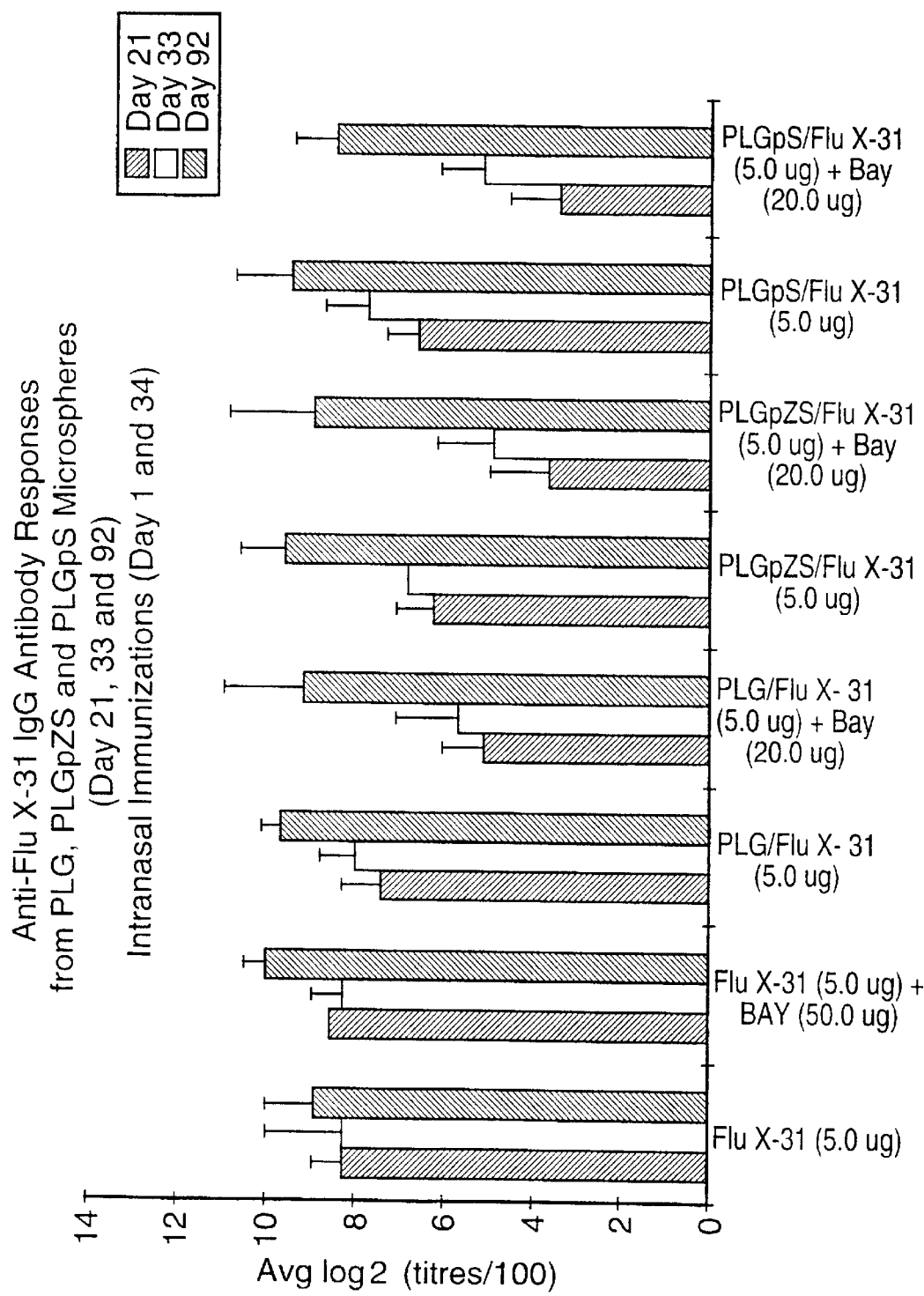
FIG. 12 shows the anti-Flu X31 (i.e. influenza virus type A strain X31) IgG serum antibody responses following various immunization protocols. Groups of 6 mice were immunized intranasally (I.N.) on days 1 and 34 with 25 μL of PBS, pH 7.4, containing 1.5 μg of HA incorporated into PLG, PLGpZS or PLGpS microparticles. Sera obtained on days +21, +33, +57, +78 and +92 were evaluated for the presence of anti-Flu X-31 IgG antibodies using an enzyme-linked immunosorbent assay (ELISA).

Groups of six, 6 to 8 week old female BALB/c mice (Charles River Breeding Laboratories, Wilmington, Mass.) were immunized intranasally (I.N.) with the following amounts of antigen in 25 µL of PBS (pH 7.4) on days 1 and 34: PLG, PLGpZS and PLGpS microparticles prepared as described in Example 5 containing 5.0 µg of Flu X-31 (1.5 µg HA) or 5.0 µg of Flu X-31 (1.5 µg HA) and 50 µg BAY R1-005 when administered in soluble form or approximately 20 µg BAY R1-005 when co-encapsulated (FIG. 12).

The mice showed no gross pathologies or behavioral changes after receiving microparticles that contained encapsulated Flu X-31 or Flu X-31 with BAY R1-005. Sera were obtained on days +21, +33 and +92 and were evaluated for the presence of anti-Flu X-31 IgG antibodies by antigen specific ELISA as described in Example 10. All samples were analyzed in duplicate.

Mice immunized I.N. with soluble antigen, soluble antigen plus co-adjuvant or encapsulated antigen showed a similar anti-Flu X-31 IgG antibody response. Interestingly, a reduced (likely due to delayed release) immunogenic response for encapsulated antigen plus co-adjuvant relative to soluble antigen, antigen plus adjuvant or encapsulated antigen on day +21 and +33 was shown when administered via the nasal route. However, after the second immunization (day 34) a significant boost in response with these groups was observed resulting in essentially similar immunogenicity on day +92 for all groups irrespective of adjuvant used.

The results of the I.N. immunizations described in this Example shows that the immunogenicity of an antigen or antigen plus a co-adjuvant cannot be significantly enhanced by entrapment in microparticles formed in accordance with the present invention.

Example 13

This Example illustrates the immunogenicity of Flu A-Texas or Flu A-Texas +BAY R1-005 encapsulated or physically mixed with microparticles in mice immunized subcutaneously.

It is known that most non-replicating viral vaccines require multiple doses for sufficient serum antibody titres to be protective. Thus, it is strongly desirable to achieve this by administering a single dose of antigen.

Figure 13:
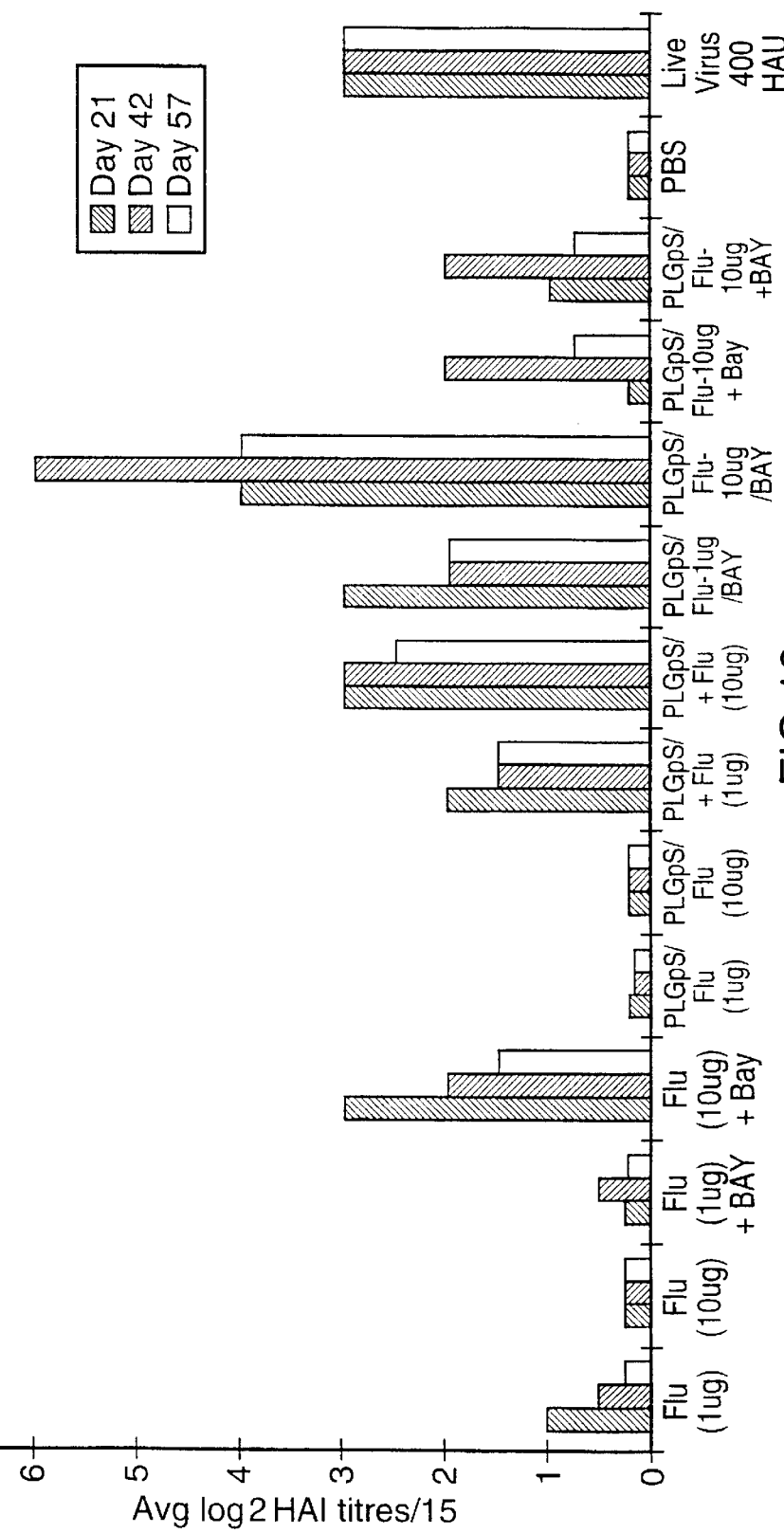
FIG. 13 shows the hemagglutination inhibition antibody assay (i.e. influenza virus strain A-Texas) responses for pooled sera (days +21 and +42 or +57) following a single dose subcutaneous administration. Groups of 6 mice were immunized subcutaneously (S.C.) On day 1 with 250 μl of PBS, pH 7.4, containing either 0.35 μg of HA or 3.5 μg of HA incorporated into PLGpS microparticles or 0.35 μg of HA and ~2 μg of BAY R1-005 or 3.5 μg of HA and ~20 μg of BAY R1-005 incorporated into PLGpS microparticles or 0.35 μg of HA or 3.5 μg of HA physically mixed with PLGpS microparticles or 0.35 μg of HA and 2 μg of BAY R1-005 or 3.5 μg of HA and 20 μg of BAY R1-005 physically mixed with PLGpS microparticles. Sera obtained on days +21 and +42 were evaluated for the inhibition of hemagglutination of erythrocytes.

We sought to examine the immunogenicity of Flu A-Texas or Flu A-Texas plus a co-adjuvant BAY R1-005 which was entrapped in PLGpS microparticles or physically mixed with microparticles administered as a single dose, formed in accordance with the present invention. Groups of six, 6 to 8 week old female DBA2 mice (Charles River Breeding Laboratories, Wilmington, Mass.) were immunized subcutaneously (S.C.) with the following amounts of antigen in 250 µL of PBS (pH 7.4) on day 1: PLGpS prepared as described in Example 5 containing 1.0 µg of Flu A-Texas (0.35 µg HA) or 10.0 µg of Flu A-Texas (3.5 µg HA) or 1.0 µg of Flu A-Texas (0.35 µg HA) and approximately 2.0 µg of BAY R1-005 or 10.0 µg of Flu A-Texas (3.5 µg HA) and approximately 20 µg of BAY R1-005 or microparticles prepared as described in Example 5 physically mixed with 1.0 µg of Flu A-Texas (0.35 µg HA) and 20 µg of BAY R1-005 or 10.0 µg of Flu A-Texas (3.5 µg HA) and 20 µg of BAY R1-005 (FIG. 13).

The core loading of PLGpS microparticles containing Flu A-Texas and BAY R1-005 was determined via amino acid analysis (Table 1). The mass of microparticles administered was adjusted such that the required dose of Flu A-Texas (1.0 µg of Flu A-Texas (0.35 µg HA) for the low dose groups or 10.0 µg of Flu A-Texas (3.5 µg HA) for the high dose groups) was delivered. Thus the dose of BAY R1-005 delivered for the high dose groups was ten fold greater than that of the low dose groups examined. It is expected that formulation conditions can be adjusted such that the quantity of BAY R1-005 co-encapsulated is comparable.

The mice showed no gross pathologies or behavioral changes after receiving microparticles that contained encapsulated Flu A-Texas or Flu A-Texas with BAY R1-005. Sera were obtained on days +21 and +42 or +57 and were evaluated for the presence of functional antibody via the hemagglutination inhibition antibody assay (HAI). All samples were analyzed in duplicate.

The influenza hemagglutination inhibition antibody assay was performed with heat-inactivated mouse serum that had been incubated for 30 minutes with 10% chicken red blood cells to remove non-specific inhibitors. Twofold dilutions of sera were added to a 96 well microtiter plate and 8 HA units of virus suspension in an equal volume were added to each well and incubated at room temperature for 30 minutes. A 1.0% suspension of chicken red blood cells were added to each well and incubated at room temperature for 30 minutes. Positive and negative reference sera were included in the test to ascertain specificity and sensitivity of the test. Positive sera from influenza virus immunized animals. Negative sera from PBS immunized animals, titre should be less than or equal to 15. The HAI titres are expressed as the reciprocal of the highest dilution that completely inhibits hemagglutination of erythrocytes.

The results of a single immunization (day 1) as shown in FIG. 13 indicate that by day +42 antigen presented to the immune system in soluble form or entrapped in PLGpS microparticles (FIG. 13) elicits negligible or low functional antibody. For Flu (10 µg) presented to the immune system as a physical mixture with BAY R1-005 the HAI response elicited was 8xhigher than that obtained with soluble antigen of similar dose and 6xhigher that that obtained by PLGpS/Flu microparticles of either dose. The most relevant results were obtained for PLGpS/Flu(A-Texas)/BAY R1-005 formulated microparticles wherein the HAI titre of the low dose group (1 µg) was 8xthat of soluble antigen and the high dose group (10 µg) was 32xthat of soluble antigen. A moderate increase in the HAI titre was found for the additional control groups examining physical mixtures of Flu with PLGpS microparticles or physical mixtures of Flu, PLGpS microparticles and BAY R1-005. The HAI responses elicited with physically mixed Flu and PLGpS microparticles was found to be 4xhigher for the low dose group and 8xhigher for the high dose group than that obtained with soluble antigen of similar dose. The HAI responses elicited for physical mixtures of Flu with PLGpS microparticles and BAY R1-005 was found to be 4xhigher than that obtained with soluble antigen, irrespective of dose.

The studies presented in this Example demonstrate that viral antigens from influenza virus elicit high levels of functional antibodies when the antigens are entrapped in microparticles in the presence of an additional adjuvant (as determined by HAI titres), formed in accordance with the present invention. There is a dose dependence observed and in addition the significantly higher functional antibody (a correlate for protection) displayed by the microparticle antigen and adjuvant co-encapsulated systems after a single immunization further demonstrate the potential of these materials for development as single dosage forms.

Example 14

This Example examines the effects of formulation conditions typically employed for microencapsulation on individual components of Flu (trivalent) vaccine.

Flu (trivalent) vaccine contains three homologous HA strains (A/Texas, A/Johannesburg and B/Harbin) in approximately equal amounts. The quantitation of each specific HA component has been determined by single radial diffusion assay (SRID) (ref. 32). The SRID assay employs polyclonal sera to detect each HA component and is an effective indicator for conformational changes. The minimal concentration detectable with this assay for each component is approximately 10 µg/mL. A series of samples containing 2.0 mL of Flu (trivalent) vaccine (concentration=265 µg/mL) were prepared. For each of these samples, the concentration of A/Texas specific HA=20.25 µg/mL, A/Johannesburg specific HA=20.60 µg/mL and B/Harbin specific HA=21.42 µg/mL, respectively, was determined by SRID.

The effects of solvents typically employed in microencapsulation procedures, such as Dichloromethane (DCM) or Ethyl Acetate (EtOAc), were evaluated under conditions that simulate the homogenization procedure. Short sonication times (30 seconds) were used to model this. Additionally, small amounts of additives, such as BAY (a glyco-lipopeptide) and DC-Chol (a cationic lipid), were examined to determine if improved recovery of antigen can be confirmed.

The scale of the reaction was designed to mimic the procedures as described in Example 5. The organic solvent was evaporated from each mixture prior to SRID analysis and suitable controls were examined to determine if the organic solvent, homogenizing method or addition of BAY or DC-Chol perturbed the results in any way.

The results of this study are shown in Table 8. The effects of sonication on the sample were minimal as shown by comparing entries 1 and 2. Entries 3 and 4 show that the recovery of antigen was affected by sonication in organic solvents like EtOAc or DCM. When EtOAc is employed, 75% of A/Texas specific HA and 78% of A/Johannesburg specific HA is recovered. No B/Harbin specific HA component was detectable by this method after treatment with EtOAc. This result indicates that less than 50% of this component was actually recovered, as the lower detection limit is about 10 µg/mL. When DCM was employed as solvent, 85% of A/Texas specific HA, 96% of A/Johannesburg specific HA and less than 50% of B/Harbin specific HA component were recovered respectively.

Entries 5 and 6 examine the influence of BAY or DC-Chol as additive in the organic phase with EtOAc as solvent. For this combination, all components were detectable (at levels>50%) with 65% (BAY) or 82% (DC-Chol) A/Texas specific HA recovered, 82% (BAY) or 70% (DC-Chol) B/Harbin specific HA recovered and 87% (BAY) or 88% (DC-Chol) A/Johannesburg specific HA recovered respectively. Entries 7 and 8 examine BAY or DC-Chol as an additive in the organic phase with DCM as solvent. The assay indicates that some components were not completely recovered or that the assay is effected in some way. Specifically, 91% (BAY) or 92% (DC-Chol) A/Texas specific HA is recovered. Less than 50% B/Harbin specific HA was recovered in either case. The results for A/Johannesburg specific HA are inconclusive due to deviations from linearity with these combinations. This occurred only when DCM was used as solvent.

Maximum recovery of all components was obtained for formulations employing Flu (trivalent) vaccine in EtOAc with BAY or DC-Chol as additive. This Example indicates that materials with lipophilic properties, such as BAY or DC-Chol, can be used to stabilize vaccine formulations containing sensitive components. Materials with these properties can function at interfaces such that proteins are protected from the air/water hydrophobic surface during homogenization. Protein conformation is particularly sensitive to these effects. The SRID assay results reported in this Example support these conclusions.

Example 15

This Example illustrates the single dose immunogenicity of Flu (trivalent) or Flu (trivalent)+adjuvant cocktails coencapsulated within PLGpS microparticles in mice immunized subcutaneously.

Flu (trivalent) vaccine contains three homologous HA strains (A/Texas, A/Johannesburg and B/Harbin) in approximately equal amounts. The total HA content in 10.0 µg of flu (trivalent) vaccine is 2.35 µg. Each specific HA component has been determined by single radial diffusion assay (SRID) (ref. 32) to be 0.76 µg A/Texas, 0.81 µg A/Johannesburg and 0.78 µg B/Harbin respectively.

In this study the dose of HA administered for each component strain was significantly less than that used in Example 13. For comparison, the monovalent vaccine used in Example 13 contained approximately 3.25 µg of A/Texas specific HA.

Mice were immunized by the subcutaneous route in the presence of adjuvants chosen based on $Th_2/Th_1$ profile; DC-Chol (a cationic lipid) and BAY R1-005 (glyco-lipopeptide with more balanced $Th_2/Th_1$), PCPP (poly[di (carboxylatophenoxy)-phosphazene] sodium salt, (Virus Research Institute, Cambridge Mass.), primarily $Th_2$. PLGpS microparticles have been shown to induce a more balanced $Th_2/Th_1$ profile, as described in Example 8.

Groups of eight 6 to 8 week old female DBA-2 mice (Charles River Breeding Laboratories, Wilmington, Mass.) were immunized subcutaneously (S.C.) with the following amounts of antigen in 250 µL of PBS (pH 7.4) on day 1: PLGpS microparticles prepared as described in Example 5 containing 10.0 µg of Flu (trivalent–2.35 µHA) or 10.0 µg of Flu (trivalent–2.35 µg HA) and BAY R1-005, DC-Chol or PCPP (Table 5).

The core loading of PLGpS microparticles containing Flu (trivalent) was determined via amino acid analysis (Table 6). Excellent recovery of antigen was found for all PLGpS microparticle formulations (>70%). This result is consistent with our findings that the initial concentration of protein solution can dramatically effect the encapsulation efficiencies.

The mass of microparticles administered was adjusted such that the required dose of 10.0 µg of Flu (trivalent–2.35 µg total HA) was delivered. No attempt to optimize the dose of adjuvant coadministered was made, although it is expected that this would be a function of formulation conditions.

The mice showed no gross pathologies or behavioral changes after immunization with PLGpS microparticles that contained encapsulated Flu (trivalent) vaccine or Flu (trivalent) vaccine and adjuvants cocktails. Sera were obtained on days 21, 42 and 57 and were evaluated for total IgG, IgG1, IgG2a and for the presence of functional antibody via the hemagglutination inhibition antibody assay (HAI). Each strain (A/Texas, A/Johannesburg and B/Harbin) was examined to evaluate the effects of encapsulation and release on immunogenicity and functional antibody in a multi-component system. All samples were analyzed in duplicate. The antibody ELISA's were performed as described in Example 13.

Figure 14B:
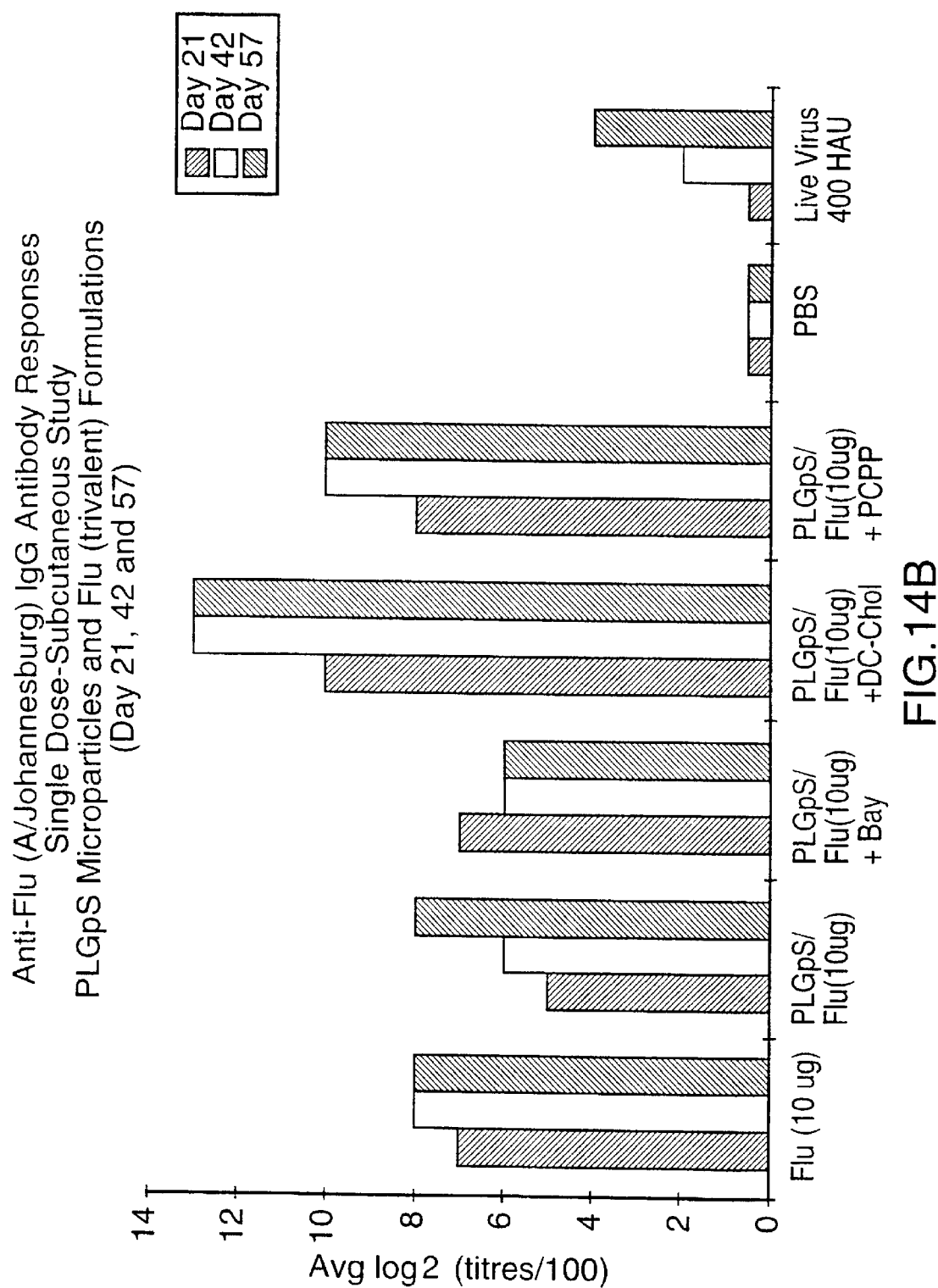

FIGS. 14a to c, show the specific IgG antibody responses elicited by PLGpS/Flu (trivalent) microparticle formulations, to each strain contained within the Flu (trivalent) vaccine.

By day 57, the highest total IgG titres were found for PLGpS/Flu (trivalent)/DC-Chol microparticle formulations. This result was true for each strain examined (A/Texas—32×response of soluble Flu control, A/Johannesburg—64× response of soluble Flu control, B/Harbin—64×response of soluble Flu control).

By day 57, slightly higher IgG antibody responses, as indicated by titre, to A/Texas (2×response of soluble Flu control) and A/Johannesburg (4×response of soluble Flu control) were found for PLGpS/Flu(trivalent)/PCPP microparticle formulations.

By day 57, essentially identical total specific IgG antibody responses (irrespective of strain), as indicated by titre, were elicited for the PLGpS/Flu (trivalent), PLGpS/Flu (trivalent)/BAY microparticle formulations and the soluble Flu (trivalent) vaccine control group. This is consistent with the results obtained in Example 13 with monovalent vaccine where similar results were observed for these three systems.

To determine the influenza hemagglutination inhibition antibody assay (HAI) for each HA strain, serum samples were heated at 56° C. for 30 min to inactivate complement and pre-treated with trypsin (0.1 mL of 8 mg/mL)/periodate (12.5 µL–0.001 M) to destroy endogenous inhibitors of hemagglutination. Serially diluted antisera were tested in duplicate for their ability to inhibit the agglutination of 1% chick red blood cells by 4 HAU of A/Texas, A/Johannesburg or B/Harbin virus respectively in a standard HAI assay (ref. 33).

Figure 15A:
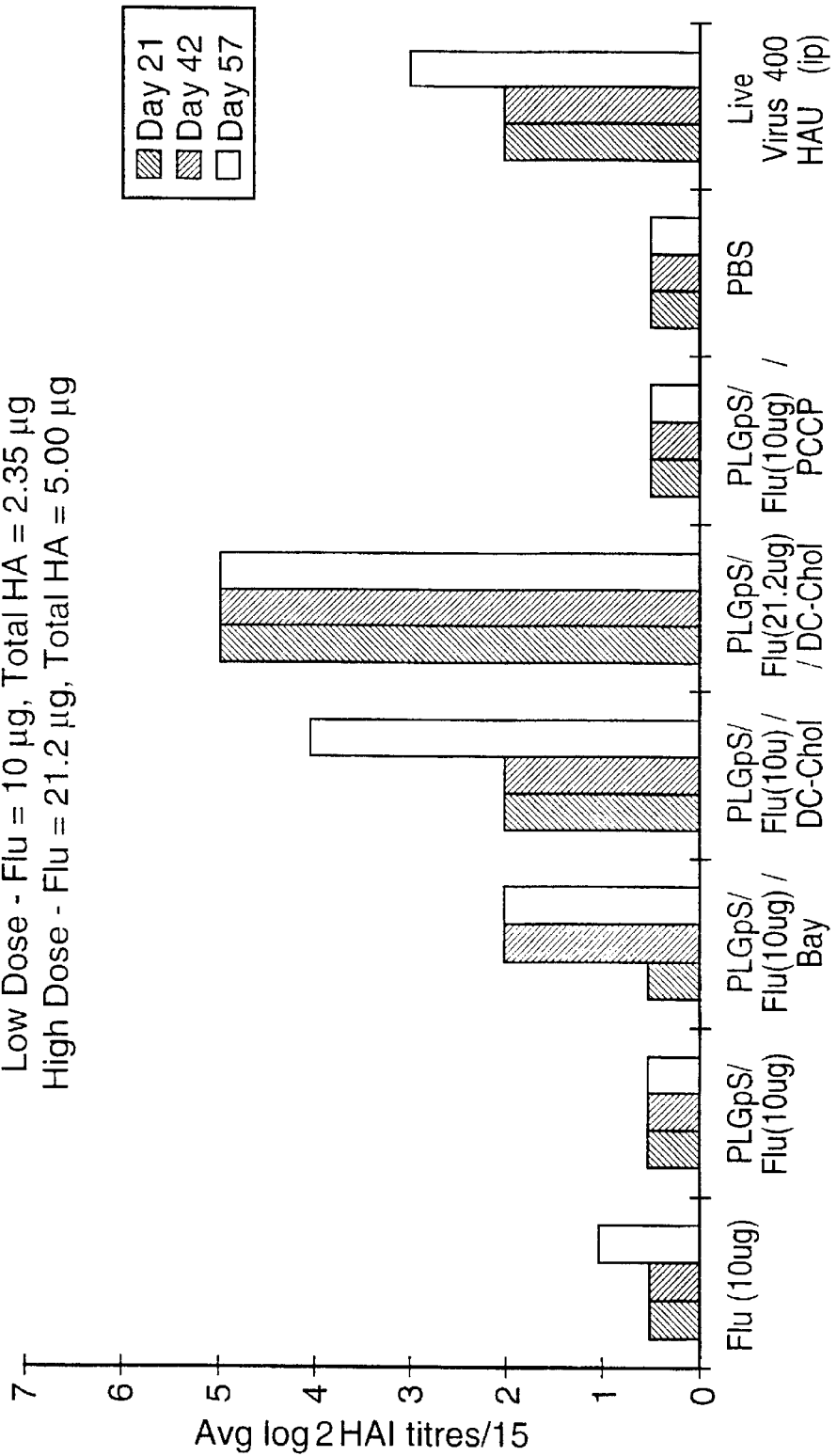
Figure 15B:
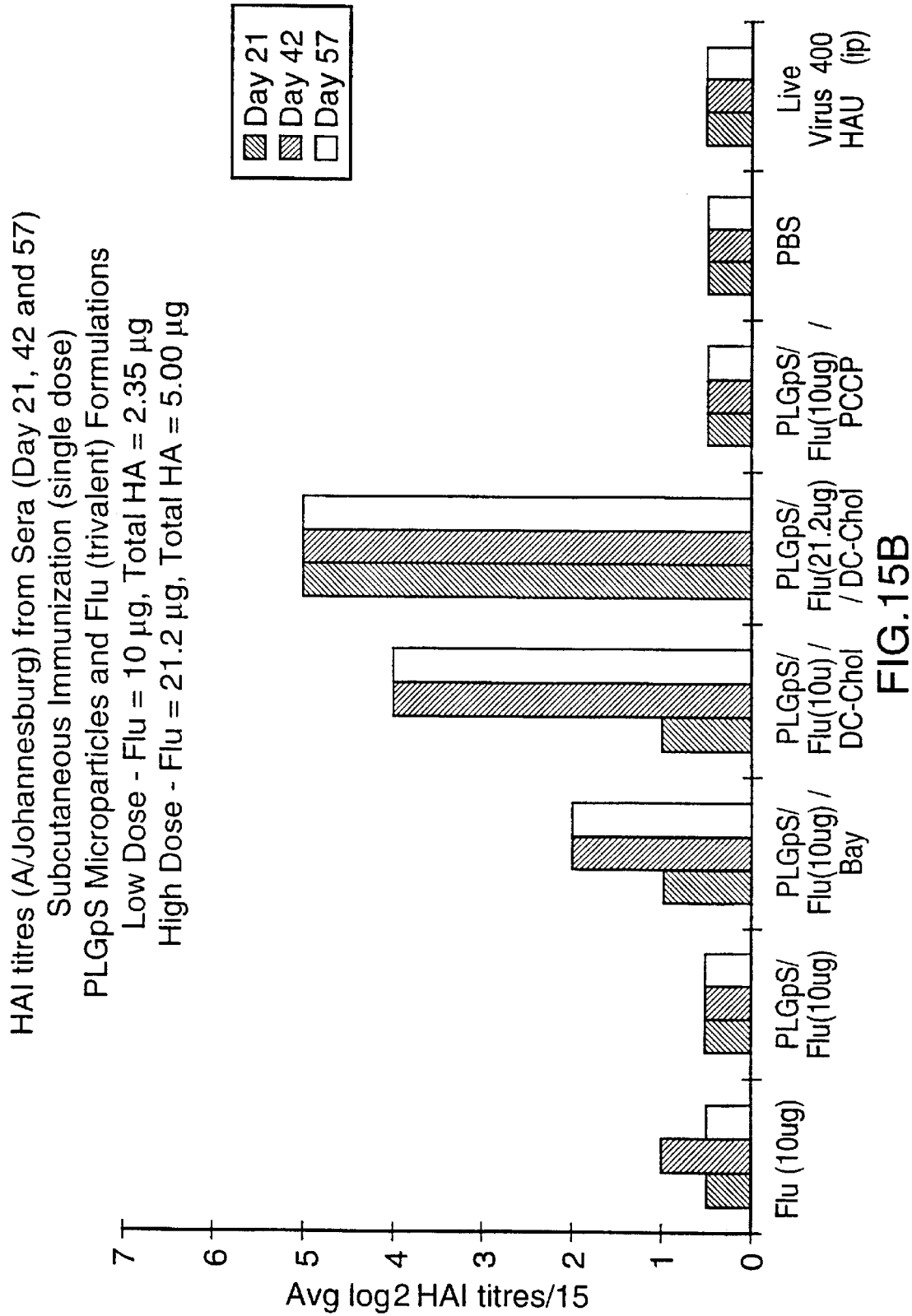

FIGS. 15a to c, show the specific HAI titres elicited to each HA strain contained within the trivalent vaccine. By day 57, the highest sustainable HAI titres were found for PLGpS microparticles formulated with Flu (trivalent) vaccine in the presence of DC-Chol (HAI titre; 240 to HA specific A/Texas (8×soluble Flu (trivalent) control), 240 to HA specific A/Johannesburg (16X soluble Flu (trivalent) control) and 60 to HA specific B/Harbin (8×soluble Flu (trivalent) control)). Notably higher titres were also found for PLGpS micropartilcles formulated with Flu (trivalent) in the presence of BAY (HAI titre; 60 to HA specific A/Texas (2×soluble Flu (trivalent) control), 60 to HA specific A/Johannesburg (4×soluble Flu (trivalent) control) and 15 to HA specific B/Harbin (equal to soluble Flu (trivalent) control)). The HAI titres found for BAY formulations with Flu (trivalent) vaccine, in this Example, are comparable to those obtained for the low dose groups in Example 13, wherein 1 μg Flu (monovalent) vaccine –0.325 μg A/Texas specific HA was administered. PLGpS/Flu (trivalent)/PCPP microparticle formulations failed to elicit any detectable functional antibody response.

An experiment was conducted examining a higher dose of PLGpS/Flu (triv)/DC-Chol formulated microparticles. This group of mice was immunized on day 1 with approximately twice the dose of Flu (triv) vaccine administered to the other groups (Dose—Flu(triv)=21.2 μg, total HA=5.00 μg). The results obtained for this high dose are included in FIGS. 15$a$ to $c$. The HAI titres elicited for a control group immunized with soluble Flu (triv) vaccine at this dose were marginal and essentially equivalent to the low dose group examined (results not shown). By day 57, this formulation elicited significantly higher specific HAI titres than the low dose group (HAI titre; 480 to HA specific A/Texas (5×soluble Flu (trivalent) control), 480 to HA specific A/Johannesburg (5×soluble Flu (trivalent) control) and 120 to HA specific B/Harbin (3×soluble Flu (trivalent) control). Additionally, it was found that the HAI titres elicited were sustainable, being maintained at these levels from day 21 through 57.

Additives, such as BAY or DC-Chol, were introduced into the organic phase, containing polymer and organic solvent wherein they can function at the interface to protect antigen during formulation procedures (see Example 13, Table 8). This serves to increase the recovery of antigenic material.

In addition, in vitro release studies have shown that a sizable amount of the encapsulated components are released within the first three days. It has been experimentally determined that about 5 to 15% of antigen encapsulated is detectable at this stage of release (antigen which is surface localized on the microparticle). The priming immunization was significantly enhanced by the co-release of adjuvants. This is likely the result of being localized in close proximity to antigen during the initial release phase.

It is noteworthy that PLGpS microparticle formulations coencapsulating antigens with adjuvants, such as PCPP, did not result in formulations with improved vaccine efficacy. This material was added to the aqueous phase of the primary emulsion and does not possess the lipophilic properties of DC-Chol or BAY. It has been demonstrated that PCPP has strong adjuvant properties in other systems, yet in this Example, a marginal improvement in encapsulation efficiency or adjuvancy of the microparticle formulation is observed.

The studies presented in this Example demonstrate that viral antigens from influenza virus in a multi-component system can elicit high levels of total IgG antibody and functional antibodies (HAI) when the Flu antigens are entrapped in microparticles in the presence of an additional co-encapsulated adjuvant, such as BAY or DC-Chol.

Example 16

This Example evaluates the infection rate and protection after single dose subcutaneous immunization with PLGpS microparticle formulations in the mouse model.

A/Taiwan/1/86 (H1N1) as live influenza viruses in egg-derived allantoic fluid, mouse-adapted A/Taiwan/1/86 and commercial A/Taiwan/1/86 monovalent subunit vaccine (Fluzone®) were obtained from Pasteur Mérieux, Connaught, USA (Swiftwater, Pa.).

Groups of 8 female DBA-2 mice aged 6 to 8 weeks (described in Example 14) were immunized subcutaneously on day 1 with Flu (trivalent) vaccine containing A/Texas, A/Johannesburg and B/Harbin strains (2.35 μg total HA in 0.25 mL PBS). Control mice received either PBS alone or 400 hemagglutination units (HAU) of live A/Texas virus as allantoic fluid. Fourteen days later, mice were challenged intranasally while under anesthesia with 50 μL of live mouse-adapted A/Taiwan/1/86 (5 LD50) in allantoic fluid. Protection was assessed by monitoring mortality daily and morbidity (weight change) every 2 days up to 14 days post-challenge.

Figure 16:
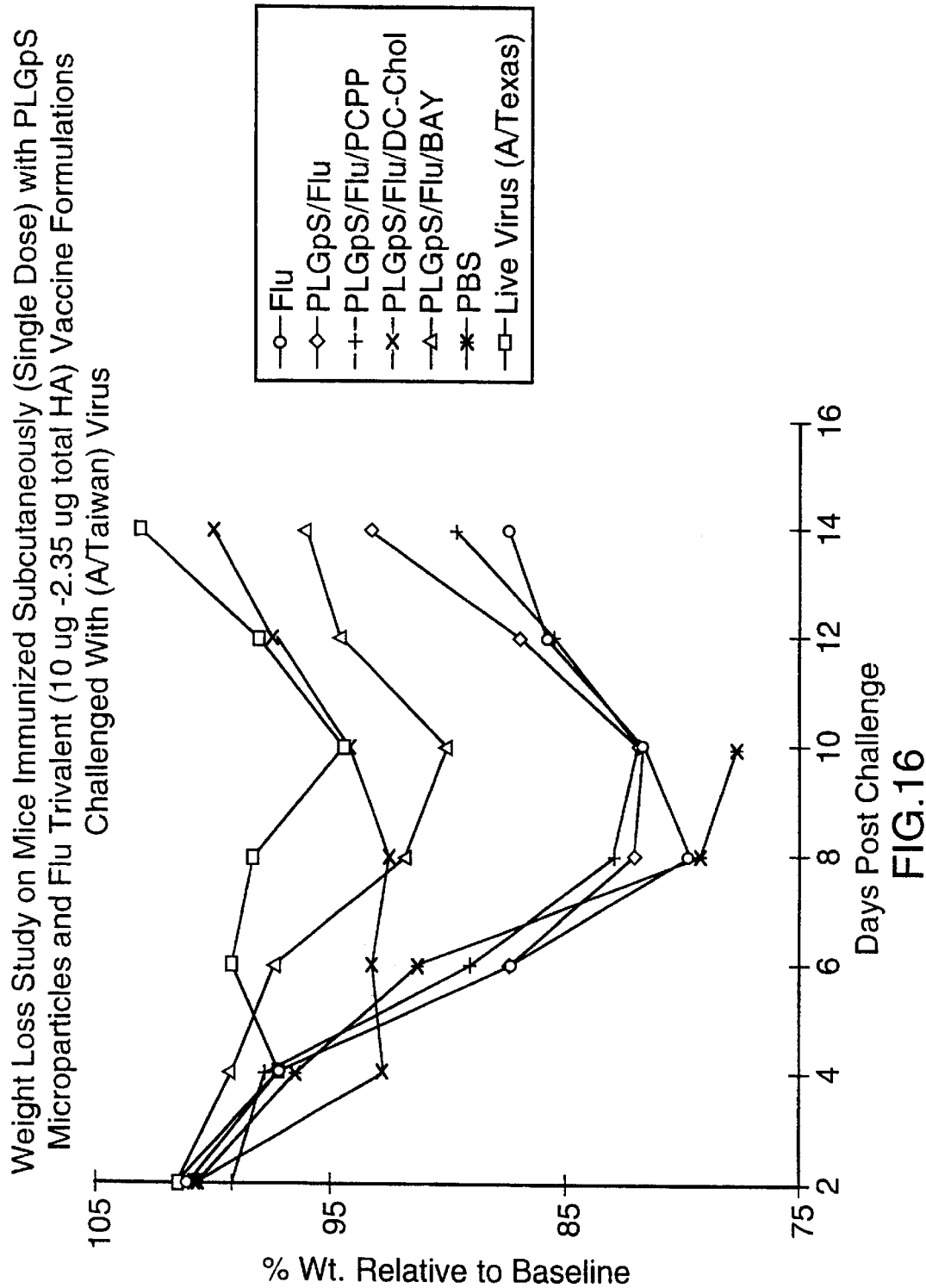
FIG. 16 shows the results of a protection study performed on mice immunized with a single dose of PLGpS/Flu (trivalent) microparticles or PLGpS/Flu (trivalent) coencapsulating BAY R1-005, DC-Chol or PCPP. The mice were challenged with homologous live virus and monitored for weight changes and survival over a 2 week interval.

FIG. 16 shows the results of the challenge. As expected, all mice immunized with homologous live (A/Texas) virus suffered minimal loss in weight and fully recovered within 2 weeks of challenge as measured by the weight percent change from baseline. Also as expected, mice immunized with PBS suffered a precipitous drop in weight which by day 10 fell below 30% of baseline. No mice in this control group survived after 10 days.

Mice immunized with PLGpS/Flu (trivalent)/DC-Chol microparticle formulations were successfully infected, as indicated by the 8% average drop in weight within 4 days post challenge. Of the PLGpS formulated groups examined, these mice exhibited the swiftest recovery, reaching 100% of baseline after 2 weeks. The entire group recovered indicating a protective titre was raised in each mouse.

Mice immunized with PLGpS/Flu (trivalent)/BAY microparticle formulations were also successfully infected, as indicated by the 10% average drop in weight by day 10. These mice recovered more slowly, reaching 95% of baseline after 2 weeks. The entire group recovered indicating that a protective titre was raised in all of these mice, although the rate of recovery indicates the level of protection was less than that seen for the DC-Chol group at this dose. This is in accordance with the HAI values determined in Example 15 for these two groups.

The soluble Flu (trivalent) vaccine control group and the PLGpS/Flu (trivalent) or PLGpS/Flu (trivalent)/PCPP microparticle formulations were less successful. These groups experienced a 23 to 29% average drop in weight by days 8–10 post challenge. The rate of recovery was slowest for these mice reaching 86 to 92% of baseline after 2 weeks. Additionally not all mice in these groups survived. Six of eight mice survived from the PLGpS/Flu (trivalent) microparticle formulated group. Seven of eight survived from the PLGpS/Flu (trivalent)/PCPP formulated group and six of eight survived from the soluble Flu (trivalent) control group. In each of these cases no or low protection is observed.

In Example 14, we evaluated the effects of microencapsulation formulation conditions on the Flu (trivalent) vaccine. Strain-specific (A/Texas, A/Johannesburg and B/Harbin) analysis of antigen recovery by SRID suggested that minimal loss in antigenic activity for all three strains in this multi-component system could be expected when employing DC-Chol or BAY in the organic phase with PLGpS polymer and EtOAc as solvent.

In Example 15, the higher functional antibody (a correlate for protection) elicited by single subcutaneous administration of PLGpS/Flu (trivalent) vaccine formulated in the presence of DC-Chol or BAY demonstrated the utility of these formulations in the mouse model. The results of the challenge/protection study, described in Example 16, are in agreement with the ranking for protection as suggested by the functional antibody studies.

The delivery of antigen and adjuvant within a biodegradable microparticle can result in more efficient presentation to the immune system. The adjuvancy found for soluble mixtures of DC-Chol or BAY with antigen(s) may be significantly increased by employing this formulation strategy. The possibility for fewer and lower (antigen/adjuvant) dose regimens is indicated by these results. Specifically, this Example strongly indicates the potential of these new microparticle based formulations for development as a single efficacious dosage form.

Example 17

This Example illustrates the immunogenicity of transferrin binding protein (Tbp-2) derived from Moraxella catarrhalis (as described in WO 97/13785, assigned to the assignee hereof and the disclosure of which is incorporated herein by reference) encapsulated in PLGpS microparticles, Tbp-2 physically mixed with PLGpS microparticles or Tbp-2 formulated with Alum in mice immunized subcutaneously.

Groups of five, 6 to 8 week old female BALB/c mice (Charles River Breeding Laboratories, Wilmington, Mass.) were immunized subcutaneously (S.C.) with the following amounts of antigen in 250 $\mu$L of PBS (pH 7.4) on days 1, 28 and 43: PLGpS microparticles prepared as described in Example 5 containing 0.3 $\mu$g of Tbp-2; PLGpS microparticles prepared as described in Example 5 physically mixed with 0.3 $\mu$g of Tbp-2; and Alum (1.5 mg/dose) formulated with 0.3 $\mu$g of Tbp-2 (Table 5).

The mice showed no gross pathologies or behavioral changes after receiving microparticles that contained encapsulated Tbp-2, microparticles physically mixed with Tbp-2 or Alum physically mixed with Tbp-2. Sera were collected on days +14, +27, +42 and +55 and were evaluated for the presence of anti-Tbp-2 IgG antibodies by antigen specific ELISA as described in Example 8. All samples were analysed in duplicate.

The core loading of PLGpS microparticles containing tbp-2 was determined via amino acid analysis (4.0 $\mu$g/mg (32.8%)) as described in Example 6.

The results of immunizations (FIG. 17a) indicate that antigen presented to the immune system entrapped in PLGpS microparticles elicited a substantially higher titre than that obtained for soluble antigen or for antigen physically mixed with PLGpS microparticles alone. In addition, this study indicates that microencapsulated formulations were as immunogenic as the traditional Alum adjuvanted systems. The kinetics of the immune response were found to be similar for both formulations.

The IgG subtype profile (FIG. 17b) for the bleed obtained on day 55 revealed differences in the immune responses elicited for Tbp-2 encapsulated in PLGpS microparticles and Tbp-2 physically mixed with PLGpS microparticles or formulated with Alum. IgG1 is the dominant subtype detected (with some IgG2b) when antigen was administered in soluble form or as a physical mixture with PLGpS microparticles or formulated with Alum.

In this Example, the IgG subtypes induced by Tbp-2 encapsulated within PLGpS microparticles elicit comparatively more IgG2a. This trend is a similar trend to that observed for Hin-47 in Example 8.

These results suggest that the mechanisms of immune response induced by immunizing with encapsulated antigens are different from that generated with Alum. A more balanced $Th_2/Th_1$ profile (as indicated by the IgG2a:IgG1 ratio) is exhibited when antigen is administered encapsulated within microparticles.

As may be seen from the results herein, the quality of the immune response mediated by PLGpS microparticles encapsulating antigen is substantially different from that obtained by physically mixing with PLGpS microparticles, formulating with Alum or by administering soluble antigen alone. Additionally, the magnitude of the immune response induced by Alum in antigen/Alum formulations is comparable to that provided by microparticles containing encapsulated antigen.

Example 18

This Example illustrates the immunogenicity of Tbp-2 encapsulated in PLGpS microparticles and Tbp-2 physically mixed with PLGpS microparticles in mice immunized intranasally.

Groups of five, 6 to 8 week old female BALB/c mice (Charles River Breeding Laboratories, Wilmington, Mass.) were immunized intranasally (I.N.) with the following amounts of antigen in either 10 $\mu$L or 50 $\mu$L of PBS (pH 7.4) on days 1, 28 and 43: PLGpS microparticles prepared as described in Example 5 containing 6.0 $\mu$g of Tbp-2; and PLGpS microparticles prepared as described in Example 5 physically mixed with 6.0 $\mu$g Tbp-2 (Table 5).

The mice showed no gross pathologies or behavioral changes after immunization with PLGpS microparticles that contained encapsulated Tbp-2 or PLGpS microparticles that were physically mixed with Tbp-2. Sera were obtained on days 14, 27, 42 and 55 and were evaluated for the presence of anti-Tbp-2 IgG antibodies by antigen specific ELISA as described in Example 8. All samples were analyzed in duplicate.

The core loading of PLGpS microparticles containing Tbp-2 was determined via amino acid analysis (4.0 $\mu$g/mg (32.8%)) as described in Example 6.

Figure 18:
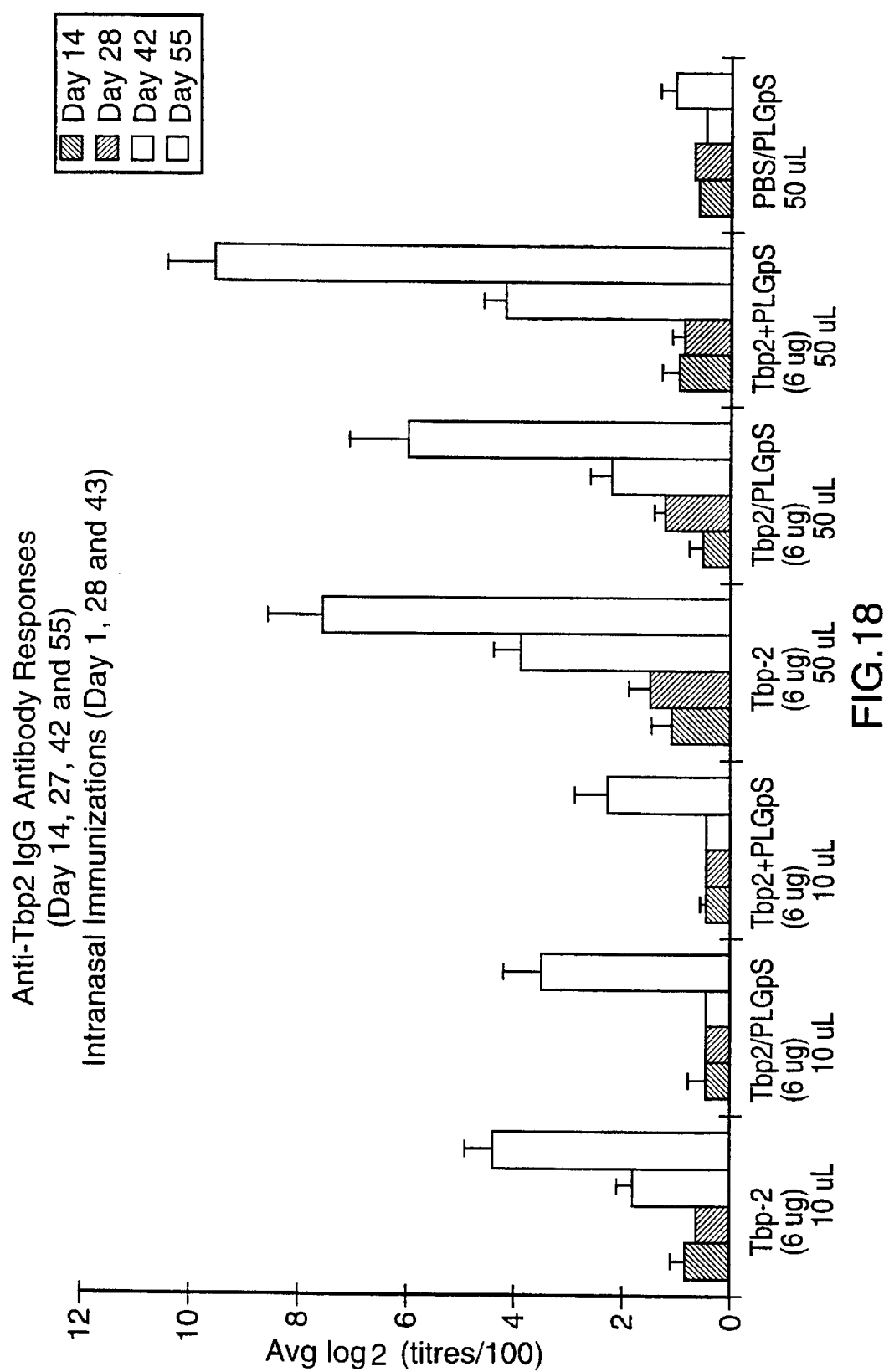
FIG. 18 shows the IgG serum antibody responses in mice immunized intranasally (I.N.) with the transferrin binding protein from *Moraxella catarrhallis* (Tbp-2). Groups of 5 mice were immunized on days 1, 28 and 43 with either 10 μL or 50 μL of PBS, pH 7.4, containing 6 μg of Tbp-2 incorporated into microparticles or physically mixed with PLGpS microparticles. Sera obtained on days +14, +27, +42 and +55 were evaluated for the presence of anti-Tbp-2 IgG antibodies using an enzyme-linked immunosorbent assay (ELISA).

The serum IgG Tbp-2-specific antibody titres following I.N. immunization is shown in FIG. 18. When the volume of the dose administered was low (10 $\mu$L) these results indicate that an antigen (Tbp-2) incorporated into or physically mixed with PLGpS microparticles is less immunogenic than soluble antigen of similar dose (6.0 $\mu$g).

When the volume of the dose was increased (50 $\mu$L), the overall titres are significantly higher for all groups. These results indicate that an antigen (Tbp-2) physically mixed with PLGpS microparticles is substantially more immunogenic than microparticle encapsulated antigen or for soluble antigen of similar dose (6.0 $\mu$g) in accordance with earlier observations made for intranasal immunization of Hin-47 (Example 10).

In our initial study with intranasal Hin-47 immunizations, Example 10, it was found that a strong humoral response and robust secretory response were obtained by administering Hin-47 physically mixed with microparticles. This study with Tbp-2 has confirmed the earlier observations. Additionally, we have established that the volume of the dose administered plays a significant role in the type and strength of the immune response invoked.

Example 19

This Example illusrates the release of antigen from the microparticles.

Having established that antigen encapsulated within PLGpS microparticles is as immunogenic as Alum formulations, we next sought to examine whether the prime and delayed release character of antigens encapsulated within these polymeric matrices could be exploited so that fewer immunizations would be needed.

In this Example, we examined the immunogenicity of Tbp-2 encapsulated in PLGpS microparticles, physically mixed with PLGpS microparticles or formulated with Alum or CFA/IFA in guinea pigs immunized subcutaneously.

Groups of two, 6 to 8 week old female guinea pigs (Charles River Breeding Laboratories, Wilmington, Mass.) were immunized subcutaneously (S.C.) with the following amounts of antigen: PLGpS microparticles encapsulating 5.0 μg of tbp-2 suspended in 500 μL of PBS (pH 7.4) on days 1 and 28, prepared as described in Example 5; Complete Freunds Adjuvant (CFA) formulated in PBS (pH 7.4) with 5.0 μg of Tbp-2 on day 1 followed intramuscularly (I.M.) by Incomplete Freunds Adjuvant (IFA) formulated in PBS (pH 7.4) with 5.0 μg of Tbp-2 on days 14 and 28; or Alum formulated in PBS (pH 7.4) with 5.0 μg of Tbp-2 on days 1, 14 and 28 (Table 5).

The guinea pigs showed no gross pathologies or behavioral changes after immunization with PLGpS microparticles that contained encapsulated Tbp-2, PLGpS microparticles physically mixed with Tbp-2, CFA/IFA formulated Tbp-2 or Alum formulated Tbp-2. Sera were obtained on days 40 and 56 and were evaluated for the presence of anti-Tbp-2 IgG antibodies by antigen specific ELISA. All samples were analyzed in duplicate. The antibody ELISA's are described in Example 8.

The core loading of PLGpS microparticles containing Tbp-2 was determined via amino acid analysis (4.0 μg/mg (32.8%)) as described in Example 6.

The results shown in FIG. 19 indicate that two doses of PLGpS microencapsulated Tbp-2 elicited similar anti-Tbp-2 antibody responses as 3 doses of Tbp-2 formulated either in CFA/IFA or with Alum.

The present results strongly suggest that microencapsulated Tbp-2 may be exploited as a candidate vaccine for two dose schedules.

Example 20

This Example illustrates the immunogenicity of rUrease or rUrease/adjuvant cocktails encapsulated within PLGpS microparticles in mice immunized subcutaneously or intragastrically.

Groups of eight, 6 to 8 week old outbred Swiss female mice (Janvier, France) were immunized subcutaneously (S.C.) with the following amounts of antigen in 300 μL of PBS (pH 7.4) on days 1 and 28 and 56: PLGpS microparticles prepared as described in Example 5 containing 10.0 μg of rUrease; and PLGpS microparticles prepared as described in Example 5 coencapsulating 10.0 μg of rUrease and DC-Chol, PCPP or CT-X; 10.0 μg of rUrease plus soluble DC-Chol (65 μg/dose) or PCPP (100 μg/dose) as controls or intragastrically (I.G.) with the following amounts of antigen in 300 μL of 0.15 M NaHCO$_3$ (pH 9.0) on days 1, 28 and 56: PLGpS microparticles prepared as described in Example 5 containing 40.0 μg of rUrease; and PLGpS microparticles prepared as described in Example 5 coencapsulating 40.0 μg of rUrease and DC-Chol, PCPP or CT-X (Table 5).

The core loading of PLGpS microparticles containing rUrease was determined via amino acid analysis or polyclonal rUrease specific ELISA (Table 7) as described in Example 6. The polyclonal ELISA assay performed on PLGpS microparticle extracts typically provides a measure of total protein (recovered epitope) encapsulated. Control experiments have allowed us to quantify the extent to which the solvent/base (SDS) extraction procedure effects the integrity of the antigen. Under the conditions employed we have estimated that about 65 to 75% of the extracted protein remains fully detectable by this assay. Thus this determination will be lower than the measure of total protein recovered via amino acid analysis (AAA). Suitable controls were included to ensure that the presence of the adjuvants (DC-Chol, CT-X or PCPP) did not interfere with the results obtained. The presence of DC-Chol did not seem to influence the assay, however, PCPP provided anomalous values which were uncharacteristically higher when compared to the total protein by AAA in some analyses. In the case of CT-X, a separate polyclonal ELISA assay was developed to quantify the amount of CT-X coencapsulated.

The mass of microparticles administered was adjusted such that the required dose of 10.0 μg of rUrease (subcutaneously) or 40.0 μg of rUrease (orally) was delivered.

The mice showed no gross pathologies or behavioral changes after immunization with PLGpS microparticles that contained either encapsulated rUrease or coencapsulated mixtures of rUrease and adjuvant. Sera were obtained on day 85 and were evaluated for the presence of anti-rUrease IgG1 and IgG2a antibodies by antigen specific ELISA. All samples were analyzed in duplicate.

ELISA's were performed according to standard protocols (biotinylated conjugates, streptavidine peroxidase complex were from Amersham and o-phenylenediamine dihydrochloride (OPD) substrate from Sigma). Plates were coated overnight at 4° C. with *H. pylori* extracts (5 μg/mL) in 0.05M carbonate-bicarbonate buffer (pH 9.6). After saturation with BSA (Sigma), plates were incubated with sera (1.5 hrs), biotinylated conjugate (1.5 hrs), strepavidin peroxidase complex (1 h) and substrate (OPD—10 min). A polyclonal mouse serum directed against *H. pylori* extract served as a control in each experiment. The titres were expressed as the inverse of the dilution giving 50% of the maximal absorbance value at 492 nm. Pre-immune sera is used as negative control.

Mice were immunized by the subcutaneous or intragastric route in the presence of adjuvants chosen based on Th$_2$/Th$_1$ profile (DC-Chol—more balanced Th$_2$/Th$_1$, PCPP—primarily Th$_2$) or for known mucosal adjuvancy (Cholera Toxin (CT-X) or heat labile enterotoxin from *E. coli* (LT)). PLGpS microparticles have been shown to induce a more balanced Th$_2$/Th$_1$ profile relevant to other typical adjuvants, such as Alum.

The IgG subtype profile for pooled bleeds obtained on day 85 after subcutaneous immunizations is shown in FIG. 20. In all cases, the IgG1 response was higher than the IgG2a response (IgG2a:IgG1 ratio ranges from 0.08 to 0.33) when PLGpS/rUrease microparticle formulations were administered subcutaneously. The total IgG1 response for the soluble control groups (rurease+DC-Chol or PCPP) was in the same absolute range. There are differences noted for the IgG2a responses between adjuvant systems that were either coencapsulated with antigen or administered as a physical mixture with antigen.

For PLGpS/rUrease microparticles (IgG2a:IgG1=0.33), PLGpS/rUrease/CT-X (IgG2a:IgG1=0.30) and PLGpS/rUrease/DC-Chol (IgG2a:IgG1=0.20), a more balanced IgG2a:IgG1 antibody response (indicative of Th$_2$/Th$_1$ ratio) was obtained. For comparison, the rUrease+DC-Chol control group IgG2a:IgG1=0.03.

For PLGpS/rUrease/PCPP microparticle formulations, primarily a $Th_2$ response is noted IgG2a:IgG1 ratio=0.08. The analogous soluble mixture of rUrease+PCPP is strongly $Th_2$ biased with a very low IgG2a:IgG1 ratio=0.003.

In general, coencapsulation of antigen in the presence of these adjuvants tends to shift the typical immunological profile towards a more balanced $Th_2/Th_1$ response.

Immunization via the intragastric route in most cases did not elicit any detectable systemic response. Notable exceptions to this are the positive control with LT having a modest systemic response (IgG2a:IgG1 ratio=0.1) and for rUrease/PLGpS microparticles coencapsulating CT-X (IgG2a:IgG1 ratio=2.1). Interestingly, for oral immunizations, encapsulated antigen plus mucosal adjuvant induces a strikingly different systemic antibody response. The ratio of IgG2a:IgG1 is now strongly in favor of IgG2a indicative of the $Th_1$ path. Examination of the literature reveals that CT-X co-administered with antigen orally typically induces an immune response similar to that elicited by LT. Primarily an IgG1 or $TH_2$ type of response is reported (ref. 34). This study illustrates that the quality of the immune response may be changed as a consequence of coencapsulation in PLGpS microparticles.

Example 21

This Example evaluates the infection rate and protection after subcutaneous or oral immunizations with PLGpS microparticle/rUrease formulations in the mouse model.

Mice were challenged 6 weeks after the 2'nd boost (Day 85) by gastric gavage with 300 μL of a suspension of *H. pylori* bacteria ($3 \times 10^6$ cfu). Based on in vitro release studies (Example 7), antigen release from microparticles requires approximately 4 weeks, thus the challenge was scheduled for 2 weeks after this time point.

Four weeks after the challenge, mice were killed and stomachs were sampled to evaluate urease activity (Jatrox test, Procter and Gamble) in a sterile flow hood. Urease activity was assessed 24 hours post-mortem by measuring the absorbance at 550 nm. The principle of the test is that the urea present in the test medium is split by *Helicobacter pylon* urease. The rise in pH causes a color change in the indicator which is likewise present in the test medium (phenol red), from yellow to pink red.

Mice were infected with a streptomycin-resistant mouse-adapted strain (X43-2AN) of *H. pylori*. The infection rate was reproducible; 100% of the mice were infected in all experiments, as judged by urease activity measured in the stomach (Jatrox test). It is to be noted that the streptomycin resistance of the challenge strain allows it to grow on a highly selective medium, making this test very sensitive (no contaminants coming from the normal flora).

This strain was stored at −70° C. in Brucella Broth (BB) (Biomerieux) supplemented with 20% v/v glycerol and 10% v/v foetal bovine serum (FBS) (Hyclone). The challenge suspension was prepared as follows: for pre-culture, *H. pylon* was grown on Mueller-Hinton Agar (MHA; Difco) containing 5% v/v sheep blood (Biomerieux) and antibiotics: Thrimethoprim (5 μg/mL), Vancomycin (10 μg/mL), Polymixin B sulphate (5 μg/mL), Amphotericin (5 μg/mL) and Streptomycin (50 μg/mL) selective marker of *H. pylori* strain X43-2AN (TVPAS) All antibiotics were purchased from Sigma. MHA-TVPAS plates were incubated for 3 days at 37° C. under micro-aerobic conditions. The pre-culture was used to inoculate a 75 cm² vented flask (Costar) containing 50 mL of BB supplemented with 5% v/v FBS and all antibiotics (TVPAS). The flask was kept under micro-aerobic conditions with gentle shaking for 24 hrs. The suspension was characterized by Gram's staining, urease activity (Urea indole medium, Diagnostic Pasteur), catalase ($H_2O_2$, 3% v/v) and oxidase activity (Biomerieux discs). Viability and motility were checked by phase contrast microscopy. The suspension was diluted in BB to O.D. 550 nm=0.1 (which was equivalent to $1 \times 10^7$ CFU/mL).

In this study, mice for which an OD.<0.1 was obtained were considered protected or at least have less than $10^3$ to $10^4$ bacteria/stomach (compared to $10^5$ to $10^6$ in controls). Groups of mice representing unimmunized/infected and unimmunized/uninfected controls were also included in the study (results not shown).

FIG. 21a, shows that protection (via the subcutaneous route), as judged by the assay described above, follows the ranking PLGpS/rUrease/DC-Chol (geometric mean=0.092) >PLGpS/rUrease/CT-X (geometric mean=0.105), PLGpS/rUrease (geometric mean=0.163) and PLGpS/rUrease/PCPP (geometric mean=0.269). The LT +rUrease (oral) positive control group (geometric mean=0.136) is the standard for protection in this study. Interestingly, typical results with rUrease plus soluble DC-Chol (geometric mean=0.600) or rUrease plus PCPP (geometric mean=1.07) control groups clearly show the advantages of coencapsulating antigen and adjuvant as a PLGpS microparticle formulation.

Mann-Whitney statistical analysis of the data presents the following conclusions. The PLGpS/rUrease/DC-Chol and PLGpS/rUrease/CT-X formulations were not significantly different from the LT+rUrease positive control group. The PLGpS/rUrease/PCPP, rUrease+DC-Chol and rUrease+PCPP groups were significantly different from these groups (p<0.01) and the PLGpS/rUrease group was significantly different from the PLGpS/rUrease/PCPP, rUrease+DC-Chol and the rUrease+PCPP (p<0.01) groups.

From this analysis, the PLGpS/rUrease/DC-Chol (7/8 mice have OD. <0.1) and PLGpS/Urease/CT-X (5/8 mice have OD. <0.1) microparticle groups exhibited solid protection whereas the PLGpS/rUrease (2/8 mice have OD. <0.1) microparticle group and the rUrease+DC-Chol group (2/10 OD. <0.1) exhibited moderate protection and the PLGpS/rUrease/PCPP (0/8 mice have OD. <0.1) microparticle group and the rUrease+PCPP groups (0/10 OD. <0.1) exhibited low or no protection respectively. This ranking tends to follow the more balanced $Th_2/Th_1$ ratios as determined from immunogenicity studies (Example 20).

FIG. 21b shows that no full protection via the oral route was observed for all groups of mice immunized by PLGpS microparticles containing additional adjuvants.

Statistical ranking follows the order PLGpS/rUrease/CT-X (geometric mean=0.229) >PLGpS/rUrease/DC-Chol (geometric mean=0.403), PLGpS/rUrease (geometric mean=0.475) and PLGpS/rUrease/PCPP (geometric mean= 0.493). The LT+rUrease (oral) group (geometirc mean= 0.136) is the positive control for this study.

Mann-Whitney statistical analysis of the data presents the following conclusions. The LT+rUrease positive control group was significantly different than the PLGpS/rUrease/DC-Chol and PLGpS/rUrease/CT-X formulations (p <0.01). The PLGpS/rUrease/DC-Chol and PLGpS/rUrease/CT-X formulations were not significantly different from each other. The PLGpS/rUrease and the PLGpS/rUrease/PCPP formulations were not significantly different form each other.

In this study, the PLGpS/rUrease/CT-X (2/8 mice have OD. <0.1) and the PLGpS/rUrease/DC-Chol (1/8 mice have OD. <0.1) microparticle formulations exhibited partial protection. Comparatively, the positive control group of rUrease plus LT exhibited solid protection (7/8 mice have OD. <0.1).

It was suggested, in Examples 14 to 16, that the presentation of adjuvant to the immune system by association with delivery vehicles, such as PLGpS, microparticles increases the adjuvants effectiveness resulting in a more efficacious vaccine.

Notably, typical control studies in this Example have examined immunogenicity and protection after immunizations with soluble mixtures of adjuvants, such as DC-Chol or PCPP, and rUrease by the subcutaneous route, and have found that protection was low to moderate. These results provide additional evidence that the presentation of antigen and adjuvant in the form of a particulated matrix can result in substantially more efficacious vaccines.

Additional benefits, such as reduced adjuvant toxicity and the possibility of modulating the quality of the immune response which is characteristic for the adjuvant employed, have been demonstrated in this Example. It was experimentally determined that the IgG subtype antibody responses to rUrease obtained after oral immunization with PLGpS/rUrease/CT-X formulated microparticles was uncharacteristically in favor of IgG2a (Thipath).

In the case of coencapsulated antigen and CT-X (a known mucosal adjuvant) administered subcutaneously or orally, it is also likely that this material stabilizes the antigen within the polymeric matrix during formulation, storage and release by a mechanism similar to that observed for microparticles prepared in the presence of HSA or BSA (ref. 35).

In conclusion, this study demonstrates the feasibility and efficacy of PLGpS microparticle based systemic immunization to induce significant protection against *H. pylori* infection in the mouse model. This study also demonstrates the feasibility for PLGpS microparticle based oral immunization to induce partial protection against *H. pylori* infection in the mouse model.

Additionally, co-encapsulation of rUrease in the presence of additional adjuvants (specifically DC-Chol or CT-X), can result in notable improvement in vaccine efficacy.

SUMMARY OF THE DISCLOSURE

In summary of this disclosure, the present invention provides a particulate carrier for an agent, particularly one having biological activity, comprising a matrix of polymer and biologically active material. The particulate carriers in the form of microparticles are able to efficiently deliver agents to the cells of the immune system of a subject following mucosal or parenteral administration to produce an immune response. Modifications are possible within the scope of this invention.

TABLE 1

| Antigen(s) entrapped in PLG, PLGpZS or PLGpS microparticles | Antigen Preparation |
|---|---|
| Hin-47 (1.55 mg/mL) + BAY (5.0 mg/mL) | 800 μL of Hin-47 in aqueous internal phase plus 40.0 mg of BAY in the organic phase |
| rD-15 (2.05 mg/mL) | 800 μL of rD-15. |
| Hin-47 (1.95 mg/mL) + rD-15 (1.95 mg/mL) | 400 μL of Hin-47 plus 400 μL of rD-15. |
| Flu X-31 (2.0 mg/mL) Flu A-Texas (1.48 mg/mL) | 800 μL of Flu X-31 or 800 μL of Flu A-Texas |
| Flu (2.0 mg/mL) + BAY (5.0 mg/mL) Flu A-Texas (1.48 mg/mL) + BAY (5.0 mg/mL) | 800 μL of Flu X-31 or 800 μL of Flu A-Texas in aqueous internal phase plus 40.0 mg of BAY in the organic phase |

TABLE 2

Summary of Microparticle Core Loading and Encapsulation Efficiencies (Hin-47, Hin-47 + Bay R1-005)

| Protein (Conc.) (Adjuvants) | Polymer | Epitope Equiv. HIN-47 via ELISA[1] (Encaps. Eff.)[3] | Total Protein via AAA[2] Encaps. Eff.)[3] | Epitope vs Total Protein % | Total Adjuvant via AAA[2] (Encaps. Eff.)[3] |
|---|---|---|---|---|---|
| Hin-47 (1.55 mg/mL) | PLG | 1.4 ug/mg (10.2%) | 2.8 ug/mg (20.4%) | 50% | |
| | PLGpZS | 5.3 ug/mg 30.8% | 7.5 ug/mg (43.5%) | 71% | |
| | PLGpS | 1.6 ug/mg (11.6%) | 3.3 ug/mg (23.9%) | 48% | |
| Hin-47 (1.55 mg/mL) Bay-R1005 (5.0 mg/mL) | PLG | 2.5 ug/mg (20.1%) | 3.8 ug/mg (30.6%) | 66% | 13.5 (3.4%) |
| | PLGpZS | 4.1 ug/mg (19.8%) | 5.5 ug/mg (26.6%) | 75% | 15.6 (3.9%) |
| | PLGpS | 6.1 ug/mg (39.4%) | 9.2 ug/mg (59.4%) | 66% | 23.2 (4.6%) |

[1] ELISA values are averages of 2 independent measurements of protein obtained after complete hydrolysis of microparticles.
[2] AAA values are averages of 2 independent measurements on protein (or adjuvant) encapsulated within microparticles and 2 independent measurements on protein (or adjuvant) obtained after complete hydrolysis of microparticles.
[3] Encapsulation efficiency (Encaps. Eff.) calculated as follows:
total mass of protein (or adjuvant) recovered/total amount of protein (or adjuvant) used × 100%

TABLE 3

Summary of Microparticle Core Loading and Encapsulation Efficiencies (rD-15, rD-15 + Hin-47)

| Protein (Conc.) | Polymer | Epitope Equivalent HIN-47 via ELISA[1] (Encaps. Eff.)[3] | Total Protein via AAA[2] Encaps. Eff.)[3] |
|---|---|---|---|
| rD-15 (1.95 mg/mL) | PLG | | 7.8 ug/mg (43.7%) |
| | PLGpZS | | 7.1 ug/mg (39.2%) |
| | PLGpS | | 7.3 ug/mg (43.7%) |
| rD-15 (1.95 mg/mL) + Hin-47 (1.95 mg/mL) | PLG | 1.6 ug/mg (8.0%) | 7.0 ug/mg (35.1%) |
| | PLGpZS | 5.5 ug/mg (26.1%) | 13.1 ug/mg (62.1%) |
| | PLGpS | 2.4 ug/mg (10.8%) | 11.6 ug/mg (52.1%) |

[1]ELISA values are averages of 2 independent measurements of protein obtained after complete hydrolysis of microparticles.
[2]AAA values are averages of 2 independent measurements on protein encapsulated within microparticles and 2 independent measurements on protein obtained after complete hydrolysis of microparticles.
[3]Encapsulation efficiency (Encaps. Eff.) calculated as follows: total mass of protein recovered/total amount of protein used × 100%

TABLE 4

Summary of Microparticle Core Loadings and Encapsulation Efficiencies for Flu X-31 + Bay R1-005 and Flu A-Texas, Flu A-Texas + Bay R1-005

| Protein (Conc.) (Adjuvants) | Polymer | Total Protein via AAA[1] (Encaps. Eff.)[2] | Total Adjuvant via AAA[1] (Encaps. Eff.)[2] |
|---|---|---|---|
| Flu X-31 (2.0 mg/mL) | PLG | 4.7 ug/mg (26.1%) | |
| | PLGpZS | 6.1 ug/mg (34.1%) | |
| | PLG

TABLE 7-continued

Summary of Microparticle Core Loadings and Encapsulation Efficiencies for rUrease and rUrease + Adjuvants

| Protein (Conc.) (Adjuvants) | Polymer | Total Protein via AAA[1] (Encaps. Eff.)[3] | Total Protein via ELISA[1] (Encaps. Eff.)[3] |
|---|---|---|---|
| rUrease (1.0 mg/mL) PCPP (1.25 mg/mL) | PLGpS | 5.97 ug/mg (67.2%) | 3.3 ug/mg (37.1%)[5] |

[1]AAA values are averages of two independent measurements of protein encapsulated within microparticles, as described in Example 6.
[2]polyclonal ELISA (capture sandwich antigen assay) conducted on microparticle hydrosylates, as described in Example 6. Average of 4 determinations.
[3]Encapsulation efficiency (Encaps. Eff.) calculated as follows: total mass of protein recovered/total amount of protein used × 100%
[4]N/D = not determinable by AAA as total protein is actually a combination of rUrease and CT-X.
[5]ELISA determination in the presence of PCPP was highly variable.

TABLE 8

Flu (trivalent) Formulations Examined by SRID's

| Flu Samples conc. = 265 ug/mL | Solvent/Solution examined | Sonicate (30 sec) | Additives (quantity) | SRID A/Texas:B/Harbin:A/Johannes (ug/mL) |
|---|---|---|---|---|
| Entry #1 | none | no | — | 20.25:20.6:21.42 |
| Entry #2 | none | yes | — | 21.73:19.8:23.05 |
| Entry #3 | EtOAc | yes | — | 15.21:N/D:16.73 |
| Entry #4 | DCM | yes | — | 17.28:N/D:20.54 |
| Entry #5 | EtOAc | yes | BAY (20 μg) | 13.04:16.8:18.63 |
| Entry #6 | EtOAc | yes | DC-Chol (20 μg) | 16.54:14.4:18.79 |
| Entry #7 | DCM | yes | BAY (20 μg) | 18.44:N/D:N/L |
| Entry #8 | DCM | yes | DC-Chol (20 μg) | 18.55:N/D:N/L |

N/D = not determined (below detection limit of ~10 μg/mL).
N/L = test failed or was not reproducible under experimental conditions.

REFERENCES

1. Levine, M. M.; Cryz, S.; Sorenson, K.; Kaper, J.; Wasserman, S. S.; Burr, D.; Lim, Y. L.; Clemens, J.; Rifai, A. R.; Totosudirgo, H.; Losonsky, G.; Heppner, D. G.; Punjabi, N.; Witham, N.; and Simanjuntak, C., *Lancet*, 340, 1992, 689.
2. Eldridge, J. H.; Hammond, C. J.; Meulbroek, J. A.; Staas, J. K.; and Gilley, R. M., *J. Control. Release*, 11, 1990, 205.
3. Eldridge, J. H.; Tice, T. R.; Meulbroek, J. A.; Staas, J. K.; McGhee, J. R.; and Gilley, R. M., *Mol. Immunol.*, 28, 1991, 287.
4. Hagan, D. T.; Palin, K. J.; and Davis, S. S., *Vaccine*, 7, 1989, 213.
5. Mitsunobu, O.; *Synthesis*, 1981.
6. Zhou, Q., and Kohn, J., *J. Macromolecules*, 23, 1990, 3300.
7. Brode, G. L.; Koleske, J. V., *J. Macromol. Sci-Chem.*, A6, 1972, 1109.
8. U.S. Pat. No. , 2,676,945, Higgins, H. A., Condensation Polymers of Hydroxyacetic Acid, (1954).
9. U.S. Pat. No. , 3,839,297, Wasserman, D. and Versfeit, C. C., Use of Stannous Octoate Catalyst in the Manufacture of L-(-)-Lactide-Glycolide Copolymer Sutures, (1974).
10. Kohn, F. E.; Ommen, J. G., and Feigen, J., *Eur. Polym. J.*, 19, 1983, 1081.
11. Kohn, F. E.; Van Den Berg, J. W. A.; and Van De Ridder, G., *Journal of Applied Polymer Science*, 29, 1984, 4265.
12. Kricheldorf, H. R.; and Dunsing, R., *Polymer Bulletin*, 14, 1985, 491.
13. Kricheldorf, H. R.; Jonte, J. M.; and Berl, M., *Macromol. Chem. Suppi.*, 12, 1985, 25.
14. Leenslag, J. W.; and Pennings, A. J., *Makromol. Chem.*, 188, 1987, 1809.
15. Kricheldorf, H. R.; and Sumbel, M., *Eur. Polymer J.*, 25, 1989, 585.
16. Hayashi, T.; and Iwatsuki, M., *Biopolymers*, 29, 1990, 549.
17. Hayashi, T.; Likuza, Y.; Oya, M.; and Iwatsuki, M., *J. Appl. Polym. Sci.*, 43, 1991, 2223.
18. Hayashi, T.; likuza, Y.; Oya, M.; and Iwatsuki, M., *Polym. J.*, 5, 1993, 481.
19. Kohn, J.; and Langer, R., *J. Am. Chem. Soc.*, 109, 1987, 817.
20. Yonezawa, N.; Toda, F.; Hasegawa, M., *Makromol. Chem. Rapid Commun.*, 6, 1985, 607.
21. Helder, J.; and Feijen, J., *Makromol. Chem. Rapid Commun.*, 7, 1986, 193.
22. Veld, P. J. A.; Dijkstra, P. J.; Lochem, J. H. van; and Feigen, J., *Makromol. Chem.*, 191, 1990, 1813.
23. Langer, R.; Barrera, D. A.; Zylstra, E.; and Lansbury, P. T., *J. Am. Chem. Soc.*, 115, 1993, 11010.
24. Barrera, D. A.; Zylstra, E.; and Lansbury, P. T., *Macromolecules.*, 28, 1995, 425.
25. P.C.T. Int. Appl. 94 09760, Barrera, D.; Langer, R. S.; Lansbury, P. T. Jr.; and Vacanti, J. P., Biodegradable Polymers for Cell Transportation, (1994).
26. Veld, P. J. A.; Dijkstra, P. J.; Zheng-Rong, S.; Gijsbert, T. A. J.; and Feigen, J., *J. Polymer Sci.*, 32(6), 1994, 1063.
27. Reed, A. M. and Gilding, D. K.; *Polymer*, 22, 1981, 494.
28. Greene, T. W.; and Wuts, P., *Protective Groups in Organic Synthesis* II, 335–338, John Wiley and Sons, Inc., New York, 1991.
29. U.S. Pat. No. 4,855,283 granted to Lockhoff et. al., 1989.
30. Wiesmuller, *Vaccine*, 8, 1989, 29.
31. Huang, L. and Gao, X., *Biochemical and Biophysical Research Communications*, 179, 1991, 280
32. Wood, J. M. et. al.; Development of Biological Standard, 1977, 39, 193–200.
33. Palmer, D. F., Coleman, M. T., Dowdle, W. R. and Schild, G. C.; "Advanced laboratory techniques for influenza diagnosis", immunology series no. 6, U.S. Dept. Health, Education and Welfare. Washington D.C.; 1975, 51–52.

34. Ruedl, C., Rieser, C., Kofler, N., Wick, G. and Wolf, H.; *Vaccine*, 1996, 14, 792–798.

35. Lu, W. and Park, T. G.; *Journal of Pharmaceutical Technology*, 1995, 49, 13–19.

36. Gopferich, A.; *Biomaterials*; 17, 1996, 103.

What we claim is:

1. A process for making a biodegradable, biocompatible polyester, which comprises co-polymerizing at least one α-hydroxy acid monomer having the formula $R_1R_2COHCO_2H$, wherein the $R_1$ and $R_2$ groups are H, linear or branched alkyl units, the alkyl units being represented by the formula $C_nH_{2n+}$, and at least one pseudo-α-amino acid monomer of the formula $R_5CHNHR_6CO_2H$, wherein the $R_5$ group is a hydroxy methyl or methyl thiol group and $R_6$ is an amine protecting group.

2. The process of claim 1, which comprises:

forming a mixture of monomers comprising said at least one α-hydroxy acid and said at least one pseudo-α-amino acid with an organic solvent solution of an esterification catalyst under inert atmospheric conditions;

copolymerizing said monomers in said organic solvent solution; and isolating the resultant polymer from said organic solvent solution.

3. The process of claim 1, wherein the α-hydroxy acids comprise a mixture of α-hydroxy acids, one of said mixture of α-hydroxy acids having $R_1$ and $R_2$ groups which are hydrogen and the other of said mixture of α-hydroxy acids having an $R_1$ group which is $CH_3$ and $R_2$ group which is H.

4. The process of claim 1, wherein the amine protecting group is selected from the group consisting of carbobenzyloxy (CBZ or Z), benzyl (Bn), para-methoxybenzyl (MeOBn), benzyloxymethoxy (BOM), tert-butyloxycarbonyl (t-BOC) and [9-fluorenylmethyl oxy] carbonyl (FMOC).

5. The process of claim 1, wherein the at least one α-hydroxy acid is selected from the group consisting of L-lactic acid, D,L-lactic acid, glycolic acid, hydroxy valeric acid and hydroxybutyric acid.

6. The process of claim 1, wherein the at least one pseudo-α-amino acid is derived from serine.

7. The process of claim 1, wherein said at least one α-hydroxy acid monomer and at least one pseudo-α-amino acid monomer are selected to result in poly-D, L-lactide-co-glycolide-co-pseudo-Z-serine ester (PLGpZS).

8. The process of claim 1, wherein said at least one α-hydroxy acid monomer and at least one pseudo-α-amino acid monomer are selected to result in poly-D, L-lactide-co-glycolide-co-pseudo-serine ester(PLGpS).

9. The process of claim 2, wherein said polymer has a molecular weight of about 5000 to about 40,000 dalton.

10. The process of claim 2, wherein the polymer formed is deprotected by solid phase catalytic reduction or acid catalysis.

11. The process of claim 10, wherein said deprotection is by acid catalysis in the presence of hydrogen bromide in acetic acid solution.

12. The process of claim 2, wherein said catalyst is stannous 2-ethylhexanoate.

13. The process of claim 2, wherein said polymerization is carried out at a temperature of about 120° C. for about 28 hours.

14. The process of claim 2, wherein said organic solvent is anhydrous chloroform.

15. The process of claim 2, wherein said process further comprises forming the polymer into a film.

16. The process. of claim 2, wherein said process further comprises forming the polymer into microparticles.

* * * * *